US009598709B2

(12) United States Patent
Kim et al.

(10) Patent No.: US 9,598,709 B2
(45) Date of Patent: Mar. 21, 2017

(54) GENETICALLY ENGINEERED AND STRESS RESISTANT YEAST CELL WITH ENHANCED MSN2 ACTIVITY AND METHOD OF PRODUCING LACTATE USING THE SAME

(71) Applicant: Samsung Electronics Co., Ltd., Suwon-si, Gyeonggi-do (KR)

(72) Inventors: Sungsoo Kim, Hwaseong-si (KR); Sunghaeng Lee, Seoul (KR); Dongsik Yang, Seoul (KR); Huisub Lim, Seoul (KR); Kwangmyung Cho, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/811,520

(22) Filed: Jul. 28, 2015

(65) Prior Publication Data

US 2016/0024537 A1 Jan. 28, 2016

(30) Foreign Application Priority Data

Jul. 28, 2014 (KR) ........................ 10-2014-0096013

(51) Int. Cl.

| | |
|---|---|
| ***C12N 1/20*** | (2006.01) |
| ***C12P 7/56*** | (2006.01) |
| ***C12N 15/00*** | (2006.01) |
| ***C12Q 1/68*** | (2006.01) |
| ***C07H 21/04*** | (2006.01) |
| ***C12N 9/04*** | (2006.01) |
| ***C12N 9/06*** | (2006.01) |
| ***C12N 9/08*** | (2006.01) |
| ***C07K 1/00*** | (2006.01) |
| ***C12N 9/02*** | (2006.01) |
| ***C07K 14/395*** | (2006.01) |

(52) U.S. Cl.
CPC .............. *C12P 7/56* (2013.01); *C07K 14/395* (2013.01); *C12N 9/0006* (2013.01); *C12N 9/0008* (2013.01); *C12N 9/0065* (2013.01)

(58) Field of Classification Search
CPC .................................................... C07K 14/395
See application file for complete search history.

(56) References Cited

U.S. PATENT DOCUMENTS

| | | | | |
|---|---|---|---|---|
| 8,178,331 | B2 | 5/2012 | Gasch et al. | |
| 2009/0053782 | A1* | 2/2009 | Dundon ................. | C12N 15/52 435/139 |
| 2010/0273226 | A1 | 10/2010 | Yu et al. | |
| 2013/0065284 | A1* | 3/2013 | Chung ................ | C12N 9/0006 435/135 |

FOREIGN PATENT DOCUMENTS

| | | | |
|---|---|---|---|
| EP | 2243790 | A1 | 10/2010 |
| JP | 2011-120486 | A | 6/2011 |
| KR | 2011-0118554 | A | 10/2011 |

OTHER PUBLICATIONS

Martinez-Pastor. The *Saccharomyces cerevisiae* zinc finger proteins Msn2p and Msn4p are required for transcriptional induction through the stress response element (STRE). EMBO J. May 1, 1996;15(9):2227-35.*

Abbott. Physiological and Transcriptional Responses to High Concentrations of Lactic Acid in Anaerobic Chemostat Cultures of *Saccharomyces cerevisiae*. Applied and Environmental Microbiology, Sep. 2008, p. 5759-5768.*

Watanabe. Overexpression of MSN2 in a sake yeast strain promotes ethanol tolerance and increases ethanol production in sake brewing. Journal of Bioscience and Bioengineering. vol. 107, Issue 5, May 2009, pp. 516-518.*

Boubekeur. Participation of acetaldehyde dehydrogenases in ethanol and pyruvate metabolism of the yeast *Saccharomyces cerevisiae*. Eur. J. Biochem. 268, 5057-5065 (2001).*

Legras et al., "Activation of Two Different Resistance Mechanisms in *Saccharomyces cerevisiae* upon Exposure to Octanoic and Decanoic Acids", Applied and Environmental Microbiology, 76(22): 7526-7635 (2010).

* cited by examiner

*Primary Examiner* — Yong Pak
(74) *Attorney, Agent, or Firm* — Leydig, Volt & Mayer, Ltd.

(57) ABSTRACT

Provided is a yeast cell having a stress tolerance, wherein the yeast cell has enhanced MSN2 activity, a method of producing the yeast cell, and a method of producing lactate by using the same.

13 Claims, 8 Drawing Sheets

GENETICALLY ENGINEERED AND STRESS RESISTANT YEAST CELL WITH ENHANCED MSN2 ACTIVITY AND METHOD OF PRODUCING LACTATE USING THE SAME

RELATED APPLICATION

This application claims the benefit of Korean Patent Application No. 10-2014-0096013, filed on Jul. 28, 2014, in the Korean Intellectual Property Office, the entire disclosure of which is hereby incorporated by reference.

INCORPORATION BY REFERENCE OF ELECTRONICALLY SUBMITTED MATERIALS

Incorporated by reference in its entirety herein is a computer-readable nucleotide/amino acid sequence listing submitted herewith and identified as follows: One 141,703 byte ASCII (Text) file named "720126_ST25.TXT" created Jul. 27, 2015.

BACKGROUND

1. Field

The present disclosure relates to a genetically engineered and stress resistant yeast cell with enhanced MSN2 activity and a method of producing lactate using the same.

2. Description of the Related Art

Organic acids are extensively used in industrial fields. For example, lactate is an organic acid which is widely used in various industries such as the food, pharmaceutical, chemical, and electronic industries. Lactate is a colorless, odorless, and highly water-soluble substance having low volatility. As lactate is nontoxic to the human body, lactate is used as a flavoring agent, an acidifier, and a preservative. In addition, lactate is a raw material of polylactic acid (PLA), which is an environment-friendly alternative polymer substance and a biodegradable plastic.

An organic acid is separated into a hydrogen ion and an anion of the organic acid under pH conditions higher than a pKa value of the organic acid, for example, under neutral conditions. However, an organic acid, for example, lactate, exists as a free acid having no electromagnetic force under conditions wherein the pH is lower than the pKa value of the organic acid. Since an anion form may not penetrate a cell membrane, while a free acid form may penetrate a cell membrane, an organic acid outside a cell membrane may be introduced to the inside of a cell in an environment where a concentration of an organic acid is high, and thus an intracellular pH may be decreased. In addition, an organic acid in the form of an anion existing under conditions where the acidity is higher than the pKa value of the organic acid exists in the form of a salt during cell culturing or fermentation by adding a salt such as a neutralizing agent, and then the organic acid is separated from the produced salt form. As a result, a cell lacking acid resistance may lose cellular activity under acidic conditions including lactate and then die.

Therefore, there is a need for not only a microorganism having acid resistance but also a microorganism that is resistant to stresses such as osmotic pressure.

SUMMARY

Provided is a yeast cell having stress tolerance, wherein the yeast cell is genetically engineered to have enhanced MSN2 activity in comparison to a parent cell.

Also provided is a method of preparing a yeast cell having enhanced stress tolerance, wherein the method includes increasing expression of MSN2 in the yeast cell.

Further provided is a method of producing lactate by using the yeast cell.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
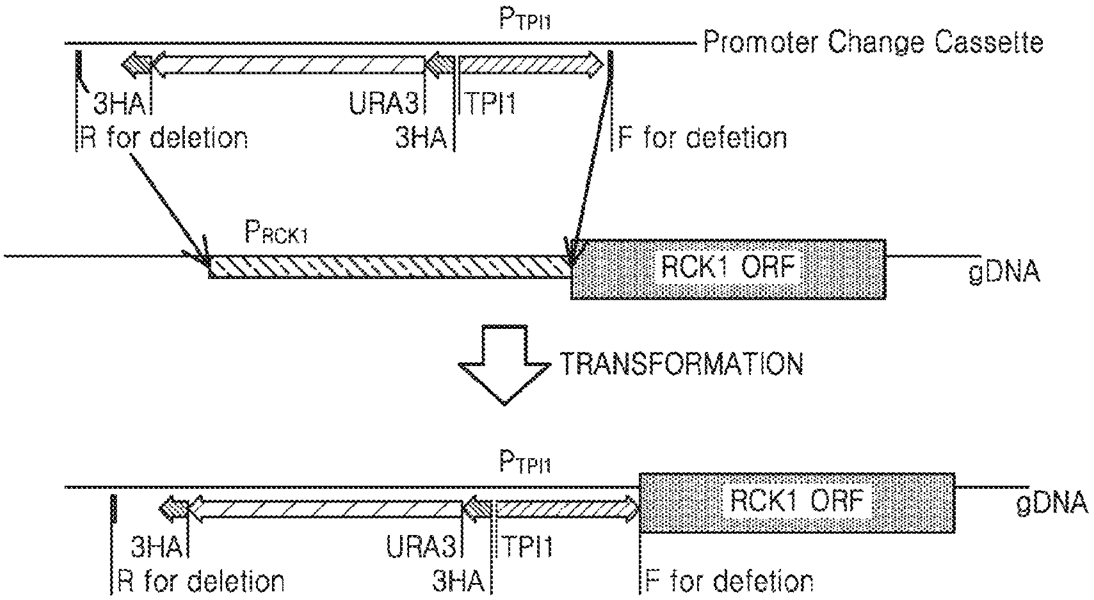
FIG. 1 is a schematic depicting a procedure of preparing a *S. cerevisiae* CEN.PK2-1 D strain into which a vector was inserted, wherein an RCK 1 gene promoter was substituted in the vector.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present disclosure. As used herein, the term "and/or" includes any and all combinations of one or more of the associated listed items. Expressions such as "at least one of," when preceding a list of elements, modify the entire list of elements and do not modify the individual elements of the list.

The terms "activity increase", "increased activity" or "enhanced activity" of an enzyme, a polypeptide, or a protein used herein may refer to an increase in activity of an enzyme, a polypeptide, or a protein sufficient to detect and means that the activity level of a cell or an isolated polypeptide is higher than an activity level measured in a comparable cell of the same kind (e.g., parent cell) or the original polypeptide. In other words, the term may refer to an activity of a genetically engineered polypeptide, or polypeptide of a genetically engineered cell, which is increased by about 5%, about 10%, about 15%, about 20%, about 30%, about 50%, about 60%, about 70%, about 100%, about 200% or about 300% in comparison with the same biological activity of the original polypeptide which is not genetically engineered, or the activity of the polypeptide in a cell that is not genetically engineered (e.g., a parent cell or "wild-type" cell). A polypeptide having an increased activity may be verified by using a method known to those of ordinary skill in the art.

The activity increase of a polypeptide may be achieved by an expression increase or an increase in specific activity of a polypeptide. The expression increase may be caused by introduction of a polynucleotide encoding the polypeptide into a cell, by an increase in the copy number of a polynucleotide encoding the polypeptide in a cell, or by mutation of a regulatory region of a polynucleotide encoding the polypeptide in a cell. The mutation of a regulatory region of the polynucleotide may include a modification of an expression regulatory sequence of a gene. The expression regulatory sequence may be a promoter sequence or a transcription terminator sequence for expression of the gene. In addition, the regulatory sequence may be a sequence encoding a motif that may affect gene expression. The motif may be, for example, a secondary structure-stabilization motif, a RNA destabilization motif, a splice-activation motif, a polyadenylation motif, an adenine-rich sequence, or an endonuclease recognition site.

A polynucleotide whose copy number is increased may be endogenous or exogenous. The endogenous gene refers to a gene which has already existed in a genetic material included in a microorganism. The exogenous gene refers to a gene which is introduced to a host cell by a method such as integration to a host cell genome. An introduced gene may be homologous or heterologous with the host cell.

The term "copy number increase" may be an increase in the copy number by the introduction of an exogenous gene or amplification of an endogenous gene, and may include causing, by genetic engineering, a cell to have a gene which is not preexisting in the cell. The introduction of a gene may be mediated by a vehicle such as a vector. The introduction may be a transient introduction in which the gene is not integrated to a genome, or insertion of the gene into a genome. The introduction may be performed, for example, by introducing to the cell a vector into which a polynucleotide encoding a target polypeptide is inserted, and then replicating the vector in the cell or integrating the polynucleotide into the genome.

The term "gene" refers to a nucleic acid fragment expressing a specific protein and may include a coding region as well as regulatory sequences such as a 5'-non coding sequence or a 3'-non coding sequence. The regulatory sequences may include a promoter, an enhancer, an operator, a ribosome binding site, a polyA binding site, and a terminator region.

The term "heterologous" means "foreign," or "not native," and refers to a molecule or activity derived from a source other than the referenced species, whereas "homologous" refers to a molecule or activity native to the host parent cell or preexisting in the host cell.

The term "secretion" means transport of a material from the inside of a cell to a periplasmic space or an extracellular environment.

The term "organic acid" used herein refers to not only neutral organic acids but also negatively charged organic acids and salts thereof, interchangeably. The organic acids may include acetic acid, lactic acid, pyruvate, and TCA cycle intermediate such as citric acid, itaconic acid, isocitric acid, oxalosuccinic acid, α-ketoglutaric acid, succinic acid, succinyl-CoA, fumaric acid, maleic acid, or oxaloacetic acid. For example, acetic acid is interchangeably used with acetate or a salt thereof.

The term "activity decrease" or "decreased activity" of an enzyme or a polypeptide as used herein means that the activity level of an enzyme or polypeptide in a genetically engineered cell or an isolated genetically engineered enzyme or a polypeptide is lower than the same kind of activity level measured in a comparable cell of the same kind without the genetic engineering, e.g., a parent cell or "wild-type" cell, or the original non-genetically engineered polypeptide or that no activity is shown. In other words, the term may refer to an activity of a genetically engineered polypeptide, or polypeptide of a genetically engineered cell, which is decreased by about 10%, about 20%, about 30% or more, about 40% or more, about 50% or more, about 55% or more, about 60% or more, about 70% or more, about 75% or more, about 80% or more, about 85% or more, about 90% or more, about 95% or more, or about 100% in comparison with the same biological activity of the original polypeptide which is not genetically engineered, a polypeptide of a cell which is not genetically engineered, a polypeptide of a parent cell, or a wild-type polypeptide. A polypeptide having a decreased activity may be verified by using a method known to those of ordinary skill in the art. The activity decrease includes the case where an enzyme is expressed but there is no enzyme activity or enzyme activity is decreased, or the case where a gene encoding an enzyme is not expressed or, even when the gene is expressed, the expression is lower than the expression of a gene encoding a polypeptide that is not genetically engineered or a gene encoding a wild-type polypeptide.

The decrease of an enzyme may be caused by a deletion or disruption of a gene encoding the enzyme. The terms "deletion", "disruption" and "removed" used herein refers to mutation, substitution, or deletion of a part of or the whole gene or a part of or the whole regulatory region such as a promoter or a terminator of a gene, or insertion of at least one base group into a gene for preventing a gene from expression or for preventing an expressed enzyme from showing activity or making an expressed enzyme show a decreased activity level. The deletion or disruption of the gene may be achieved by gene manipulation such as homogenous recombination, mutation generation, or molecule evolution. When a cell includes a plurality of the same genes or at least two different polypeptide paralogous genes, one or more genes may be deleted or disrupted.

The term "sequence identity" of a nucleic acid or a polypeptide used herein refers to a degree of similarity of base groups or amino acid residues between two aligned sequences, when the two sequences are aligned to match each other as possible, at corresponding positions. The sequence identity is a value that is measured by aligning the two sequences to an optimum state and comparing the two sequences at a particular comparing region, wherein a part of the sequence within the particular comparing region may be added or deleted compared to a reference sequence. A sequence identity percentage may be calculated, for example, by comparing the two sequences aligned within the whole comparing region to an optimum; obtaining the number of matched locations by determining the number of locations represented by the same amino acids of nucleic acids in both of the sequences; dividing the number of the matched locations by the total number of the locations within the comparing region (i.e., a range size); and obtaining a percentage of the sequence identity by multiplying the result by 100. The sequence identity percent may be determined by using a common sequence comparing program, for example, BLASTN or BLASTP (NCBI), CLC Main Workbench (CLC bio), MegAlign™ (DNASTAR Inc).

In confirming many different polypeptides or polynucleotides having the same or similar function or activity, sequence identities at several levels may be used. For example, the sequence identities may include about 50% or greater, about 55% or greater, about 60% or greater, about 65% or greater, about 70% or greater, about 75% or greater, about 80% or greater, about 85% or greater, about 90% or greater, about 95% or greater, about 96% or greater, about 97% or greater, about 98% or greater, about 99% or greater, or 100%.

The term "parent cell" used herein may refer to a cell that does not have a specific genetic modification of a genetically engineered cell. The term "wild-type" polypeptide or polynucleotide or cell may refer to a polypeptide or polynucleotide or cell that does not have a specific genetic modification. A parent cell may be a cell that is not genetically engineered to have enhanced (increased) MSN2 activity. The parent cell may be a parent strain that is used to genetically engineer a cell to have enhanced MSN2 activity. Thus, the parent cell may be genetically identical to the genetically engineered cell except for the particular genetic mutations that result in the genetically engineered cell. The parent cell may be a cell that does not have a genetic modification to enhance (increase) MSN2 activity.

The term "lactate" used herein is interpreted to include not only lactic acid itself but also an anion form, a salt, a solvate, a polymorph of lactic acid, or a combination thereof. The salt may be, for example, an inorganic acid salt, an organic acid salt, or a metal salt. An inorganic acid salt may be a hydrochloric acid salt, a bromic acid salt, a phosphoric acid salt, a sulfuric acid salt, or a disulfuric acid salt. An organic acid salt may be a formic acid salt, a citric acid salt, an acetic acid salt, a propionic acid salt, a lactic acid salt, a oxalic acid salt, a tartatic acid salt, a malic acid salt, a maleic acid salt, a citric acid salt, a fumaric acid salt, a besylic acid, a camsylic acid salt, an edisyl salt, a trifluoroacetic acid salt, a bezoic acid salt, a gluconic acid salt, a methanesulphonic acid, a glycolic acid salt, a succinic acid salt, a 4-toluenesulfonic acid salt, a galacturonic acid, an embonic acid salt, a glutamic acid salt, or a aspartic acid salt. A metal salt may be a calcium salt, a sodium salt, a magnesium salt, a strontium salt, or a potassium salt.

Provided is a stress resistant yeast cell that is genetically engineered to have enhanced MSN2 activity in comparison with a cell that is not genetically engineered (e.g., a parent cell).

MSN2 may have an about 60% or more, about 70% or more, about 80% or more, about 90% or more, about 95% or more, about 96% or more, about 97% or more, about 98% or more, or about 99% or more amino acid sequence identity with a sequence of SEQ ID NO: 1. The MSN2 gene may have a polynucleotide sequence encoding a protein having a 95% or more sequence identity with SEQ ID NO: 1 or a nucleotide sequence of SEQ ID NO: 2. For example, the MSN2 gene may have a nucleotide sequence of SEQ ID NO: 2.

Regarding the stress-resistant yeast cell, the stress may be osmotic pressure. Thus, the yeast cell may have resistance to osmotic pressure. The yeast cell may have improved intracellular osmotic pressure of the yeast cell under extracellular osmotic pressure of the yeast cell. The yeast cell may contain an increased amount of glycerol in comparison with a parent cell. In addition, the yeast cell may contain an increased amount of trehalose in comparison with a parent cell. In addition, the yeast cell may have an increased expression of genes related to trehalose biosynthesis in comparison with a parent cell. The yeast cell may contain a modified amount of a specific fatty acid. The yeast cell may have a decreased amount of a specific fatty acid in comparison with a parent cell. The specific fatty acid may serve as a component of a cell membrane. The specific fatty acid may be an unsaturated fatty acid. The specific fatty acid may be hexadecenoic acid. The yeast cell may have a lower concentration of a specific fatty acid in comparison with a parent cell, and the cell membrane rigidity of the yeast cell may be increased by decreasing cell membrane fluidity. A yeast cell having a decreased amount of a specific fatty acid in comparison with a parent cell may have resistance to stresses such as acid or osmotic pressure.

In the stress-resistant yeast cell, stress may be acid. Thus, the yeast cell may have acid resistance. Acid resistance may refer to better growth under acidic conditions in comparison with a cell that is not genetically engineered. The acid conditions may be acidic conditions including an organic acid, an inorganic condition, or a combination thereof. The organic acid may be a C1 to C20 organic acid. The organic acid may be acetic acid, lactic acid, propionic acid, 3-hydroxypropionic acid, butyric acid, 4-hydroxybutyric acid, succinic acid, fumaric acid, malic acid, oaxalic acid, adipic acid, or a combination thereof. The yeast cell may grow better in a range from about pH 2.0 to about 7.0 less, for example, from about pH 2.0 to about 6.5, from about pH 2.0 to about 6.0, from about pH 2.0 to about 5.5, from about pH 2.0 to about 5.0, from about pH 2.0 to about 4.5, from about pH 2.0 to about 4.0, from about pH 2.0 to about 3.8, or from about pH 3.3 to about 3.8 in comparison with a yeast cell where MSN2 activity is not increased. The degree of growth may be measured by counting of microorganism colonies or measuring the optical density (OD) of the colonies. The yeast cell may have increased growth rate as measured by OD compared to that of a yeast cell in which msn2 activity is not increased.

In addition, acid resistance may refer to a higher survival rate under acidic conditions in comparison with a cell that is not genetically engineered (e.g., a parent cell). The acid conditions may be acidic conditions including an organic acid, an inorganic condition, or a combination thereof. The organic acid may be a C1 to C20 organic acid. The organic acid may be acetic acid, lactic acid, propionic acid, 3-hydroxypropionic acid, butyric acid, 4-hydroxybutyric acid, succinic acid, fumaric acid, malic acid, oaxalic acid, adipic acid, or a combination thereof. The yeast cell may survive better in a range from about pH 2.0 to about 7.0 less, for example, from about pH 2.0 to about 6.5, from about pH 2.0 to about 6.0, from about pH 2.0 to about 5.5, from about pH 2.0 to about 5.0, from about pH 2.0 to about 4.5, from about pH 2.0 to about 4.0, from about pH 2.0 to about 3.8, from about pH 2.5 to about 3.8, from about pH 3.0 to about 3.8, or from about pH 3.3 to about 3.8 in comparison with a yeast cell where MSN2 activity is not increased.

In addition, acid resistance may refer to an increased metabolizability under acidic conditions in comparison with a cell that is not genetically engineered. The acid conditions may be acidic conditions including an organic acid, an inorganic condition, or a combination thereof. The organic acid may be a C1 to C20 organic acid. The organic acid may be acetic acid, lactic acid, propionic acid, 3-hydroxypropionic acid, butyric acid, 4-hydroxybutyric acid, succinic acid, fumaric acid, malic acid, oxalic acid, adipic acid, or a combination thereof. The yeast cell may survive better in a range from about pH 2.0 to about 7.0 less, for example, from about pH 2.0 to about 6.5, from about pH 2.0 to about 6.0, from about pH 2.0 to about 5.5, from about pH 2.0 to about 5.0, from about pH 2.0 to about 4.5, from about pH 2.0 to about 4.0, from about pH 2.0 to about 3.8, from about pH 2.5 to about 3.8, from about pH 3.0 to about 3.8, or from about pH 3.3 to about 3.8 in comparison with a yeast cell where MSN2 activity is not increased. "Metabolizability" may be measured with reference to a nutrient absorption rate per cell, for example, a glucose absorption rate per cell. Alternatively, "metabolizability" may be measured with reference to a product emission rate per cell, for example, a carbon dioxide emission rate per cell.

The terms "acid-resistant", "acid-tolerant", "acid tolerating", "acid-resistance", and "acid tolerance" may be used interchangeably.

The yeast cell may be a strain belonging to *Saccharomyces, Zygosaccharomyces, Pichia, Kluyveromyces, Candida, Shizosaccharomyces, Issachenkia*, or *Hansenula*. A strain belonging to *Saccharomyces* may be, for example, *S. cerevisiae, S. bayanus, S. boulardii, S. bulderi, S. cariocanus, S. cariocus, S. chevalieri, S. dairenensis, S. ellipsoideus, S. eubayanus, S. exiguus, S. florentinus, S. kluyveri, S. martiniae, S. monacensis, S. norbensis, S. paradoxus, S. pastorianus, S. spencerorum, S. turicensis, S. unisporus, S. uvarum*, or *S. zonatus*.

The enhanced MSN2 activity may be due to a copy number increase of a gene encoding the MSN2, or modification of an expression regulatory sequence of the gene. The copy number increase may be achieved by introduction of an exogenous gene into the cell, or by amplification of an endogenous gene. The introduction of a gene may be mediated by a vehicle such as a vector. The introduction may be a transient introduction in which the gene is not integrated to a genome or insertion of the gene into a genome. The introduction may be performed, for example, by introducing to the cell a vector into which a polynucleotide encoding a target polypeptide is inserted, and then replicating the vector in the cell or integrating the polynucleotide into the genome. The gene may be operably linked with a regulatory sequence related to regulation of the gene expression (i.e. an expression regulatory sequence). The (expression) regulatory sequence may include a promoter, a 5'-non coding sequence, a 3'-non coding sequence, a transcription terminator sequence, an enhancer, or a combination thereof. The gene may be an endogenous gene or an exogenous gene. In addition, the regulatory sequence may be a sequence encoding a motif that may affect gene expression. The motif may be, for example, a secondary structure-stabilization motif, a RNA destabilization motif, a splice-activation motif, a polyadenylation motif, an adenine-rich sequence, or an endonuclease recognition site. The MSN2 activity increase may be due to a mutation of a gene encoding the MSN2. Mutation may cause substitution, insertion, addition, or conversion of at least one base.

The yeast cell may be capable of producing lactate. The yeast cell may have activity of a polypeptide converting pyruvate to lactate. The yeast cell may include a gene encoding a polypeptide converting pyruvate to lactate. The yeast cell may have increased activity of a polypeptide converting pyruvate to lactate. The polypeptide converting pyruvate to lactate may be lactate dehydrogenase (LDH). The LDH may be an NAD(P)-dependent enzyme. The LDH may be stereo-specific, and thus produce only L-lactate, or only D-lactate, or both L-lactate and D-lactate. The NAD(P)-dependent enzyme may be an enzyme classified as EC 1.1.1.27 acting on L-lactate or EC 1.1.1.28 acting on D-lactate.

The yeast cell capable of producing lactate may have increased activity of LDH. The yeast cell may include at least one polynucleotide encoding LDH, and the gene may be exogenous. The polynucleotide encoding LDH may be derived from bacteria, yeast, fungi, mammals, or reptiles. The polynucleotide may encode LDH of at least one selected from *Pelodiscus sinensis japonicus, Ornithorhynchus anatinus, Tursiops truncatus, Rattus norvegicus*, and *Xenopus laevis*. The LDH derived from *Pelodiscus sinensis japonicus*, the LDH derived from *Ornithorhynchus anatinus*, the LDH derived from *Tursiops truncatus*, and the LDH derived from *Rattus norvegicus* may include an amino acid sequence having an about 60% or more, about 70% or more, about 80% or more, about 90% or more, about 95% or more, about 96% or more, about 97% or more, about 98% or more, or about 99% or more sequence identity with an amino acid sequence of SEQ ID NOS: 3, 4, 5, 6, and 7, respectively. For example, the polynucleotide encoding LDH may be a polynucleotide encoding an amino acid having an about 95% or more sequence identity with an amino acid sequence of SEQ ID NOS: 3, 4, 5, 6, and 7. In addition, a polynucleotide encoding the LDH may be a polynucleotide encoding an amino acid having an about 95% or more sequence identity with an amino acid sequence of SEQ ID NOS: 3, 4, 5, 6, and 7, or a polynucleotide sequence of SEQ ID NOS: 8 or 9.

The polynucleotide encoding LDH may be included in a vector. The vector may include a replication origin, a promoter, a polynucleotide encoding a lactate dehydrogenase, and a terminator. The replication origin may include a yeast autonomous replication sequence (ARS). The yeast ARS may be stabilized by a yeast centrometric sequence (CEN). The promoter may be selected from the group consisting of a CYC promoter, a TEF promoter, a GPD promoter, and an ADH promoter. The CYC promoter, TEF promoter, GPD promoter, and ADH promoter may, each respectively, have nucleotide sequences of SEQ ID NOS: 27, 28, 29, 30, and 31. The terminator may be selected from the group consisting of phosphoglycerate kinase 1 (PGK1), cytochrome c transcription (CYC1), and GAL1. The CYC1 terminator may have a nucleotide sequence of SEQ ID NO: 32. The vector may further include a selection marker. A polynucleotide encoding LDH may be included at a specific site of a genome of a yeast cell. The specific site may include a locus of a gene to be removed or disrupted, such as PDC or CYB2. When a polynucleotide encoding lactate dehydrogenase functions for production of active proteins in a cell, the polynucleotide is considered "functional" in a cell.

The yeast cell may include a polynucleotide that encodes one LDH or polynucleotides that encode a plurality of copies of LDH having a copy number from about 2 to about 10. The yeast cell may include polynucleotides that encode LDH having a copy number, for example, from about 1 to about 8, from about 1 to about 7, from about 1 to about 6, from about 1 to about 5, from about 1 to about 4, or from about 1 to about 3. When the yeast cell includes the polynucleotides that encode a plurality of copies of LDH, respective polynucleotides may be a combination of polynucleotides encoding the same LDH or encoding at least two different LDHs. A plurality of copies of a polynucleotide encoding exogenous LDH may be included in the same locus or in multiple loci within a host cell's genome, and promoters or terminators of respective copies may be the same or different.

In addition, the yeast cell may be capable of producing lactate. In the yeast cell, the activity of a pathway disturbing a flow of metabolites to lactate may be inactivated or decreased. In addition, in the yeast cell, the activity of a pathway facilitating or helping a flow of metabolites to lactate may be increased.

In the yeast cell, activity of a polypeptide converting pyruvate to acetaldehyde, a polypeptide converting lactate to pyruvate, a polypeptide converting dihydroxy acetone phosphate (DHAP) to glycerol-3-phosphate, a polypeptide converting acetaldehyde to ethanol, aldehyde dehydrogenase, or a combination thereof may be decreased.

In the yeast cell, a gene encoding a polypeptide converting pyruvate to acetaldehyde may be removed (deleted) or disrupted. A polypeptide converting pyruvate to acetaldehyde may be an enzyme classified as EC 4.1.1.1. The polypeptide converting pyruvate to acetaldehyde may be, for example, pyruvate decarboxylase (PDC). The PDC may be PDC1, PDC5, or PDC6. The polypeptide converting pyruvate to acetaldehyde may have an amino acid sequence having an about 60% or more, about 70% or more, about 80% or more, about 90% or more, about 95% or more, about 96% or more, about 97% or more, about 98% or more, about 99% or more sequence identity with an amino acid sequence of SEQ ID NO: 10. A gene encoding the polypeptide converting pyruvate to acetaldehyde may have a polynucleotide sequence encoding an amino acid sequence having an about 95% or more sequence identity with an amino acid sequence of SEQ ID NO: 10 or a polynucleotide sequence of SEQ ID NO: 11. The gene may be pdc1, pdc5, or pdc6.

In the yeast cell, activity of a polypeptide converting lactate to pyruvate may be removed (deleted) or disrupted. The polypeptide converting lactate to pyruvate may be a cytochrome c-dependent enzyme. The polypeptide converting lactate to pyruvate may be an enzyme classified as EC 1.1.2.4 acting on L-lactate or EC 1.1.2.3 acting on D-lactate. The polypeptide converting lactate to pyruvate may be lactate cytochrome-c oxidoreductase, CYB2 (CAA86721.1), CYB2A, CYB2B, DLD1, DLD2, or DLD3. The polypeptide converting lactate to pyruvate may have an amino acid sequence having an about 60% or more, about 70% or more, about 80% or more, about 90% or more, about 95% or more, about 96% or more, about 97% or more, about 98% or more, about 99% or more sequence identity with an amino acid sequence of SEQ ID NO: 12. A gene encoding the polypeptide converting lactate to pyruvate may have a polynucleotide sequence encoding an amino acid sequence having an about 95% or more sequence identity with an amino acid sequence of SEQ ID NO: 12 or a polynucleotide sequence of SEQ ID NO: 13. The gene may be cyb2, cyb2a, cyb2b, dld1, dld2, or dld3.

In the yeast cell, a gene encoding a polypeptide converting DHAP to glycerol-3-phosphate may be removed (deleted) or disrupted. The polypeptide converting DHAP to glycerol-3-phosphate may be cytosolic glycerol-3-phosphate dehydrogenase, or an enzyme catalyzing conversion of DHAP to glycerol-3-phosphate by using oxidation of NADH or NADP to $NAD^+$ or $NADP^+$. The polypeptide may belong to EC 1.1.1.8. The cytosolic glycerol-3-phosphate dehydrogenase may be GPD1 or GPD2. The cytosolic glycerol-3-phosphate dehydrogenase may have an amino acid sequence having an about 60% or more, about 70% or more, about 80% or more, about 90% or more, about 95% or more, about 96% or more, about 97% or more, about 98% or more, about 99% or more sequence identity with an amino acid sequence of SEQ ID NO: 14. A gene encoding cytosolic glycerol-3-phosphate dehydrogenase may have a polynucleotide sequence encoding an amino acid sequence having an about 95% or more sequence identity with an amino acid sequence of SEQ ID NO: 14 or a polynucleotide sequence of SEQ ID NO: 15.

In the yeast cell, a gene encoding a polypeptide converting acetaldehyde to ethanol may be removed (deleted) or disrupted. The polypeptide may be an enzyme catalyzing conversion of acetaldehyde to ethanol. The polypeptide may belong to EC 1.1.1.1. The polypeptide may be an enzyme catalyzing conversion of acetaldehyde to ethanol by using conversion of NADH to $NAD^+$. The polypeptide may be an alcohol dehydrogenase (Adh), for example, Adh1, Adh2, Adh3, Adh4, Adh5, Adh6, or Adh7. The polypeptide may have an amino acid sequence having an about 60% or more, about 70% or more, about 80% or more, about 90% or more, about 95% or more, about 96% or more, about 97% or more, about 98% or more, about 99% or more sequence identity with an amino acid sequence of SEQ ID NO: 16. A gene encoding the polypeptide may have a polynucleotide sequence encoding an amino acid sequence having an about 95% or more sequence identity with an amino acid sequence of SEQ ID NO: 16 or a polynucleotide sequence of SEQ ID NO: 17. The gene may be, for example, adh1, adh2, adh3, adh4, adh5, adh6, or adh7.

In the yeast cell, a gene encoding aldehyde dehydrogenase (ALD) may be removed (deleted) or disrupted. The ALD may belong to EC.1.2.1.4. The ALD may be ALD6. ALD6 may encode a constitutive cytosolic form for ALD. ALD6 may be activated by $Mg^{2+}$ and be specific to NADP. The enzyme may be involved in production of acetate. Cystolic acetyl-CoA may be synthesized from the produced acetate. The ALD may have an amino acid sequence having an about 60% or more, about 70% or more, about 80% or more, about 90% or more, about 95% or more, about 96% or more, about 97% or more, about 98% or more, about 99% or more sequence identity with an amino acid sequence of SEQ ID NO: 18. A gene encoding the ALD may have a polynucleotide sequence encoding an amino acid sequence having an about 95% or more sequence identity with an amino acid sequence of SEQ ID NO: 18 or a polynucleotide sequence of SEQ ID NO: 19. The gene may be, for example, ald2, ald3 or ald6.

The yeast cell may have activity of converting acetaldehyde to acetyl-CoA or include an exogenous gene encoding a polypeptide converting acetaldehyde to acetyl-CoA. The yeast cell may have increased activity of converting acetaldehyde to acetyl-CoA. The polypeptide converting acetaldehyde to acetyl-CoA may be "acetaldehyde dehydrogenase (acetylating)" or "acetaldehyde:NAD+ oxidoreductase (CoA-acetylating)." In addition, the polypeptide converting acetaldehyde to acetyl-CoA may be classified as EC 1.2.1.10. The polypeptide may catalyze a reversible reaction from acetaldehyde+coenzyme A+$NAD^+$ to acetyl-CoA+NADH. The polypeptide may be acylating acetaldehyde dehydrogenase (A-ALD). An example of the A-ALD may be an E. coli-derived MhpF or a functional homologue, for example, an E. coli-derived or *S. typhimurium*-derive EutE (for example, an EutE gene having a nucleotide sequence of SEQ ID NO: 87 and an EutE protein having an amino acid sequence of SEQ ID NO: 88), or *Pseudomonas* sp. CF600-derived dmpF. In *E. coli*, the A-ALD gene, which is mhpF, may be one of mhpA, mhpB, mhpC, mhpD, mhpE, and mhpF transcription units. Generally, MhpE and MhpF exist as one complex in other microorganisms, but MhpF may exist alone in *E. coli*, and show activity. The polypeptide converting acetaldehyde to acetyl-CoA may have an amino acid sequence having an about 60% or more, about 70% or more, about 80% or more, about 90% or more, about 95% or more, about 96% or more, about 97% or more, about 98% or more, about 99% or more sequence identity with an amino acid sequence of SEQ ID NO: 18. The MhpF may have, for example, an amino acid of SEQ ID NO: 20. A gene encoding the polypeptide may be a polynucleotide sequence encoding a protein sequence having an about 95% or more sequence identity with an amino acid sequence of SEQ ID NO: 18 or a polynucleotide having an about 95% or more sequence identity with a polynucleotide sequence of SEQ ID NO: 21. A-ALD exogenous gene may be altered as appropriate for expression in a yeast cell (e.g., the sequence may be codon optimized for expression in yeast), provided the amino acid sequence of the encoded protein does not change. For example, the gene modified to be adaptable to a yeast cell may have a polynucleotide sequence of SEQ ID NO: 22.

The exogenous gene may be introduced to a parent cell through an expression vector. In addition, the exogenous gene may be introduced to a parent cell in a form of a linear polynucleotide. In addition, the exogenous gene may be expressed in a cell from an expression vector (e.g., a plasmid). In addition, the exogenous gene may be expressed by being inserted into an intracellular genetic material (e.g., a chromosome) for stable expression. In addition, the exogenous gene may be appropriately regulated by an exogenous promoter operably linked to the gene. The promoter may be a promoter derived from ccw12, pdc1, tef1, or pgk1 gene.

In the yeast cell, activity of radiation sensitivity complementing kinase may be increased. In addition, the yeast cell may be obtained by increasing expression or specific activity of radiation sensitivity complementing kinase. The expression increase may be by introduction or copy number increase of a polynucleotide encoding radiation sensitivity complementing kinase or by mutation of a regulatory region of the polynucleotide. The radiation sensitivity complementing kinase may be serine/threonine-protein kinase. The kinase may be an enzyme belonging to EC 2.7.11.1. The radiation sensitivity complementing kinase may be RCK1 or RCK2. The radiation sensitivity complementing kinase may have an amino acid sequence having an about 60% or more, about 70% or more, about 80% or more, about 90% or more, about 95% or more, about 96% or more, about 97% or more, about 98% or more, or about 99% or more sequence identity with an amino acid sequence of SEQ ID NO: 23 or 24. For example, RCK1 and RCK2 may have amino acid sequences of SEQ ID NOS: 23 and 24, respectively. The radiation sensitivity complementing kinase may have a polynucleotide sequence encoding a protein having an about 95% or more sequence identity with SEQ ID NO: 23 or 24, or a polynucleotide sequence of SEQ ID NO: 23 or 24. For example, rck1 and rck2 genes may have polynucleotide sequences of SEQ ID NOS: 25 and 26, respectively.

In addition, for example, the yeast cell may be a yeast cell where MSN2 activity is increased in comparison with a parent cell; a gene encoding a polypeptide converting pyruvate to acetaldehyde, a gene encoding a polypeptide converting lactate to pyruvate, a gene encoding a polypeptide converting DHAP to glycerol-3-phosphate, or a combination thereof is removed (deleted) or disrupted; and a gene encoding a polypeptide converting pyruvate to lactate is included or further introduced. The yeast cell may be *S. cerevisiae*. The yeast cell may have an accession number of KCTC 12415 BP.

Also provided is a composition for producing lactate, wherein the composition includes the yeast cell. The composition may further comprise components useful for producing lactate, such as a cell culture medium, carbon source (e.g., glucose), and other components used for cell culture.

Further provided is a method of preparing a stress-resistant yeast cell (e.g., a cell having an enhanced (increased) stress tolerance), wherein the method includes over-expressing (e.g., increasing the expression) MSN2 in the yeast cell. The yeast cell and stress conditions are described above. Over-expression refers to an increased expression level of a specific gene in comparison with an expression level of the specific gene in a parent cell. The parent cell is described above. The expression of MSN2 can be increased by any suitable method, as described herein, such as by increasing the copy number of a polynucleotide encoding MSN2, or by modifying an expression regulatory sequence of a gene encoding MSN2. For instance, the expression of MSN2 can be increased by introducing into the yeast cell an exogenous polynucleotide that encodes MSN2; by providing a heterologous promoter operatively linked to a polynucleotide encoding MSN2, or both. All other aspects of the method are as described with respect to the genetically engineered yeast cell.

Still further provided is a method of producing lactate, wherein the method includes culturing the yeast cell in an appropriate culture medium. The yeast cell is as described herein.

The culturing may be performed in a suitable medium under suitable culturing conditions known in the art. One of ordinary skill in the art may suitably change a culture medium and culturing conditions according to the microorganism selected. A culturing method may be batch culturing, continuous culturing, fed-batch culturing, or a combination thereof. The microorganism may secrete acrylate to outside the cell.

The culture medium may include various carbon sources, nitrogen sources, and trace elements.

The carbon source may include, for example, one or more carbohydrates such as glucose, sucrose, lactose, fructose, maltose, starch, or cellulose; fat such as soybean oil, sunflower oil, castor oil, or coconut oil; fatty acid such as palmitic acid, stearic acid, linoleic acid; alcohol such as glycerol or ethanol; organic acid such as acetic acid, or a combination thereof. The culturing may be performed by having glucose as the carbon source. The nitrogen source may be an organic nitrogen source such as peptone, yeast extract, beef stock, malt extract, corn steep liquor (CSL), or soybean flour, or an inorganic nitrogen source such as urea, ammonium sulfate, ammonium chloride, ammonium phosphate, ammonium carbonate, and ammonium nitrate, or a combination thereof. The culture medium is a supply source of phosphorus and may include, for example, potassium dihydrogen phosphate, dipotassium phosphate, and corresponding sodium-containing salt thereof, and a metal salt such as magnesium sulfate or iron sulfate. Also, an amino acid, vitamin, suitable precursor, or the like may be included in the culture medium. The culture medium or individual component may be added to a culture medium solution in a batch, fed-batch, or continuous manner.

In addition, pH of the culture medium solution may be adjusted by adding a compound such as ammonium hydroxide, potassium hydroxide, ammonia, phosphoric acid, and sulfuric acid to the culture medium solution by using a suitable method during the culturing process. In addition, an antifoaming agent such as fatty acid polyglycol ester may be used during the culturing process to inhibit the generation of bubbles.

The cell may be cultured under aerobic, microaerobic, or anaerobic conditions. The microaerobic conditions refer to culture conditions under which oxygen of a level lower than an atmospheric oxygen level is dissolved into a culture medium. The lower level of oxygen may be, for example, from about 0.1% to about 10%, from about 1% to about 9%, from about 2% to about 8%, from about 3% to about 7%, or from about 4% to about 6% of atmospheric saturation concentration of dissolved oxygen. In addition, microaerobic conditions may be, for example, a dissolved oxygen concentration of from about 0.9 ppm to about 3.6 ppm in a culture medium. A culturing temperature may be, for example from about 20° C. to about 45° C. or from about 25° C. to about 40° C. A culturing duration may continue until a target lactate is obtained in a desired amount. The method of producing lactate may include recovering or separating lactate from a culture solution.

Recovering of lactate from a culture solution may be performed by any separation and purification methods known in the art. The recovering may be performed by centrifugation, ion-exchange chromatography, filtration, precipitation, extraction, distillation, or a combination thereof. For example, a culture solution may be centrifugated to remove biomass, and a resulting supernatant may be separated by ion-exchange chromatography.

Hereinafter, the present disclosure will be described in further detail with reference to examples. However, these examples are for illustrative purposes only and are not to be construed as limiting the scope of the present disclosure.

Example 1

Preparation of Yeast Cell Having Improved Lactate Productivity

1. Preparation of Yeast Cell Having Improved Lactate Productivity

To improve lactate productivity in *S. cerevisiae* CEN.PK2-1D, a gene encoding an enzyme involved in a pathway from pyruvate to ethanol, which is a pathway making metabolites flow in directions except a direction toward lactate, was deleted, wherein the gene encodes pyruvate decarboxylase 1 (PDC1) and alcohol dehydrogenase 1 (ADH1). PDC1 is an enzyme catalyzing a reaction of converting pyruvate to acetaldehyde and $CO_2$. ADH1 is an enzyme catalyzing a reaction of converting acetaldehyde to ethanol.

At the same time when the pdc1 gene and the adh1 gene were deleted, lactate dehydrogenase (ldh) was respectively introduced. LDH is an enzyme catalyzing a reaction of converting pyruvate to lactate.

In addition, a gene encoding L-lactate cytochrome-c oxidoreductase (cyb2) which catalyzes a reaction of converting lactate to pyruvate was deleted. At the same time when the cyb2 gene was deleted, lactate dehydrogenase (ldh) gene was introduced.

In addition, to strengthen the metabolic flow of pyruvate in glycolysis, a gene encoding glycerol-3-phosphate dehydrogenase 1 (gpd1) having the activity of catalyzing a reaction of converting dihydroxy acetone phosphate (DHAP) to glycerol-3-phosphate (G3P) was deleted. GPD1 converts NADH to $NAD^+$ simultaneously with the reaction. At the same time when the gpd1 gene was deleted, a lactate dehydrogenase (ldh) gene was introduced.

In addition, a gene encoding an *E. coli*-derived MhpF (acetaldehyde dehydrogenase (acylating)) was introduced to *S. cerevisiae* CEN.PK2-1 D. MhpF may belong to EC.1.2.1.10. MhpF may be an enzyme catalyzing conversion of acetaldehyde to acetyl-CoA. MhpF may use $NAD^+$ and coenzyme A. MhpF may be the last enzyme of a meta-cleavage pathway for degradation of 3-HPP. A MhpF gene may be introduced to the site of an ald6 gene, which is a gene encoding aldehyde dehydrogenase 6 (ALD6) to delete the ald6 gene. The ald6 gene may encode a constitutive cytosolic form of aldehyde dehydrogenase. ALD6 may be activated by $Mg^{2+}$ and be specific to NADP. The enzyme may involve in production of acetate. Cytoplasmic acetyl-CoA may be synthesized from the produced acetate.

In addition, a gene encoding *S. cerevisiae*-derived RCK1 was introduced to *S. cerevisiae* CEN.PK2-1 D.

(1) Preparation of *S. cerevisiae* CEN.PK2-1D (Δ pdc1::ldh)

(1.1) Preparation of Vector for Deleting pdc1 and Introducing ldh

To block a pathway from pyruvate to acetaldehyde and then to ethanol in *S. cerevisiae* CEN.PK2-1D, a gene encoding pyruvate decarboxylase1 (pdc1) was removed. To express an Ldh derived from *Pelodiscus sinensis japonicus* at the same time as when the pdc1 gene was removed, the pdc1 gene was substituted with a 'ldh cassette' to delete the pdc1 gene. Unless otherwise described, the term "cassette" refers to a unit sequence to which a promoter, an encoding sequence, and a terminator were operably linked to express a protein.

Specifically, to prepare a vector including the 'ldh cassette,' a CCW12 promoter sequence (SEQ ID NO: 31) and an 'ldh gene (SEQ ID NO: 8)' obtained by performing a PCR using a genomic DNA of *S. cerevisiae* as a template, and a primer pair of SEQ ID NOS: 33 and 34 as primers were digested by using SacI/XbaI and BamHI/SalI, respectively, and then linked to a pRS416 vector (ATCC87521) digested by using the same enzymes. The pRS416 vector is a yeast centromere shuttle plasmid having a T7 promoter, ampicilin resistance in bacteria, a URA3 cassette (selection marker) in yeast, and a restriction enzyme cloning site. Next, a 'HPH cassette' sequence (SEQ ID NO: 37), which was an amplification product obtained by performing a PCT using a pCEP4 plasmid (Invitrogen, Cat. no. V044-50) as a template and a primer pair of SEQ ID NOS: 35 and 36 as primers, was digested by using SacI and linked to the obtained vector digested by using the same enzyme to prepare a p416-ldh-HPH vector including the 'ldh cassette.' A pCEP4 plasmid is an episomal mammalian expression vector using a cytomegalovirus (CMV) immediate-early enhancer/promoter for a high level of transcription of a recombinant gene inserted into a multiple cloning site. pCEP4 has a hygromycin B resistance gene for stable selection in a transfected cell. The 'ldh cassette' refers to a region including an ldh gene and a regulatory region thereof to express the ldh gene. The ldh gene was transcribed under a CCW12 promoter. In addition, the 'HPH (hygromycin B phosphotransferase) cassette' refers to a region including a hygromycin B resistance gene and a regulatory region thereof to express a hygromycin B resistance gene.

To prepare a vector for deleting pdc1, an ldh gene fragment and a pUC57-Ura3HA vector (DNA2.0 Inc.; SEQ ID NO: 40) prepared by performing a PCR using p416-ldh-HPH as a template and a primer set of SEQ ID NOS: 38 and 39 as primers were respectively digested by using SacI and then linked to each other to prepare a pUC-uraHA-ldh vector. A cassette for deleting pdc1 was amplified from the vector by performing a PCR using sequences of SEQ ID NOS: 41 and 42 having a homologous sequence with the pdc1 gene as primers. The SEQ ID NO: 41-1 to 41-41 and the SEQ ID NO: 42-1 to 42-44 represent the parts which were substituted with a pdc1 gene by a homologous recombination with a homologous sequence of *S. cerevisiae* chromosome.

(1.2) Preparation of *S. cerevisiae* CEN.PK2-1D (Δ pdc1::ldh)

The cassette for pdc1 deletion prepared in (1.1) was introduced to *S. cerevisiae* (CEN.PK2-1D, EUROSCARF accession number: 30000B). The cassette for pdc1 deletion was introduced by performing a general heat shock transformation. After the transformation, the cell was cultured in a uracil drop-out medium to substitute a pdc1 open reading frame (ORF) on the chromosome with the cassette.

To verify deletion of pdc1 in the cell obtained as a result, a PCR was performed by using the genome of the cell as a template and a primer set of SEQ ID NOS: 43 and 44 as primers to verify the deletion of pdc1 gene and introduction of an ldh gene. As a result, *S. cerevisiae* CEN.PK2-1 D (Δ pdc1::ldh) was prepared.

(2) Preparation of *S. cerevisiae* CEN.PK2-1D (Δ pdc1::ldh, Δ cyb2::ldh)

(2.1) Preparation of Vector for Deleting cyb2

To block a pathway from lactate to pyruvate in *S. cerevisiae* CEN.PK2-1 D (Δ pdc1::ldh) obtained in (1), cyb2 gene was removed.

Specifically, a cassette for cyb2 deletion was obtained by performing a PCR by using pUC-uraHA-ldh obtained in (1.1) as a template and cyb2 homologous sequences of SEQ ID NOS: 45 and 46 as primers. The SEQ ID NO: 45-1 to 45-45 and the SEQ ID NO: 46-1 to 46-45 represent the parts which were substituted with a cyb2 gene by a homologous recombination with *S. cerevisiae* chromosome.

(2.2) Preparation of *S. cerevisiae* CEN.PK2-1D (Δ pdc1::ldh, Δ cyb2::ldh)

The cassette for cyb2 deletion prepared in (2.1) was introduced to *S. cerevisiae* CEN.PK2-1D (Δ pdc1::ldh). The cassette for cyb2 deletion was introduced by performing a general heat shock transformation. After the transformation, the cell was cultured in a uracil drop-out medium to substitute a cyb2 ORF on the chromosome with the cassette.

To verify deletion of cyb2 in the cell obtained as a result, a PCR was performed by using the genome of the cell as a template and a primer set of SEQ ID NOS: 47 and 48 as primers to verify the deletion of the cyb2 gene. As a result, *S. cerevisiae CEN.PK*2-1D (Δ pdc1::ldh, Δ cyb2::ldh) was prepared.

(3) Preparation of *S. cerevisiae* CEN.PK2-1D (Δ pdc1::ldh, Δ cyb2, Δ gpd1::ldh)

(3.1) Preparation of Vector for gpd1 Deletion

To block a pathway from DHAP to G3P in *S. cerevisiae* CEN.PK2-1 D (Δ pdc1::ldh, Δ cyb2) prepared in (2), a gene encoding glycerol-3-phosphate dehydrogenase 1 (gpd1) was removed.

Specifically, a cassette for gpd1 deletion was obtained by performing a PCR by using pUC-uraHA-ldh obtained in (1.1) as a template and gpd1 homologous sequences of SEQ ID NOS: 49 and 50 as primers. The SEQ ID NO: 49-1 to 49-50 and the SEQ ID NO: 50-1 to 50-50 represent the parts which were substituted with a gpd1 gene by a homologous recombination with *S. cerevisiae* chromosome.

(3.2) Preparation of *S. cerevisiae* CEN.PK2-1D (Δ pdc1::ldh, Δ cyb2::ldh, Δ gpd1::ldh)

The cassette for gpd1 deletion prepared in (3.1) was introduced to *S. cerevisiae* CEN.PK2-1D (Δ pdc1::ldh, Δ cyb2::ldh) prepared in (2). The cassette for gpd1 deletion was introduced by performing a general heat shock transformation. After the transformation, the cell was cultured in a uracil drop-out medium to substitute a gpd1 ORF on the chromosome with the cassette.

To verify deletion of gpd1 in the cell obtained as a result, a PCR was performed by using the genome of the cell as a template and a primer set of SEQ ID NOS: 51 and 52 as primers to verify the deletion of gpd1 gene. As a result, *S. cerevisiae* CEN.PK2-1D (Δ pdc1::ldh, Δ cyb2::ldh, Δ gpd1::ldh) was prepared.

*S. cerevisiae* CEN.PK2-1D (Δ pdc1::ldh, Δ cyb2::ldh, Δ gpd1::ldh) was internationally deposited on May 30, 2013 with Accession Number KCTC12415BP to Korean Collection for Type Cultures (KCTC) which is an International Depositary Authority according to the Budapest Treaty.

(4) Preparation of *S. cerevisiae* CEN.PK2-1D (Δ pdc1::ldh, Δ cyb2::ldh, Δ gpd1::ldh, Δ adh1::ldh)

(4.1) Preparation of Vector for adh1 Deletion

To block a pathway from acetaldehyde to ethanol in *S. cerevisiae* CEN.PK2-1D (Δ pdc1::ldh, Δ cyb2::ldh, Δ gpd1::ldh) prepared in (3), a gene encoding alcohol dehydrogenase (adh1) was removed. To express Ldh at the same time as when the adh1 gene was removed, the adh1 gene was deleted by substituting the adh1 gene with an ldh-HPH cassette.

Specifically, a cassette for adh1 deletion was obtained by performing a PCR by using p416-ldh-HPH obtained in (1.1) as a template and adh1 homologous sequences of SEQ ID NOS: 53 and 54 as primers. The SEQ ID NOS: 53-1 to 53-51 and the SEQ ID NOS: 54-1 to 54-51 represent the parts which were substituted with a adh1 gene by a homologous recombination with a *S. cerevisiae* chromosome.

(4.2) Preparation of *S. cerevisiae* CEN.PK2-1D (Δ pdc1::ldh, Δ cyb2::ldh, Δ gpd1::ldh, Δ adh1::ldh)

The cassette for adh1 deletion prepared in (4.1) was introduced to *S. cerevisiae* CEN.PK2-1D (Δ pdc1::ldh, Δ cyb2::ldh, Δ gpd1::ldh) prepared in (3). The cassette for adh1 deletion was introduced by performing a general heat shock transformation. After the transformation, the cell was cultured in the presence of hygromycin B, which was a selection marker, to substitute an adh1 ORF on a chromosome with the cassette.

To verify deletion of adh1 in the cell obtained as a result, a PCR was performed by using the genome of the cell as a template and a primer set of SEQ ID NOS: 55 and 56 as primers to verify the deletion of an adh1 gene and the introduction of an ldh gene. As a result, *S. cerevisiae* CEN.PK2-1 D (Δ pdc1::ldh, Δ cyb2::ldh, Δ gpd1::ldh, Δ adh1::ldh) was prepared.

(5) Preparation of *S. cerevisiae* CEN.PK2-1D (Δ pdc1::ldh, Δ cyb2::ldh, Δ gpd1::ldh, Δ adh1::ldh, Δ ald6::mhpF)

(5.1) Preparation of Vector for mhpF Introduction and Introduction of Vector

To strengthen a pathway converting acetaldehyde to acetyl-CoA in *S. cerevisiae CEN.PK*2-1D (Δ pdc1::ldh, Δ cyb2::ldh, Δ gpd1::ldh, Δ adh1::ldh) prepared in (4), a MhpF gene was introduced to an ald6 gene site.

Specifically, to obtain the MhpF gene, a *S. cerevisiae* codon-optimized nucleotide sequence was obtained on the basis of an *E. coli*-derived MhpF gene, and the obtained sequence was synthesized (DNA2.0 Inc; SEQ ID NO: 22). The obtained MhpF gene and a 'HIS3 cassette' were respectively linked with a 'pUC19 vector' (NEB, N3041) by using a SalI restriction enzyme to prepare pUC19-His-MhpF vector (SEQ ID NO: 57). The HIS3 cassette was an amplification product obtained by performing a PCR by using pRS413 (ATCC8758) as a template and primers of SEQ ID NOS: 60 and 61 as primers. In the pUC19-His-MhpF vector, mhpF is expressed in the presence of a GPD promoter (SEQ ID NO: 29).

A PCR was performed by using the prepared pUC19-His-MhpF vector as a template and sequences formed by combining ald6 homologous sequences of SEQ ID NOS: 58 and 59 with promoters as primers. The SEQ ID NOS: 58-1 to 58-44 and the SEQ ID NOS: 59-1 to 59-45 represent the parts which were substituted with an ald6 gene by a homologous recombination with a *S. cerevisiae* chromosome.

(5.2) Preparation of *S. cerevisiae* CEN.PK2-1D (Δ pdc1::ldh, Δ cyb2::ldh, Δ gpd1::ldh, Δ adh1::ldh, Δ ald6::mhpF)

The cassette for mhpF insertion prepared in (5.1) was introduced to *S. cerevisiae* CEN.PK2-1D (Δ pdc1::ldh, Δ cyb2::ldh, Δ gpd1::ldh, Δ adh1::ldh) prepared in (4).

The cassette for adh1 deletion was introduced by performing a general heat shock transformation. After the transformation, the cell was cultured in a histidine drop-out medium (yeast nitrogen base without amino acids (Sigma-Aldrich: cat. no. Y0626) 6.7 g/L, yeast synthetic drop-out without histidine (Sigma-Aldrich: cat. no. Y1751) 1.9 g/L, and glucose 2 (w/v) %) to substitute an ald6 ORF on the chromosome with the cassette.

To verify deletion of an ald6 gene and introduction of a mhpF gene in the cell obtained as a result, a PCR was performed by using the genome of the cell as a template and a primer set of SEQ ID NOS: 62 and 63 as primers to verify the gene deletion and introduction. As a result, *S. cerevisiae* CEN.PK2-1D (Δ pdc1::ldh, Δ cyb2::ldh, Δ gpd1::ldh, Δ adh1::ldh, Δ ald6::mhpF) was prepared.

(6) Preparation of *S. cerevisiae* CEN.PK2-1D (Δ pdc1::ldh, Δ cyb2::ldh, Δ gpd1::ldh, Δ adh1::ldh, Δ ald6::mhpF, eutE+)

(6.1) Preparation of Vector for EutE Introduction and Introduction of Vector (6.1.1) Preparation of Dual Function Over-Expression Vector pCS-Ex1

A PCR was performed by using a primer combination of SEQ ID NOS: 89 and 90 from a pRS426GPD vector that is widely used as a yeast over-expression vector to obtain 689 bp of DNA fragment (GPD promoter). The DNA fragment was mixed with a pCtB1 vector (Genbank Accession Number KJ922019) treated with KpnI to perform cloning by using an In-fusion kit (Clonetech, cat. 639650). Then, the cloned DNA fragment was introduced by using a general method to a TOP10 strain (Invitrogen, cat. C4040-06) that is an *E. coli* strain for cloning. After the introduction, the strain was smeared on an LB agar medium (Bacto Tryptone 10 g/L, Yeast Extract 5 g/L, NaCl 10 g/L, and Bacto Agar 15 g/L) including 50 ug/ml of kanamycin and cultured. Plasmid DNAs were separated from colonies formed by culturing, and a plasmid having a plasmid sequence identical to SEQ ID NO: 91 was verified. As a result, a pCS-Ex1 vector that is a yeast dual function over-expression vector was obtained. The dual function refers to a function of expressing the gene after inserting the gene into a genome and another function of expressing the gene on a vector.

(6.1.2) Preparation of Yeast Dual Function *E. coli* eutE Gene Over-Expression Vector A PCR was performed by using a primer combination of SEQ ID NOS: 92 and 93 from genome DNA of *E. coli* MG1655 to obtain 1447 bp of a DNA fragment that was an EutE gene. The DNA fragment was mixed with a pCS-Ex1 vector treated with KpnI and SacI to perform cloning by using an In-fusion kit (Clonetech, cat. 639650). Then, the cloned DNA fragment was introduced by using a general method to a TOP10 strain (Invitrogen, cat. C4040-06) that is an *E. coli* strain for cloning. After the introduction, the strain was smeared on an LB agar medium including 50 ug/ml of kanamycin and cultured. Plasmid DNAs were separated from colonies formed by culturing, and a plasmid having a plasmid sequence identical to SEQ ID NO: 94 was verified. As a result, an MD1040 vector that is a yeast dual function *E. coli* eutE Gene over-expression vector was obtained.

(6.2) Preparation of Yeast Having Over-Expressed *E. coli* eutE Gene

A PCR was performed by using a primer combination of SEQ ID NOS: 95 and 96 from the prepared MD1040 vector to obtain 3985 bp of DNA fragment that was EutE gene. The DNA fragment was introduced by using a general method to *S. cerevisiae* CEN.PK2-1 D (Δ pdc1::ldh, Δ cyb2::ldh, Δ gpd1::ldh, Δ adh1::ldh, Δ ald6::mhpF). Then, the resulting strain was smeared on an SD-URA agar medium (Yeast nitrogen base without amino acids (Sigma-Aldrich: Cat. no. Y0626) 6.7 g/L, Yeast synthetic drop-out without uracil (Sigma-Aldrich: Cat. no. Y1501) 1.9 g/L, D-glucose 20 g/L, and Bacto Agar 20 g/L) that was a minimal medium without uracil. Among the colonies formed by three days of culturing, a colony that allowed for verifying 4357 bp of a DNA fragment by a PCR performed by using a primer combination of SEQ ID NOS: 97 and 98 was selected. In genome DNA of a wild-type strain, 2300 bp of a DNA fragment may be obtained by a PCR performed by using a primer combination of SEQ ID NOS: 97 and 98. The obtained clone was inoculated to a YPD medium (Bacto Peptone 20 g/L, Yeast Extract 10 g/L, and D-glucose 20 g/L), and the resulting culture medium was stirred at 30° C. at 230 rpm for culturing. Then, the resulting culture medium was smeared on a counter-selective medium including 5-FOA (Yeast nitrogen base without amino acids (Sigma-Aldrich: Cat. no. Y0626) 6.7 g/L, Yeast synthetic drop-out without uracil (Sigma-Aldrich: Cat. no. Y1501) 1.9 g/L, Uracil 0.1 g/L, D-glucose 20 g/L, 5-fluoroorotic acid (5-FOA) 1 g/L, and Bacto Agar 20 g/L). Among the colonies formed by three days of culturing, a colony that allowed for verifying 2963 bp of a DNA fragment by a PCR performed by using a primer combination of SEQ ID NOS: 97 and 98 was selected. As a result, *S. cerevisiae* CEN.PK2-1D (Δ pdc1::ldh, Δ cyb2::ldh, Δ gpd1::ldh, Δ adh1::ldh, Δ ald6::mhpF, eutE+) was prepared.

(7) Preparation of *S. cerevisiae* CEN.PK2-1D (Δ pdc1::ldh, Δ cyb2::ldh, Δ gpd1::ldh, Δ adh1::ldh, Δ ald6::mhpF, eutE+, A $P_{RCK1}$::$P_{TPI1}$)

(7.1) Preparation of Vector for RCK1 Gene Over-Expression and Introduction of Vector For over-expression of an RCK1 gene, an RCK 1 gene promoter ($P_{RCK11}$) of *S. cerevisiae* CEN.PK2-1 D was substituted with a TPI1 gene promoter ($P_{TPI1}$) having a higher expression level as follows. FIG. 1 shows a procedure of preparing a *S. cerevisiae* CEN.PK2-1D strain into which a vector was inserted, wherein an RCK 1 gene promoter was substituted in the vector.

To obtain a DNA fragment including a TPI1 gene promoter ($P_{TPI1}$) (SEQ ID NO: 64), Genomic-tip system (Qiagen) was used to extract chromosomal DNA (gDNA) of a *S. cerevisiae* wild-type strain CEN.PK2-1D, and a PCR was performed with the gDNA by using a PCR HL premix kit (BIONEER, the same hereinafter)

Figure 2:
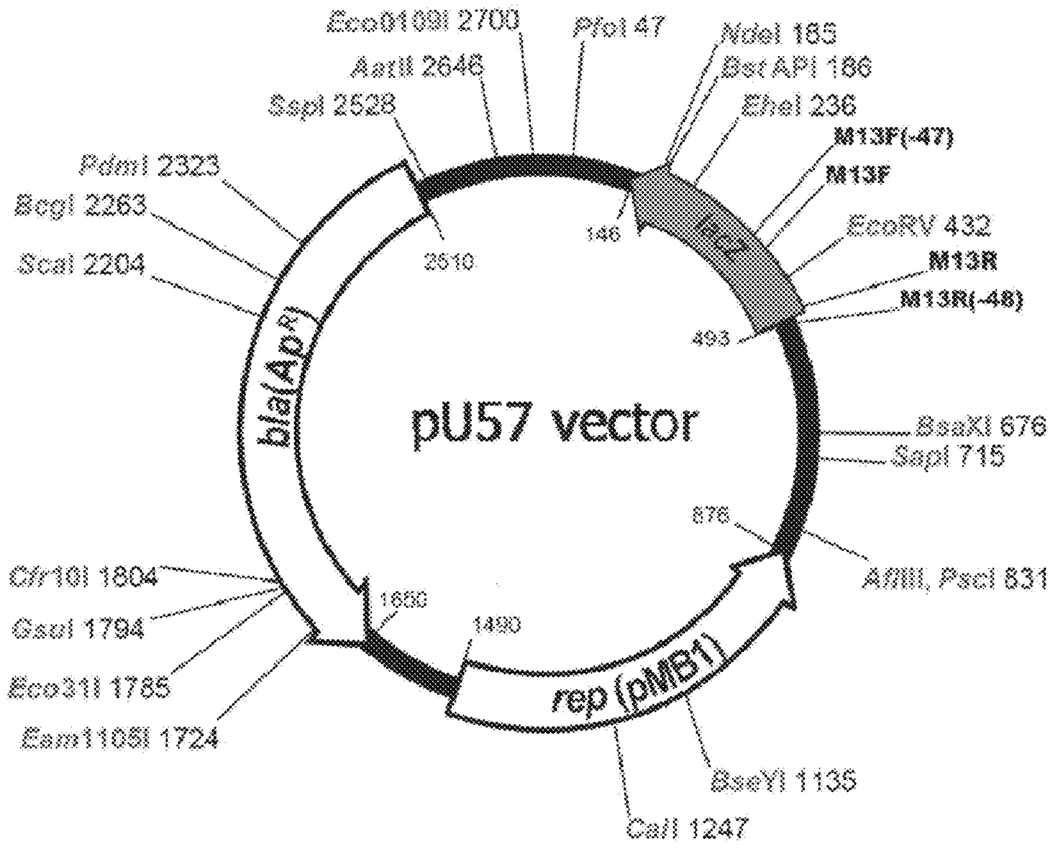
FIG. 2 is a diagram showing a PU57 vector.
Figure 3:
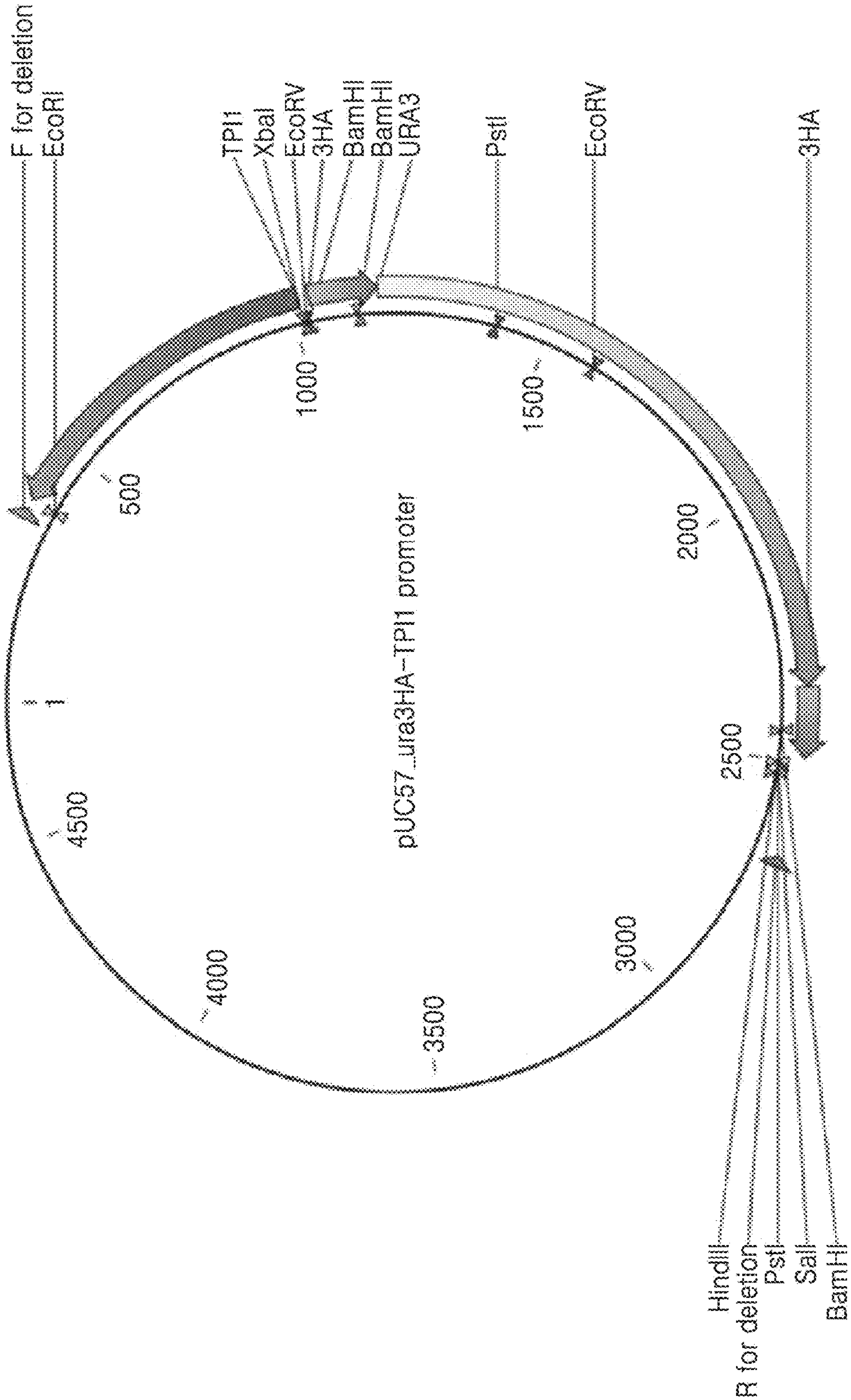
FIG. 3 a diagram showing a pUC57-ura3HA-$P_{TPI1}$ vector.

A PCR to amplify $P_{TPI1}$ was performed by using primers of SEQ ID NOS: 65 and 66, and repeating, 30 times, a cycle including denaturation at 94° C. for 30 seconds, annealing at 52° C. for 30 seconds, and elongation at 72° C. for 30 seconds. The PCR products were cleaved by using EcoRI to obtain DNA fragments (hereinafter referred to as "$P_{TPI1}$ cassette") by performing electrophoresis in a 0.8% agarose gel and elution. A P57 vector (GenScript) (SEQ ID NO: 67) and the obtained $P_{TPI1}$ cassette were treated with a restriction enzyme EcoR and ligated to prepare a p57-$P_{TPI1}$ (SEQ ID NO: 68). FIG. 2 is a diagram showing a P57 vector. FIG. 3 a diagram showing a p57-$P_{TPI1}$ vector.

(7.2) Preparation of *S. cerevisiae* CEN.PK2-1D (Δ pdc1::ldh, Δ cyb2::ldh, Δ gpd1::ldh, Δ adh1::ldh, Δ ald6::mhpF, eutE+, Δ $P_{RCK1}$::$P_{TPI1}$)

To substitute an RCK1 promoter ($P_{RCK11}$) with a PTPI1 promoter ($P_{TPI1}$) by homologous recombination, the p57-$P_{TPI1}$ vector was used. A PCR was performed by using the p57-$P_{TPI1}$ vector as a template and using primers of SEQ ID NOS: 69 and 70 to prepare a cassette for substituting $P_{RCK1}$ with $P_{TPI1}$.

The prepared substitution cassette was introduced to *S. cerevisiae CEN.PK*2-1D (Δ pdc1::ldh, Δ cyb2::ldh, Δ gpd1::ldh, Δ adh1::ldh, Δ ald6::mhpF, eutE+) prepared in (6) of Example 1. Specifically, the substitution cassette was mixed with 50% polyethylene glycol and single stranded carrier DNA, and the resulting culture solution was kept in a water tank at 42° C. for about one hour. Then, the *S. cerevisiae* CEN.PK2-1D (Δ pdc1::ldh, Δ cyb2::ldh, Δ gpd1::ldh, Δ adh1::ldh, Δ ald6::mhpF) culture solution was smeared on a uracil drop-out minimal solid medium (YSD 6.7 g/L yeast nitrogen base without amino acids, 1.4 g/L amino acid dropout mix (-ura)) and cultured at 30° C. for more than 24 hours.

Ten colonies (mutated strain) formed on the plate were selected and moved on the uracil drop-out medium again. At the same time, the colonies were cultured in a liquid medium containing the same substances to separate genome DNA from the strain by using a commercial kit (Gentra Puregene Cell kit, Qiagen, USA). To verify substitution of $P_{RCK1}$ with $P_{TPI1}$, a PCR was performed by using genome DNA of the separated mutated strain and primers of SEQ ID NOS: 71 and 72. Then, electrophoresis was performed on the obtained PCR products to verify the substitution of $P_{RCK1}$ with $P_{TPI1}$. As a result, *S. cerevisiae* CEN.PK2-1 D (Δ pdc1::ldh, Δ cyb2::ldh, Δ gpd1::ldh, Δ adh1::ldh, Δ ald6::mhpF, eutE+, A $P_{RCK1}$:$P_{TPI1}$) was obtained.

Example 2

Effect of MSN2 Gene Over-Expression in Yeast Cell (2.1) Preparation of Vector for MSN2 Over-Expression For MSN2 gene over-expression, a sequence including a MSN2 coding region (SEQ ID NO: 2) from genome DNA of *S. cerevisiae* CEN.PK2-1 D (MATα ura3-52; trp1-289; leu2-3,112; his3Δ 1; MAL2-8C; SUC2) EUROSCARF accession number: 30000B: also referred to as "CEN.PK2-1D strain") was amplified by performing a PCR using a primer set of SEQ ID NOS: 73 and 74 as primers. The amplification product was digested by using HindIII, and the digested product was linked to a pRS416 vector (ATCC87521) digested by using HindIII to prepare a pRS416-MSN2 vector. In the vector, the MSN2 gene is transcribed under a GPD promoter.

(2.2) Preparation of MSN2 Over-Expression Strain (2.2.1) Preparation of MSN2 Gene Over-Expression Genome Insertion Cassette A MSN2 genome insertion cassette for constitutive expression of the MSN2 gene in *S. cerevisiae* was prepared as follows.

Figure 4:
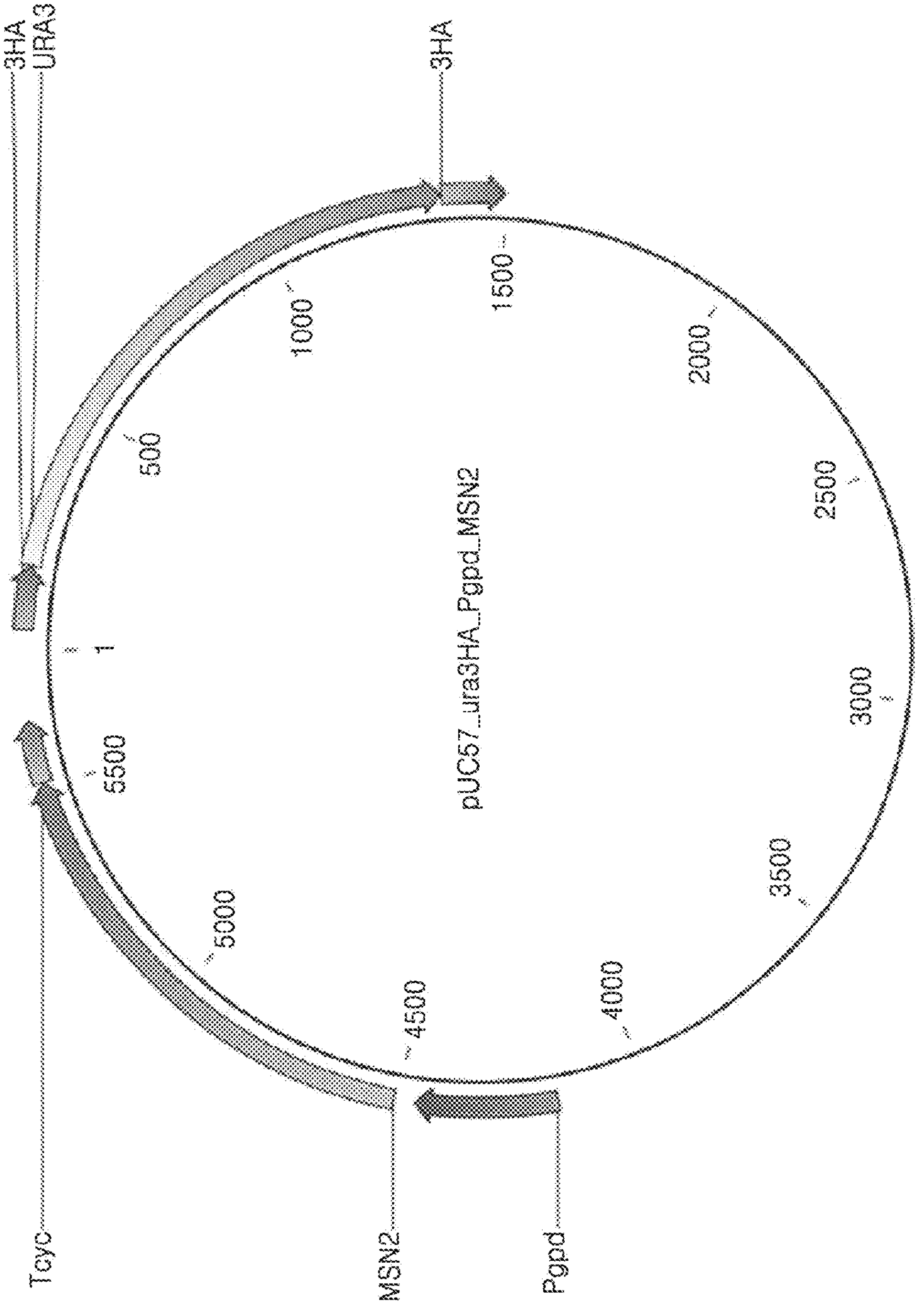
FIG. 4 is a schematic diagram showing a pUC57-ura3HA-Pgpd-MSN2 vector, wherein a uracil 3 gene that is an auxotrophic marker is inserted into the vector and the vector is a parent vector to prepare a cassette for inserting MSN2 into a genome.

The over-expression vector prepared in Example 2.1 was PCR amplified by using a primer set of SEQ ID NOS: 75 and 76. Then, the PCR fragment and the pUC57-URA3 vector prepared in (1.1) of Example 1 were cleaved by using SalI and ligated with the PCR fragment to prepare a pUC57-URA3-GPDp-MSN2 vector. FIG. 4 is a schematic diagram showing a pUC57-URA3-GPDp-MSN2 vector, wherein a uracil 3 gene that is an auxotrophic marker is inserted into the vector and the vector is a parent vector to prepare a cassette for inserting MSN2 to a genome as described later.

Then, a PCR was performed by using the prepared pUC57-URA3-GPDp-MSN2 vector as a template and primers of SEQ ID NOS: 77 and 78 to prepare a cassette into which MSN2 is inserted. The PCR was performed by keeping the PCR reactants at 95° C. for 4 minutes, and then repeating, 30 times, a cycle including denaturation at 94° C. for 30 seconds, annealing at 52° C. for 30 seconds, and elongation at 72° C. for 30 seconds. Then, the products were kept at 72° C. for 10 minutes.

(2.2.2) Preparation of *S. cerevisiae* CEN.PK2-1D (Δ pdc1::ldh, Δ cyb2::ldh, Δ gpd1::ldh, Δ adh1::ldh, Δ ald6::mhpF, eutE+, MSN2+)

For constitutive expression of MSN2 in *S. cerevisiae*, MSN2 genome was inserted as follows. CEN.PK2-1D (Δ pdc1::ldh, Δ cyb2::ldh, Δ gpd1::ldh, Δ adh1::ldh, Δ ald6::mhpF, eutE+) was smeared on a YPD solid medium (10 g yeast extract, 20 g peptone, 20 g glucose) and cultured for 24 hours at 30° C. A colony was inoculated to 10 ml of YPD liquid medium and cultured for 18 hours at 30° C. The culture solution including sufficiently cultured cells was 1% (v/v) inoculated to 50 ml of YPD liquid medium contained in a 250 ml flask to culture in an incubator at 230 rpm and at 30° C.

After 4 to 5 hours, when an optical density at 600 nanometers ($OD_{600}$) value became about 0.5, the culture solution was centrifugated at 4,500 rpm for 10 minutes to obtain the cells. Then, the cells were re-suspended in a 100 mM lithium acetate solution. Then, the resulting solution was again centrifugated at 4,500 rpm for 10 minutes to obtain the cells. Subsequently, the cells were again re-suspended in 1 M lithium acetate solution including 15% glycerol, and the resulting solution was divided in a volume of 100 ul.

For constitutive expression of MSN2, the cassette having an inserted MSN2 and prepared in Example 2.2.1 was mixed with 50% polyethylene glycol and single stranded carrier DNA, and the resulting culture solution was kept in a water tank at 42° C. for about one hour. Then, the culture solution was smeared on a uracil drop-out minimal solid medium (YSD 6.7 g/L yeast nitrogen base without amino acids, 1.4 g/L Amino acid dropout mix (-ura)) and cultured at 30° C. for more than 24 hours.

Eight colonies (mutated strain) formed on the plate were selected and moved on the YSD (-URA) solid medium again. At the same time, the colonies were cultured in a YSD (-URA) liquid medium to separate genome DNA from the strain by using a commercial kit (Gentra Puregene Cell kit, Qiagen, USA). To verify insertion of MSN2, a PCR was performed by using genome DNA of the separated mutated strain and primers of SEQ ID NOS: 79 and 80. Then, electrophoresis was performed on the obtained PCR products to verify the insertion of the MSN2 expression cassette. As a result, *S. cerevisiae* CEN.PK2-1D (Δ pdc1::ldh, Δ cyb2::ldh, Δ gpd1::ldh, Δ adh1::ldh, Δ ald6::mhpF, eutE+, MSN2+) was obtained.

(2.2.3) Preparation of *S. cerevisiae* CEN.PK2-1D (Δ pdc1::ldh, Δ cyb2::ldh, Δ gpd1::ldh, Δ adh1::ldh, Δ ald6::mhpF, eutE+, A $P_{RCK1}$::$P_{TPI1}$, MSN2+)

For constitutive expression of MSN2 in *S. cerevisiae*, a MSN2 genome insertion was performed as follows. CEN.PK2-1D (Δ pdc1::ldh, Δ cyb2::ldh, Δ gpd1::ldh, Δ adh1::ldh, Δ ald6::mhpF, eutE+, Δ $P_{RCK1}$:$P_{TPI1}$) was smeared on a YPD solid medium (10 g yeast extract, 20 g peptone, 20 g glucose) and cultured for 24 hours at 30° C.

A colony was inoculated to 10 ml of a YPD liquid medium and cultured for 18 hours at 30° C. The culture solution including sufficiently cultured cells was 1% (v/v) inoculated to 50 ml of YPD liquid medium contained in a 250 ml flask to culture in an incubator at 230 rpm and at 30° C.

After 4 to 5 hours, when an $OD_{600}$ value became about 0.5, the culture solution was centrifugated at 4,500 rpm for 10 minutes to obtain the cells. Then, the cells were re-suspended in a 100 mM lithium acetate solution. Then, the resulting solution was again centrifugated at 4,500 rpm for 10 minutes to obtain the cells. Subsequently, the cells were again re-suspended in 1 M lithium acetate solution including 15% glycerol, and the resulting solution was divided in a volume of 100 ul.

For constitutive expression of MSN2, the cassette having an inserted MSN2 and prepared in Example 2.2.1 was mixed with 50% polyethylene glycol and single stranded carrier DNA, and the resulting culture solution was kept in a water tank at 42° C. for about one hour. Then, the culture solution was smeared on a uracil drop-out minimal solid medium (YSD 6.7 g/L yeast nitrogen base without amino acids, 1.4 g/L Amino acid dropout mix (-his)) and cultured at 30° C. for more than 24 hours. Eight colonies (mutated strain) formed on the plate were selected and moved on the YSD (-URA) solid medium again. At the same time, the colonies were cultured in a YSD (-URA) liquid medium to separate genome DNA from the strain by using a commercial kit (Gentra Puregene Cell kit, Qiagen, USA). To verify insertion of MSN2, a PCR was performed by using genome DNA of the separated mutated strain and primers of SEQ ID NOS: 79 and 80. Then, electrophoresis was performed on the obtained PCR products to verify the insertion of the MSN2 expression cassette. As a result, *S. cerevisiae* CEN.PK2-1 D (Δ pdc1::ldh, Δ cyb2::ldh, Δ gpd1::ldh, Δ adh1::ldh, Δ ald6::mhpF, eutE+, A $P_{RCK1}$:$P_{TPI1}$, MSN2+) was obtained.

Example 3

Verification of Growth, Glucose Consumption, and Ethanol and Lactate Production of MSN2 Over-Expressed Yeast Cell The *S. cerevisiae* CEN.PK2-1D (Δ pdc1::ldh, Δ cyb2::ldh, Δ gpd1::ldh, Δ adh1::ldh, Δ ald6::mhpF, eutE+, MSN2+) yeast cell prepared above was inoculated to 50 ml of a minimal Ura drop-out medium including 4% glucose until an $OD_{600}$ became 1. Then, the resulting medium was stirred at 30° C. at 90 rpm to culture under microaerobic conditions for 48 hours. Cell growth during the culturing was measured by measuring an $OD_{600}$ value by using a spectrophotometer. The residual glucose and ethanol concentrations were analyzed by high performance liquid chromatography (HPLC).

The results of culturing performed for about 68 hours, including cell growth ($OD_{600}$ value), and residual glucose and lactate concentrations in the medium, are shown in Table 1.

TABLE 1

| Strain | Cell Growth ($OD_{600}$) | Glucose Consumption (g/L) | Lactate Production (g/L) | Yield (g/g %) |
|---|---|---|---|---|
| Control Group | 4.40 | 31.72 | 20.44 | 68.77 |
| MSN2 Strengthened Strain | 3.96 | 34.48 | 22.93 | 70.70 |

In Table 1, the control group represents *S. cerevisiae* CEN.PK2-1D (Δ pdc1::ldh, Δ cyb2::ldh, Δ gpd1::ldh, Δ adh1::ldh, Δ ald6::mhpF, eutE+), and the MSN2 strengthened strain represents *S. cerevisiae* CEN.PK2-1 D (Δ pdc1::ldh, Δ cyb2::ldh, Δ gpd1::ldh, Δ adh1::ldh, Δ ald6::mhpF, eutE+, MSN2+). As shown in Table 1, the experimental strain showed cell growth lower than that of the control group, but glucose consumption, lactate production, and yield of the experimental group strain were higher than those of the control group. Lactate production of the MSN2 strengthened strain was higher than that of the control group by 12.2%.

Example 4

Verification of MSN2 Gene Over-Expression and Trehalose Gene Over-Expression, and Lactate Resistance-Strengthening Effect of MSN2 Over-Expressed Cell (1) Verification and MSN2 Gene Expression Expression of a MSN2 gene of a MSN2 strengthened strain was verified by using qRT-PCT. The MSN2 strengthened strain represents *S. cerevisiae* CEN.PK2-1D (Δ pdc1::ldh, Δ cyb2::ldh, Δ gpd1::ldh, Δ adh1::ldh, Δ ald6::mhpF, eutE+, msn2+). With respect to an expression of an endogenous MSN2 gene of the MSN2 strengthened strain as 1, the expression of the MSN2 gene of the MSN2 strengthened strain was measured. Specifically, sampling was performed in a 125 ml flask at the time after culturing the MSN2 strengthened strain for 0 h, 19 h, 25 h, and 46 h. Then, an RNeasy mini kit (Qiagen co.) was used to extract the total RNA. The extracted RNA was used to synthesize a cDNA by using SuperScript® III First-Strand Synthesis System (Invitrogen) by using the extracted RNA. Then, primers of SEQ ID NOS: 81 and 82 specifically binding to the MSN2 gene were mixed with IQ SYBR Green Supermix (Bio-rad) according to a protocol provided by the manufacture to verify a relative amount of expression by using a qRT-PCR detection system (CFX96 realtime PCR detection system, Bio-rad).

Figure 5:
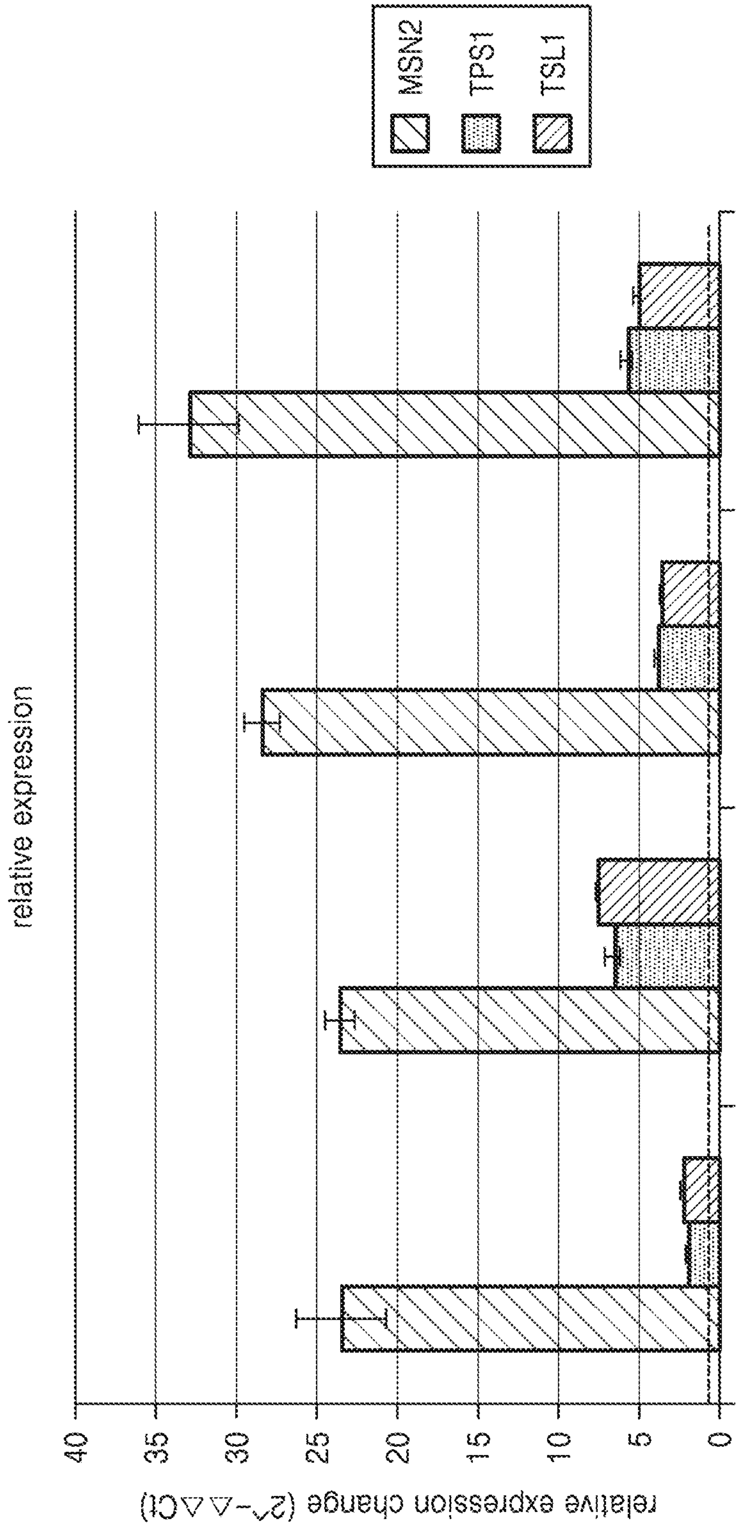
FIG. 5 is a graph showing MSN2, TPS1, and TSL1 gene expression of a MSN2 strengthened strain.

FIG. 5 is a graph showing MSN2 gene expression of a MSN2 strengthened strain. A relative amount of expression was compared by ΔΔ CT method by using TAF10 as a reference gene. The bars represent a standard error of expression amount values obtained by three times of repeated measurement. As shown in FIG. 5, it was verified that the MSN2 gene was actually over-expressed by about 20 to 30 times more in the MSN2 strengthened strain in comparison with the control group. The control group is *S. cerevisiae* CEN.PK2-1D (Δ pdc1::ldh, Δ cyb2::ldh, Δ gpd1::ldh, Δ adh1::ldh, Δ ald6::mhpF, eutE+).

(2) Verification of Trehalose Gene Expression

FIG. 5 is a graph showing expression of TPS1 and TSL1 genes of a MSN2 strengthened strain. The TPS1 and TSL1 genes are examples of an STRE gene. As shown in FIG. 5, in the MSN2 strengthened strain, expression of the TPS1 gene was verified by performing a PCR using primers of SEQ ID NOS: 83 and 84, and expression of the TSL1 gene was verified by performing a PCR using primers of SEQ ID NOS: 85 and 86. As a result, it was verified that the TPS1 and TSL1 genes are over-expressed by about five times more in the MSN2 strengthened strain in comparison with the control group. The control group is *S. cerevisiae* CEN.PK2-1D (Δ pdc1::ldh, Δ cyb2::ldh, Δ gpd1::ldh, Δ adh1::ldh, Δ ald6::mhpF, eutE+). Therefore, it was verified that the MSN2 strengthened strain expresses genes related to stress reactions.

Figure 6:
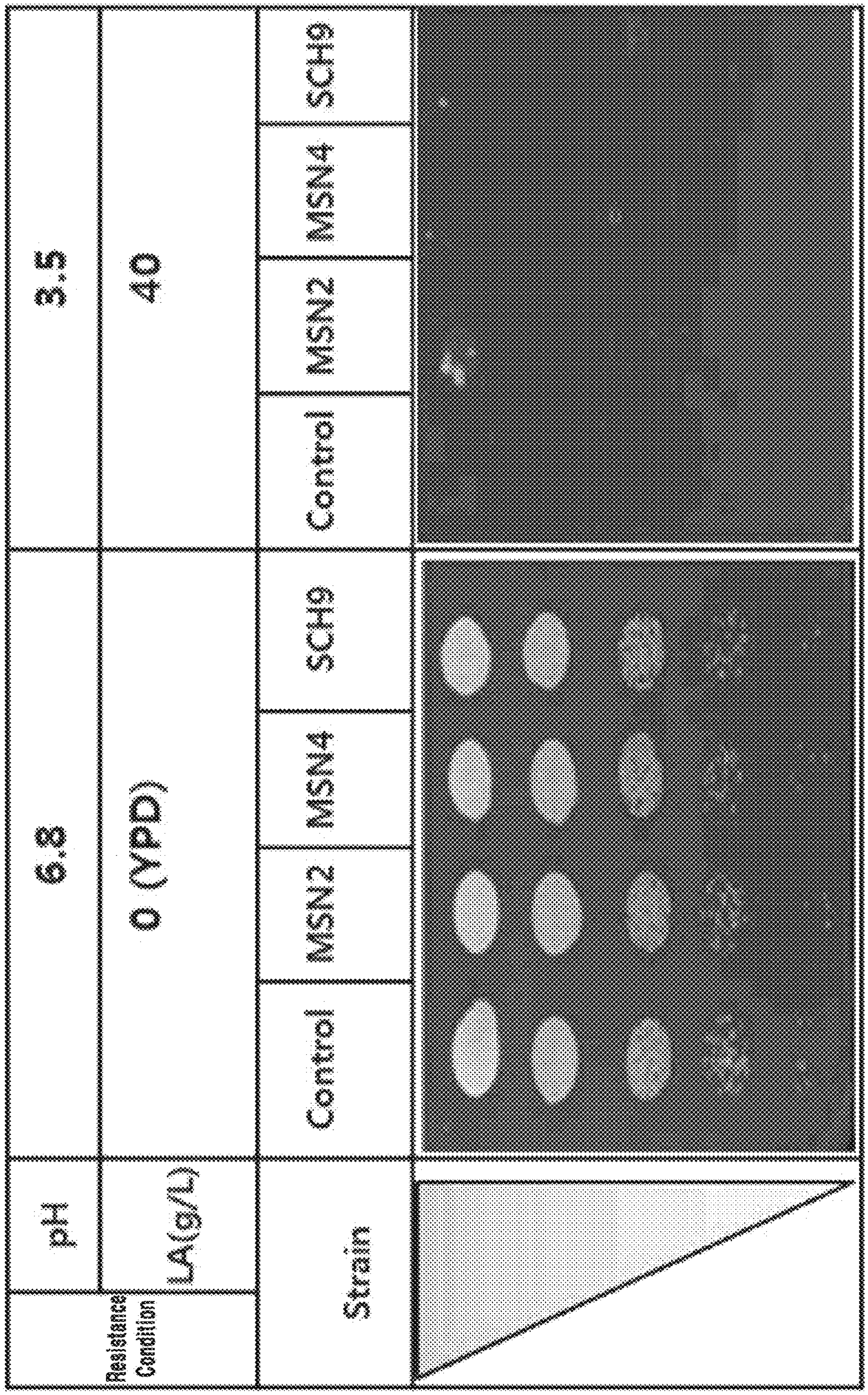
FIG. 6 is a set of photographs showing results of spotting of several strains, including a MSN2 strengthened strain.

(3) Verification of Lactate Resistance-Strengthening Effect (3.1) Evaluation of Acid Resistance of MSN2 Strengthened Strain At an OD value of about 1, about 4 μl of a MSN2 strengthened strain was spotted to a YPD solid medium including pH 3.5 and 40 g/L of lactate. FIG. 6 shows results of spotting of a MSN2 strengthened strain. In FIG. 6, the control group represents *S. cerevisiae* CEN.PK2-1D (Δ pdc1::ldh, Δ cyb2::ldh, Δ gpd1::ldh, Δ adh1::ldh, Δ ald6::mhpF, eutE+), and MSN2 represents a *S. cerevisiae CEN.PK*2-1D (Δ pdc1::ldh, Δ cyb2::ldh, Δ gpd1::ldh, Δ adh1::ldh, Δ ald6::mhpF, eutE+, MSN+) strain. As shown in FIG. 6, no colony of the control group was observed at pH 3.5, but colonies of the MSN2 strengthened strain were observed at pH 3.5. Therefore, it was verified that the MSN2 strengthened strain has resistance to acidic conditions. It was verified that the MSN2 strengthened strain has resistance to lactate and an acid of pH 3.5.

(3.2) Evaluation of Acid Resistance of MSN2 Strengthened Strain in Fermenter

*S. cerevisiae* CEN.PK2-1D (Δ pdc1::ldh, Δ cyb2::ldh, Δ gpd1::ldh, Δ adh1::ldh, Δ ald6::mhpF, A $P_{RCK1}$::$P_{TPI1}$, eutE+, MSN2+) that was the MSN2 strengthened strain prepared in (2.2) of Example 2 was inoculated to a YPD medium including 8% glucose, 1% yeast extract, and 2% Bacto-peptone. The resulting culture solution was cultured at 30° C. at about a 90 rpm stirring rate for a total of 46 hours. At the start of the culturing, the $OD_{600}$ value was 1. The culture solution was periodically sampled during the culturing from the culture flask to measure an OD value, and lactate, glucose, ethanol, and glycerol concentrations. To test acid resistant fermentation conditions, a final pH value, an OD value, glucose consumption, lactate production, and ethanol and glycerol concentrations were measured in the case where the amount of the used neutralizing agent $Ca(OH)_2$ was reduced by half.

Table 2 shows an OD value, glucose consumption, a final pH value, and lactate, ethanol, and glycerol concentrations, when the concentration of used 5N $Ca(OH)_2$ was adjusted after 46 hours of fermentation of a control group and a MSN2 strengthened strain. The control group represents *S. cerevisiae* CEN.PK2-1 D (Δ pdc1::ldh, Δ cyb2::ldh, Δ gpd1::ldh, Δ adh1::ldh, Δ ald6::mhpF, eutE+, Δ $P_{RCK1}$:$P_{TPI1}$), and the MSN2 strengthened strain represents *S. cerevisiae* CEN.PK2-1D (Δ pdc1::ldh, Δ cyb2::ldh, Δ gpd1::ldh, Δ adh1::ldh, Δ ald6::mhpF, eutE+, A $P_{RCK1}$:$P_{TPI1}$, MSN2+).

As shown in Table 2, when the amount of $Ca(OH)_2$ was reduced by half, the final pH value was reduced from about 3.3 to about 3.1. The OD value of the MSN2 strengthened strain was increased from 10.44 to 10.58, as the cell growth was increased. The OD value of the control group was decreased from 11.32 to 10.58, as the cell growth was decreased. With respect to lactate production at a lower pH, the lactate production by the MSN2 strengthened strain (105.95 g/L) was higher than that by the control group (99.99 g/L). These results showed that the MSN2 strengthened strain has resistance, for example, acid resistance, or resistance to a lower pH value.

TABLE 2

| Strain | Control Group | MSN2 Strengthened Strain | Control Group | MSN2 Strengthened Strain |
|---|---|---|---|---|
| 5N $Ca(OH)_2$ (g/L) | 235.00 | 235.00 | 117.00 | 117.00 |
| $OD_{600}$ | 11.32 | 10.44 | 10.58 | 10.58 |
| Glucose Consumption (g/L) | 165.00 | 165.45 | 131.78 | 142.22 |
| Final pH | 3.37 | 3.33 | 3.17 | 3.14 |
| Lactate Concentration (g/L) | 124.07 | 123.26 | 99.99 | 105.95 |
| Ethanol Concentration (g/L) | 6.89 | 7.94 | 7.10 | 8.74 |
| Glycerol Concentration (g/L) | 0.30 | 0.39 | 0.24 | 0.28 |

Example 5

Metabolite Analysis of MSN2 Strengthened Strain

Metabolites produced by the culturing of the MSN2 strengthened strain under the fermentation conditions described above were qualitatively/quantitatively analyzed. The instrument used for the analysis was a gas chromatography-mass spectrometry device (Agilent GC/MS 7890A/5975), and samples were separated by using a DB-5MS column. The samples underwent syliation performed by using an MSTFA [N-Methyl-N-(trimethylsilyl)trifluoroacetamide]derivatization reactant so that the samples could be analyzed by gas chromatography.

(5.1) Glycerol Concentration Analysis

Figure 7:
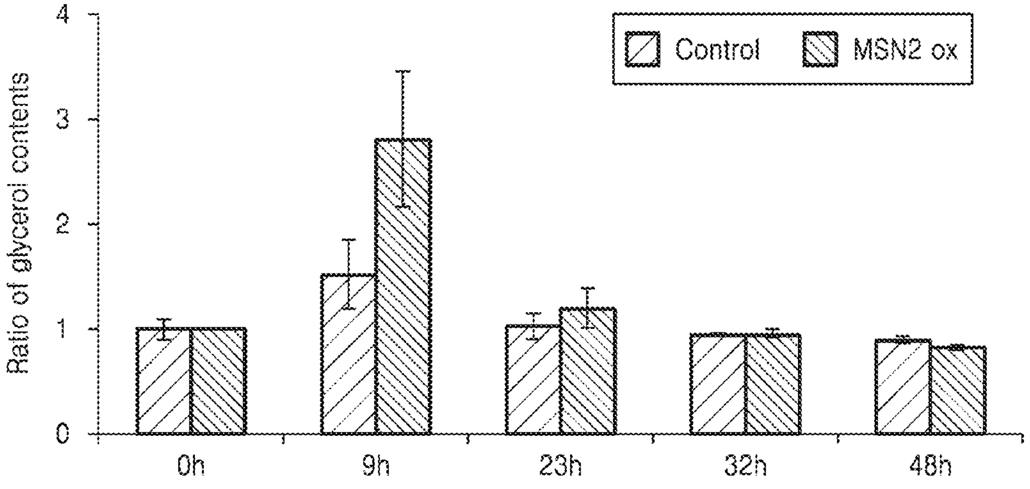
FIG. 7 is a graph showing glycerol concentration of a MSN2 strengthened strain during culturing.

Glycerol concentration inside a cell during the culturing was measured. FIG. 7 is a graph showing internal glycerol concentration of a MSN2 strengthened strain during culturing. As shown in FIG. 7, the glycerol concentration of the MSN2 strengthened strain was increased from 2.30 ng/$10^7$ cells to 4.74 ng/$10^7$ cells at the time about 9 hours after initiating the fermentation, which was about two times more than the glycerol concentration of the control group, and the glycerol concentration of the MSN2 strengthened strain was maintained at a high concentration after the increase.

As lactate is produced at an early part of fermentation, pH is reduced. When pH is maintained in a range from a neutral pH to about pH 4, lactate exists as an anion, wherein the anion form of lactate may cause osmotic pressure. In the case of the MSN2 strengthened strain, the glycerol concentration was increased for 9 hours after initiating the fermentation. This shows that the MSN2 strengthened strain resisted osmotic pressure caused by an anion form of lactate. Therefore, the result showed that the MSN2 strengthened strain having a high glycerol concentration has resistance to osmotic pressure.

(5.2) Trehalose Concentration Analysis

Figure 8:
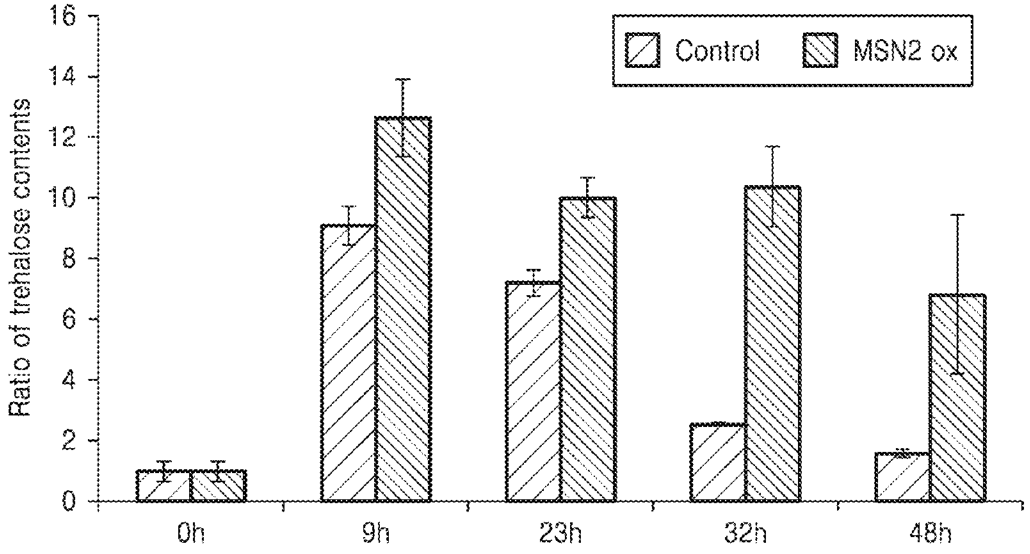
FIG. 8 is a graph showing trehalose concentration of a MSN2 strengthened strain during culturing.

Trehalose concentration inside a cell during the culturing was measured. FIG. 8 is a graph showing internal trehalose concentration of a MSN2 strengthened strain during culturing. As shown in FIG. 8, the trehalose concentration of the MSN2 strengthened strain was increased from 9.08 μg/$10^7$ cells to 12.62 μg/$10^7$ cells about 9 hours after initiating the fermentation, and the trehalose concentration of the MSN2 strengthened strain was maintained at a high concentration after the increase. A high trehalose concentration shows that the cells have resistance to osmotic pressure and/or acid.

(5.3) 9-Hexadecenoic Acid Concentration Analysis

Figure 9:
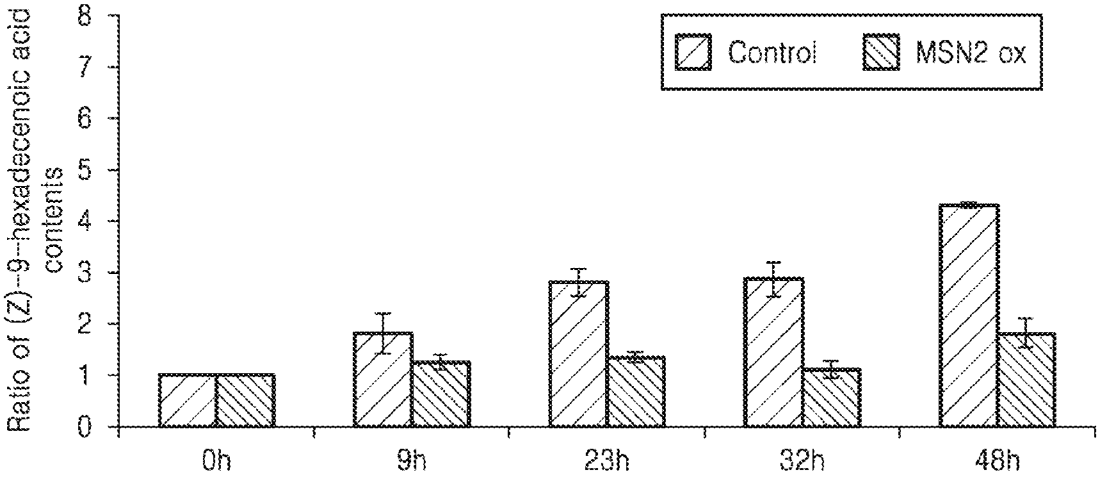
FIG. 9 is a graph showing 9-hexadecenoic acid concentration of a MSN2 strengthened strain during culturing. The ratio of (Z)-9-hexadecenoic acid content at each time (i.e., 0, 9, 23, 32, 48 hrs) is determined relative to (Z)-9-hexadecenoic acid content at 0 hrs.

Fatty acid concentration of a cell during the culturing was measured. FIG. 9 is a graph showing 9-hexadecenoic acid concentration of a MSN2 strengthened strain during culturing. The 9-hexadecenoic acid is referred to as a 16:1 fatty acid. As shown in FIG. 9, the 9-hexadecenoic acid concentration of the MSN2 strengthened strain was decreased by about 30% about 9 hours after initiating the fermentation in comparison with the control group, and the fatty acid was maintained at a low concentration. This result shows that the fatty acid is maintained at a low concentration in the MSN2 strengthened strain to inhibit cell membrane fluidity so that cell membrane rigidity may be consequently increased to have a stress tolerance such as acid resistance.

<Accession Number>

Research Center Name: Korea Research Institute of Bioscience and Biotechnology

Accession Number: KCTC 12415BP

Accession Date: May 30, 2013

As described above, a yeast cell having stress-resistance may be produced.

According to a method of producing a yeast cell having enhanced stress-resistance, a yeast cell having enhanced stress-resistance may be produced.

According to a method of producing lactate, lactate may be produced at a high concentration and a high yield.

It should be understood that the exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A yeast cell of genus *Saccharomyces* comprising inactivated endogenous pyruvate decarboxylase 1 (pdc1), cvtochrome-c oxidoreductase (cvb2), and alcohol dehydrogenase 1 (adh1) genes, an exogenous gene that expresses a MSN2 having 95% or more amino acid sequence identity with SEQ ID NO:1, an exogenous gene encoding *E. coil* MhpF, and an exogenous gene encoding a polypeptide that converts pyruvate to lactate and comprises an amino acid sequence having a 95% or more sequence identity with SEQ ID NO: 3, wherein the yeast cell produces lactate and is capable of growth at pH 3.0 to 3.8.

2. The yeast cell of claim 1, wherein the yeast cell has a decreased amount of hexadecenoic acid in comparison with the parent cell.

3. The yeast cell of claim 1, wherein the yeast cell has an increased amount of glycerol or trehalose in comparison with the parent cell.

4. The yeast cell of claim 3, wherein a gene encoding a polypeptide converting dihydroxy acetone phosphate (DHAP) to glycerol-3-phosphate is deleted or disrupted in the yeast cell.

5. The yeast cell of claim 1, wherein the yeast cell produces lactate.

6. The yeast cell of claim 1, wherein the yeast cell comprises a polynucleotide encoding a polypeptide that converts pyruvate to lactate.

7. The yeast cell of claim 5, wherein genes encoding a polypeptide that converts DHAP to glycerol-3-phosphate, and aldehyde dehydrogenase are deleted or disrupted in the yeast cell.

8. The yeast cell of claim 5, wherein the yeast cell further comprises an exogenous gene encoding a radiation sensitivity complementing kinase.

9. The yeast cell of claim 1, wherein the yeast cell is *Saccharomyces cerevisiae.*

10. A method of preparing lactate, the method comprising culturing the yeast cell of claim 5 in a culture medium, whereby the yeast cell produces lactate.

11. The method of claim 10, further comprising recovering the lactate from a culture solution.

12. The method of claim 10, wherein the culturing is performed at a pH of about 2 to about 6.5.

13. The yeast cell of claim 2, wherein the yeast cell has an increased amount of glycerol or trehalose in comparison with the parent cell.

* * * * *

SEQUENCE LISTING

```
<160> NUMBER OF SEQ ID NOS: 98

<210> SEQ ID NO 1
<211> LENGTH: 704
<212> TYPE: PRT
<213> ORGANISM: Saccharomyces cerevisiae

<400> SEQUENCE: 1

Met Thr Val Asp His Asp Phe Asn Ser Glu Asp Ile Leu Phe Pro Ile
  1               5                  10                  15

Glu Ser Met Ser Ser Ile Gln Tyr Val Glu Asn Asn Asn Pro Asn Asn
             20                  25                  30

Ile Asn Asn Asp Val Ile Pro Tyr Ser Leu Asp Ile Lys Asn Thr Val
         35                  40                  45

Leu Asp Ser Ala Asp Leu Asn Asp Ile Gln Asn Gln Glu Thr Ser Leu
     50                  55                  60

Asn Leu Gly Leu Pro Pro Leu Ser Phe Asp Ser Pro Leu Pro Val Thr
```

-continued

```
 65                  70                  75                  80

Glu Thr Ile Pro Ser Thr Thr Asp Asn Ser Leu His Leu Lys Ala Asp
                85                  90                  95

Ser Asn Lys Asn Arg Asp Ala Arg Thr Ile Glu Asn Asp Ser Glu Ile
            100                 105                 110

Lys Ser Thr Asn Asn Ala Asn Gly Ser Gly Ala Asn Gln Tyr Thr Thr
        115                 120                 125

Leu Thr Ser Pro Tyr Pro Met Asn Asp Ile Leu Tyr Asn Met Asn Asn
    130                 135                 140

Pro Leu Gln Ser Pro Ser Pro Ser Ser Val Pro Gln Asn Pro Thr Ile
145                 150                 155                 160

Asn Pro Pro Ile Asn Thr Ala Ser Asn Glu Thr Asn Leu Ser Pro Gln
                165                 170                 175

Thr Ser Asn Gly Asn Glu Thr Leu Ile Ser Pro Arg Ala Gln Gln His
            180                 185                 190

Thr Ser Ile Lys Asp Asn Arg Leu Ser Leu Pro Asn Gly Ala Asn Ser
        195                 200                 205

Asn Leu Phe Ile Asp Thr Asn Pro Asn Asn Leu Asn Glu Lys Leu Arg
    210                 215                 220

Asn Gln Leu Asn Ser Asp Thr Asn Ser Tyr Ser Asn Ser Ile Ser Asn
225                 230                 235                 240

Ser Asn Ser Asn Ser Thr Gly Asn Leu Asn Ser Ser Tyr Phe Asn Ser
                245                 250                 255

Leu Asn Ile Asp Ser Met Leu Asp Asp Tyr Val Ser Ser Asp Leu Leu
            260                 265                 270

Leu Asn Asp Asp Asp Asp Asp Thr Asn Leu Ser Arg Arg Arg Phe Ser
        275                 280                 285

Asp Val Ile Thr Asn Gln Phe Pro Ser Met Thr Asn Ser Arg Asn Ser
    290                 295                 300

Ile Ser His Ser Leu Asp Leu Trp Asn His Pro Lys Ile Asn Pro Ser
305                 310                 315                 320

Asn Arg Asn Thr Asn Leu Asn Ile Thr Thr Asn Ser Thr Ser Ser Ser
                325                 330                 335

Asn Ala Ser Pro Asn Thr Thr Thr Met Asn Ala Asn Ala Asp Ser Asn
            340                 345                 350

Ile Ala Gly Asn Pro Lys Asn Asn Asp Ala Thr Ile Asp Asn Glu Leu
        355                 360                 365

Thr Gln Ile Leu Asn Glu Tyr Asn Met Asn Phe Asn Asp Asn Leu Gly
    370                 375                 380

Thr Ser Thr Ser Gly Lys Asn Lys Ser Ala Cys Pro Ser Ser Phe Asp
385                 390                 395                 400

Ala Asn Ala Met Thr Lys Ile Asn Pro Ser Gln Gln Leu Gln Gln Gln
                405                 410                 415

Leu Asn Arg Val Gln His Lys Gln Leu Thr Ser Ser His Asn Asn Ser
            420                 425                 430

Ser Thr Asn Met Lys Ser Phe Asn Ser Asp Leu Tyr Ser Arg Arg Gln
        435                 440                 445

Arg Ala Ser Leu Pro Ile Ile Asp Asp Ser Leu Ser Tyr Asp Leu Val
    450                 455                 460

Asn Lys Gln Asp Glu Asp Pro Lys Asn Asp Met Leu Pro Asn Ser Asn
465                 470                 475                 480

Leu Ser Ser Ser Gln Gln Phe Ile Lys Pro Ser Met Ile Leu Ser Asp
                485                 490                 495
```

-continued

```
Asn Ala Ser Val Ile Ala Lys Val Ala Thr Thr Gly Leu Ser Asn Asp
            500                 505                 510

Met Pro Phe Leu Thr Glu Glu Gly Glu Gln Asn Ala Asn Ser Thr Pro
        515                 520                 525

Asn Phe Asp Leu Ser Ile Thr Gln Met Asn Met Ala Pro Leu Ser Pro
    530                 535                 540

Ala Ser Ser Ser Ser Thr Ser Leu Ala Thr Asn His Phe Tyr His His
545                 550                 555                 560

Phe Pro Gln Gln Gly His His Thr Met Asn Ser Lys Ile Gly Ser Ser
                565                 570                 575

Leu Arg Arg Arg Lys Ser Ala Val Pro Leu Met Gly Thr Val Pro Leu
            580                 585                 590

Thr Asn Gln Gln Asn Asn Ile Ser Ser Ser Ser Val Asn Ser Thr Gly
        595                 600                 605

Asn Gly Ala Gly Val Thr Lys Glu Arg Arg Pro Ser Tyr Arg Arg Lys
    610                 615                 620

Ser Met Thr Pro Ser Arg Arg Ser Ser Val Val Ile Glu Ser Thr Lys
625                 630                 635                 640

Glu Leu Glu Glu Lys Pro Phe His Cys His Ile Cys Pro Lys Ser Phe
                645                 650                 655

Lys Arg Ser Glu His Leu Lys Arg His Val Arg Ser Val His Ser Asn
            660                 665                 670

Glu Arg Pro Phe Ala Cys His Ile Cys Asp Lys Lys Phe Ser Arg Ser
        675                 680                 685

Asp Asn Leu Ser Gln His Ile Lys Thr His Lys Lys His Gly Asp Ile
    690                 695                 700


<210> SEQ ID NO 2
<211> LENGTH: 2115
<212> TYPE: DNA
<213> ORGANISM: Saccharomyces cerevisiae

<400> SEQUENCE: 2

atgacggtcg accatgattt caatagcgaa gatattttat tccccataga aagcatgagt      60

agtatacaat acgtggagaa taataaccca aataatatta acaacgatgt tatcccgtat     120

tctctagata tcaaaaacac tgtcttagat agtgcggatc tcaatgacat tcaaaatcaa     180

gaaacttcac tgaatttggg gcttcctcca ctatctttcg actctccact gcccgtaacg     240

gaaacgatac catccactac cgataacagc ttgcatttga aagctgatag caacaaaaat     300

cgcgatgcaa gaactattga aaatgatagt gaaattaaga gtactaataa tgctaatggc     360

tctggggcaa atcaatacac aactcttact tcaccttatc ctatgaacga cattttgtac     420

aacatgaaca atccgttaca atcaccgtca ccttcatcgg tacctcaaaa tccgactata     480

aatcctccca taaatacagc aagtaacgaa actaatttat cgcctcaaac ttcaaatggt     540

aatgaaactc ttatatctcc tcgagcccaa caacatacgt ccattaaaga taatcgtctg     600

tccttaccta atggtgctaa ttcgaatctt ttcattgaca ctaacccaaa caatttgaac     660

gaaaaactaa gaaatcaatt gaactcagat acaaattcat attctaactc catttctaat     720

tcaaactcca attctacggg taatttaaat tccagttatt ttaattcact gaacatagac     780

tccatgctag atgattacgt ttctagtgat ctcttattga atgatgatga tgatgacact     840

aatttatcac gccgaagatt tagcgacgtt ataacaaacc aatttccgtc aatgacaaat     900

tcgaggaatt ctatttctca ctctttggac ctttggaacc atccgaaaat taatccaagc     960
```

```
aatagaaata caaatctcaa tatcactact aattctacct caagttccaa tgcaagtccg   1020

aataccacta ctatgaacgc aaatgcagac tcaaatattg ctggcaaccc gaaaaacaat   1080

gacgctacca tagacaatga gttgacacag attcttaacg aatataatat gaacttcaac   1140

gataatttgg gcacatccac ttctggcaag aacaaatctg cttgcccaag ttcttttgat   1200

gccaatgcta tgacaaagat aaatccaagt cagcaattac agcaacagct aaaccgagtt   1260

caacacaagc agctcacctc gtcacataat aacagtagca ctaacatgaa atccttcaac   1320

agcgatcttt attcaagaag gcaaagagct tctttaccca taatcgatga ttcactaagc   1380

tacgacctgg ttaataagca ggatgaagac cccaagaacg atatgctgcc gaattcaaat   1440

ttgagttcat ctcaacaatt tatcaaaccg tctatgattc tttcagacaa tgcgtccgtt   1500

attgcgaaag tggcgactac aggcttgagt aatgatatgc catttttgac agaggaaggt   1560

gaacaaaatg ctaattctac tccaaatttc gatctttcca tcactcaaat gaatatggct   1620

ccattatcgc ctgcatcatc atcctccacg tctcttgcaa caaatcattt ctatcaccat   1680

ttcccacagc agggtcacca taccatgaac tctaaaatcg gttcttccct tcggaggcgg   1740

aagtctgctg tgcctttgat gggtacggtg ccgcttacaa atcaacaaaa taatataagc   1800

agtagtagtg tcaactcaac tggcaatggt gctggggtta cgaaggaaag aaggccaagt   1860

tacaggagaa aatcaatgac accgtccaga agatcaagtg tcgtaataga atcaacaaag   1920

gaactcgagg agaaaccgtt ccactgtcac atttgtccca agagctttaa gcgcagcgaa   1980

catttgaaaa ggcatgtgag atctgttcac tctaacgaac gaccatttgc ttgtcacata   2040

tgcgataaga aatttagtag aagcgataat ttgtcgcaac acatcaagac tcataaaaaa   2100

catggagaca tttaa                                                    2115
```

```
<210> SEQ ID NO 3
<211> LENGTH: 332
<212> TYPE: PRT
<213> ORGANISM: Pelodiscus sinensis japonicus

<400> SEQUENCE: 3

Met Ser Val Lys Glu Leu Leu Ile Gln Asn Val His Lys Glu Glu His
  1               5                  10                  15

Ser His Ala His Asn Lys Ile Thr Val Val Gly Val Gly Ala Val Gly
             20                  25                  30

Met Ala Cys Ala Ile Ser Ile Leu Met Lys Asp Leu Ala Asp Glu Leu
         35                  40                  45

Ala Leu Val Asp Val Ile Glu Asp Lys Leu Arg Gly Glu Met Leu Asp
     50                  55                  60

Leu Gln His Gly Ser Leu Phe Leu Arg Thr Pro Lys Ile Val Ser Gly
 65                  70                  75                  80

Lys Asp Tyr Ser Val Thr Ala His Ser Lys Leu Val Ile Ile Thr Ala
                 85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Asp Cys Met Leu Leu Val Val Ser Asn Pro Val Asp Ile Leu Thr
    130                 135                 140

Tyr Val Ala Trp Lys Ile Ser Gly Phe Pro Lys His Arg Val Ile Gly
145                 150                 155                 160
```

-continued

```
Ser Gly Cys Asn Leu Asp Ser Ala Arg Phe Arg Tyr Leu Met Gly Glu
                165                 170                 175

Lys Leu Gly Ile His Ser Leu Ser Cys His Gly Trp Ile Ile Gly Glu
            180                 185                 190

His Gly Asp Ser Ser Val Pro Val Trp Ser Gly Val Asn Val Ala Gly
        195                 200                 205

Val Ser Leu Lys Ala Leu Tyr Pro Asp Leu Gly Thr Asp Ala Asp Lys
    210                 215                 220

Glu His Trp Lys Glu Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Thr Val Met Lys Asn Leu Arg Arg Val His Pro
            260                 265                 270

Ile Ser Thr Met Val Lys Gly Met Tyr Gly Val Ser Ser Asp Val Phe
        275                 280                 285

Leu Ser Val Pro Cys Val Leu Gly Tyr Ala Gly Ile Thr Asp Val Val
    290                 295                 300

Lys Met Thr Leu Lys Ser Glu Glu Glu Glu Lys Leu Arg Lys Ser Ala
305                 310                 315                 320

Asp Thr Leu Trp Gly Ile Gln Lys Glu Leu Gln Phe
                325                 330


<210> SEQ ID NO 4
<211> LENGTH: 332
<212> TYPE: PRT
<213> ORGANISM: Ornithorhynchus anatinus

<400> SEQUENCE: 4

Met Ala Gly Val Lys Glu Gln Leu Ile Gln Asn Leu Leu Lys Glu Glu
  1               5                  10                  15

Tyr Ala Pro Gln Asn Lys Ile Thr Val Val Gly Val Gly Ala Val Gly
             20                  25                  30

Met Ala Cys Ala Ile Ser Ile Leu Met Lys Asp Leu Ala Asp Glu Leu
         35                  40                  45

Ala Leu Val Asp Val Ile Glu Asp Lys Leu Lys Gly Glu Met Met Asp
     50                  55                  60

Leu Gln His Gly Ser Leu Phe Leu Arg Thr Pro Lys Ile Val Ser Gly
 65                  70                  75                  80

Lys Asp Tyr Ser Val Thr Ala Asn Ser Lys Leu Val Ile Ile Thr Ala
                 85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Asn Cys Lys Leu Leu Val Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Ile His Ser Thr Ser Cys His Gly Trp Val Ile Gly Glu
            180                 185                 190

His Gly Asp Ser Ser Val Pro Val Trp Ser Gly Val Asn Val Ala Gly
        195                 200                 205
```

```
Val Ser Leu Lys Asn Leu His Pro Asp Leu Gly Thr Asp Ala Asp Lys
    210                 215                 220

Glu Gln Trp Lys Asp Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Val Lys Asn Leu Arg Arg Val His Pro
            260                 265                 270

Ile Ser Thr Met Ile Lys Gly Leu Tyr Gly Ile Lys Asp Glu Val Phe
        275                 280                 285

Leu Ser Val Pro Cys Val Leu Gly Gln Asn Gly Ile Ser Asp Val Val
    290                 295                 300

Lys Ile Thr Leu Lys Ser Glu Glu Glu Ala His Leu Lys Lys Ser Ala
305                 310                 315                 320

Asp Thr Leu Trp Gly Ile Gln Lys Glu Leu Gln Phe
                325                 330


<210> SEQ ID NO 5
<211> LENGTH: 332
<212> TYPE: PRT
<213> ORGANISM: Tursiops truncatus

<400> SEQUENCE: 5

Met Ala Thr Val Lys Asp Gln Leu Ile Gln Asn Leu Leu Lys Glu Glu
  1               5                  10                  15

His Val Pro Gln Asn Lys Ile Thr Val Val Gly Val Gly Ala Val Gly
            20                  25                  30

Met Ala Cys Ala Ile Ser Ile Leu Met Lys Asp Leu Ala Asp Glu Leu
        35                  40                  45

Ala Leu Val Asp Val Ile Glu Asp Lys Leu Lys Gly Glu Met Met Asp
     50                  55                  60

Leu Gln His Gly Ser Leu Phe Leu Arg Thr Pro Lys Ile Val Ser Gly
 65                  70                  75                  80

Lys Asp Tyr Ser Val Thr Ala Asn Ser Lys Leu Val Ile Ile Thr Ala
                 85                  90                  95

Gly Ala Arg Gln Gln Glu Gly Glu Ser Arg Leu Asn Leu Val Gln Arg
            100                 105                 110

Asn Val Asn Ile Phe Lys Phe Ile Val Pro Asn Ile Val Lys Tyr Ser
        115                 120                 125

Pro His Cys Lys Leu Leu Val Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Ile Leu Gly Glu
            180                 185                 190

His Gly Asp Ser Ser Val Pro Val Trp Ser Gly Val Asn Val Ala Gly
        195                 200                 205

Val Ser Leu Lys Asn Leu His Pro Glu Leu Gly Thr Asp Ala Asp Lys
    210                 215                 220

Glu His Trp Lys Ala Ile His Lys Gln Val Val Asp Ser Ala Tyr Glu
225                 230                 235                 240

Val Ile Lys Leu Lys Gly Tyr Thr Ser Trp Ala Val Gly Leu Ser Val
```

-continued

```
                245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe
        275                 280                 285

Leu Ser Val Pro Cys Ile Leu Gly Gln Asn Gly Ile Ser Asp Val Val
    290                 295                 300

Lys Val Thr Leu Thr Pro Glu Glu Gln Ala Cys Leu Lys Lys Ser Ala
305                 310                 315                 320

Asp Thr Leu Trp Gly Ile Gln Lys Glu Leu Gln Phe
                325                 330


<210> SEQ ID NO 6
<211> LENGTH: 332
<212> TYPE: PRT
<213> ORGANISM: Rattus norvegicus

<400> SEQUENCE: 6

Met Ala Ala Leu Lys Asp Gln Leu Ile Val Asn Leu Leu Lys Glu Glu
  1               5                  10                  15

Gln Val Pro Gln Asn Lys Ile Thr Val Val Gly Val Gly Ala Val Gly
             20                  25                  30

Met Ala Cys Ala Ile Ser Ile Leu Met Lys Asp Leu Ala Asp Glu Leu
         35                  40                  45

Ala Leu Val Asp Val Ile Glu Asp Lys Leu Lys Gly Glu Met Met Asp
     50                  55                  60

Leu Gln His Gly Ser Leu Phe Leu Lys Thr Pro Lys Ile Val Ser Ser
 65                  70                  75                  80

Lys Asp Tyr Ser Val Thr Ala Asn Ser Lys Leu Val Ile Ile Thr Ala
                 85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Gln Cys Lys Leu Leu Ile Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Val Leu Gly Glu
            180                 185                 190

His Gly Asp Ser Ser Val Pro Val Trp Ser Gly Val Asn Val Ala Gly
        195                 200                 205

Val Ser Leu Lys Ser Leu Asn Pro Gln Leu Gly Thr Asp Ala Asp Lys
    210                 215                 220

Glu Gln Trp Lys Asp Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe
        275                 280                 285
```

-continued

```
Leu Ser Val Pro Cys Ile Leu Gly Gln Asn Gly Ile Ser Asp Val Val
    290                 295                 300

Lys Val Thr Leu Thr Pro Asp Glu Glu Ala Arg Leu Lys Lys Ser Ala
305                 310                 315                 320

Asp Thr Leu Trp Gly Ile Gln Lys Glu Leu Gln Phe
                325                 330


<210> SEQ ID NO 7
<211> LENGTH: 332
<212> TYPE: PRT
<213> ORGANISM: Bos Taurus

<400> SEQUENCE: 7

Met Ala Thr Leu Lys Asp Gln Leu Ile Gln Asn Leu Leu Lys Glu Glu
  1               5                  10                  15

His Val Pro Gln Asn Lys Ile Thr Ile Val Gly Val Gly Ala Val Gly
             20                  25                  30

Met Ala Cys Ala Ile Ser Ile Leu Met Lys Asp Leu Ala Asp Glu Val
         35                  40                  45

Ala Leu Val Asp Val Met Glu Asp Lys Leu Lys Gly Glu Met Met Asp
     50                  55                  60

Leu Gln His Gly Ser Leu Phe Leu Arg Thr Pro Lys Ile Val Ser Gly
 65                  70                  75                  80

Lys Asp Tyr Asn Val Thr Ala Asn Ser Arg Leu Val Ile Ile Thr Ala
                 85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Ile Val Lys Tyr Ser
        115                 120                 125

Pro Asn Cys Lys Leu Leu Val Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Ile Leu Gly Glu
            180                 185                 190

His Gly Asp Ser Ser Val Pro Val Trp Ser Gly Val Asn Val Ala Gly
        195                 200                 205

Val Ser Leu Lys Asn Leu His Pro Glu Leu Gly Thr Asp Ala Asp Lys
    210                 215                 220

Glu Gln Trp Lys Ala Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe
        275                 280                 285

Leu Ser Val Pro Cys Ile Leu Gly Gln Asn Gly Ile Ser Asp Val Val
    290                 295                 300

Lys Val Thr Leu Thr His Glu Glu Glu Ala Cys Leu Lys Lys Ser Ala
305                 310                 315                 320

Asp Thr Leu Trp Gly Ile Gln Lys Glu Leu Gln Phe
                325                 330
```

-continued

<210> SEQ ID NO 8
<211> LENGTH: 999
<212> TYPE: DNA
<213> ORGANISM: Pelodiscus sinensis japonicus

<400> SEQUENCE: 8
atgtccgtaa aggaactact tatacaaaac gtccataagg aggagcattc tcacgctcac 60
aataagataa cagttgtagg agtaggtgca gtaggtatgg catgtgctat ttcgatatta 120
atgaaagact tggctgatga actagccttg gttgatgtga ttgaggataa gttacgtgga 180
gaaatgttag atttgcaaca tggttcattg ttcttgagaa cccccaaaat tgtctcgggt 240
aaggattatt cagtcactgc tcattctaaa ctggttatca ttacagcagg tgcaagacag 300
caagaagggg agagcagact aaatctggtt caacgtaatg tcaacatctt caagtttatc 360
atcccgaacg tagtaaaata cagtccagac tgcatgttgc ttgttgtgag taatccagtt 420
gacatcttaa cctatgttgc gtggaaaatc agtgggtttc caaaacatag ggtgattggc 480
tcaggatgca accttgatag cgccaggttt aggtatctaa tgggagaaaa attaggtatt 540
cactccttat cttgtcatgg ctggataata ggcgaacatg gtgattcttc ggtacctgtt 600
tggtccgggg ttaatgtggc tggtgttagt ttaaaagcat tatatcctga cctgggtact 660
gatgccgata aagaacattg gaaagaagtg cacaaacaag tggttgattc tgcttacgaa 720
gttattaaac ttaagggcta cacttcttgg gctataggtc tatcagtagc tgatttggca 780
gaaaccgtta tgaaaaattt aagaagagtc cacccaattt ccacgatggt caagggtatg 840
tacggtgtta gctctgacgt cttcttatct gttccttgtg ttttgggata tgcgggaatt 900
acagacgtcg tgaagatgac attgaaatca gaggaagagg aaaaactaag aaagtcagcc 960
gatactctgt ggggcattca aaaggaattg cagttttaa 999

<210> SEQ ID NO 9
<211> LENGTH: 999
<212> TYPE: DNA
<213> ORGANISM: Bos Taurus

<400> SEQUENCE: 9
atggcaacat taaaagatca actaatccag aatttgttga aagaggagca tgttccacaa 60
aacaaaatca caatcgtcgg cgtaggtgca gtaggtatgg cttgtgccat atccatcttg 120
atgaaagact tagctgatga ggtcgcgctg gttgatgtaa tggaggacaa acttaaagga 180
gaaatgatgg atcttcaaca tggttcactc tttttgagaa ctcctaaaat tgtatccggg 240
aaagattata acgttaccgc caattctaga cttgttataa tcacggctgg tgcaagacaa 300
caggaaggcg aatcaagact taacttagtt cagagaaacg taaacatttt caagtttatc 360
atcccaaata ttgtaaaata ctccccaaat tgcaagttgc tggttgtttc aaatcctgtt 420
gacatattga cttacgttgc ttggaagatt tcaggtttcc caaagaatag agtaatcgga 480
tctggttgca atctcgattc tgctcgtttt aggtatctga tgggtgaaag attaggggtt 540
catccattga gttgtcacgg atggattcta ggtgaacatg gagatagttc tgtgcctgtt 600
tggtcaggtg tcaacgtagc aggtgtctct ttgaaaaatc tacacccaga actaggaaca 660
gatgccgaca aggaacaatg gaaggccgtc cacaaacaag tggtggattc tgcctacgaa 720
gtcatcaaat tgaagggcta cacatcttgg gcaattggct tatccgtcgc tgatctggct 780
gaatcaataa tgaaaaacct ccgtagagtg catcctataa gtactatgat taagggttta 840
tacgggatca aggaagatgt ttttctatct gtgccatgta ttttgggcca aaatggaatt 900
tctgacgttg ttaaagtgac acttactcat gaagaggaag cgtgtttgaa aaagagcgca 960
gacaccttat ggggcatcca aaaggaatta caattctaa 999

<210> SEQ ID NO 10
<211> LENGTH: 563
<212> TYPE: PRT
<213> ORGANISM: Saccharomyces cerevisiae

<400> SEQUENCE: 10

Met Ser Glu Ile Thr Leu Gly Lys Tyr Leu Phe Glu Arg Leu Lys Gln
1 5 10 15

Val Asn Val Asn Thr Val Phe Gly Leu Pro Gly Asp Phe Asn Leu Ser
20 25 30

Leu Leu Asp Lys Ile Tyr Glu Val Glu Gly Met Arg Trp Ala Gly Asn
35 40 45

Ala Asn Glu Leu Asn Ala Ala Tyr Ala Ala Asp Gly Tyr Ala Arg Ile
50 55 60

Lys Gly Met Ser Cys Ile Ile Thr Thr Phe Gly Val Gly Glu Leu Ser
65 70 75 80

Ala Leu Asn Gly Ile Ala Gly Ser Tyr Ala Glu His Val Gly Val Leu
85 90 95

His Val Val Gly Val Pro Ser Ile Ser Ala Gln Ala Lys Gln Leu Leu
100 105 110

Leu His His Thr Leu Gly Asn Gly Asp Phe Thr Val Phe His Arg Met
115 120 125

Ser Ala Asn Ile Ser Glu Thr Thr Ala Met Ile Thr Asp Ile Ala Thr
130 135 140

Ala Pro Ala Glu Ile Asp Arg Cys Ile Arg Thr Thr Tyr Val Thr Gln
145 150 155 160

Arg Pro Val Tyr Leu Gly Leu Pro Ala Asn Leu Val Asp Leu Asn Val
165 170 175

Pro Ala Lys Leu Leu Gln Thr Pro Ile Asp Met Ser Leu Lys Pro Asn
180 185 190

Asp Ala Glu Ser Glu Lys Glu Val Ile Asp Thr Ile Leu Ala Leu Val
195 200 205

Lys Asp Ala Lys Asn Pro Val Ile Leu Ala Asp Ala Cys Cys Ser Arg
210 215 220

His Asp Val Lys Ala Glu Thr Lys Lys Leu Ile Asp Leu Thr Gln Phe
225 230 235 240

Pro Ala Phe Val Thr Pro Met Gly Lys Gly Ser Ile Asp Glu Gln His
245 250 255

Pro Arg Tyr Gly Gly Val Tyr Val Gly Thr Leu Ser Lys Pro Glu Val
260 265 270

Lys Glu Ala Val Glu Ser Ala Asp Leu Ile Leu Ser Val Gly Ala Leu
275 280 285

Leu Ser Asp Phe Asn Thr Gly Ser Phe Ser Tyr Ser Tyr Lys Thr Lys
290 295 300

Asn Ile Val Glu Phe His Ser Asp His Met Lys Ile Arg Asn Ala Thr
305 310 315 320

Phe Pro Gly Val Gln Met Lys Phe Val Leu Gln Lys Leu Leu Thr Thr
325 330 335

Ile Ala Asp Ala Ala Lys Gly Tyr Lys Pro Val Ala Val Pro Ala Arg
340 345 350

-continued

Thr Pro Ala Asn Ala Ala Val Pro Ala Ser Thr Pro Leu Lys Gln Glu
355 360 365

Trp Met Trp Asn Gln Leu Gly Asn Phe Leu Gln Glu Gly Asp Val Val
370 375 380

Ile Ala Glu Thr Gly Thr Ser Ala Phe Gly Ile Asn Gln Thr Thr Phe
385 390 395 400

Pro Asn Asn Thr Tyr Gly Ile Ser Gln Val Leu Trp Gly Ser Ile Gly
405 410 415

Phe Thr Thr Gly Ala Thr Leu Gly Ala Ala Phe Ala Ala Glu Glu Ile
420 425 430

Asp Pro Lys Lys Arg Val Ile Leu Phe Ile Gly Asp Gly Ser Leu Gln
435 440 445

Leu Thr Val Gln Glu Ile Ser Thr Met Ile Arg Trp Gly Leu Lys Pro
450 455 460

Tyr Leu Phe Val Leu Asn Asn Asp Gly Tyr Thr Ile Glu Lys Leu Ile
465 470 475 480

His Gly Pro Lys Ala Gln Tyr Asn Glu Ile Gln Gly Trp Asp His Leu
485 490 495

Ser Leu Leu Pro Thr Phe Gly Ala Lys Asp Tyr Glu Thr His Arg Val
500 505 510

Ala Thr Thr Gly Glu Trp Asp Lys Leu Thr Gln Asp Lys Ser Phe Asn
515 520 525

Asp Asn Ser Lys Ile Arg Met Ile Glu Ile Met Leu Pro Val Phe Asp
530 535 540

Ala Pro Gln Asn Leu Val Glu Gln Ala Lys Leu Thr Ala Ala Thr Asn
545 550 555 560

Ala Lys Gln

<210> SEQ ID NO 11
<211> LENGTH: 1692
<212> TYPE: DNA
<213> ORGANISM: Saccharomyces cerevisiae

<400> SEQUENCE: 11
atgtctgaaa ttactttggg taaatatttg ttcgaaagat taaagcaagt caacgttaac 60
accgttttcg gtttgccagg tgacttcaac ttgtccttgt tggacaagat ctacgaagtt 120
gaaggtatga gatgggctgg taacgccaac gaattgaacg ctgcttacgc cgctgatggt 180
tacgctcgta tcaagggtat gtcttgtatc atcaccacct tcggtgtcgg tgaattgtct 240
gctttgaacg gtattgccgg ttcttacgct gaacacgtcg gtgttttgca cgttgttggt 300
gtcccatcca tctctgctca agctaagcaa ttgttgttgc accacacctt gggtaacggt 360
gacttcactg ttttccacag aatgtctgcc aacatttctg aaaccactgc tatgatcact 420
gacattgcta ccgccccagc tgaaattgac agatgtatca gaaccactta cgtcacccaa 480
agaccagtct acttaggttt gccagctaac ttggtcgact tgaacgtccc agctaagttg 540
ttgcaaactc caattgacat gtctttgaag ccaaacgatg ctgaatccga aaaggaagtc 600
attgacacca tcttggcttt ggtcaaggat gctaagaacc cagttatctt ggctgatgct 660
tgttgttcca gacacgacgt caaggctgaa actaagaagt tgattgactt gactcaattc 720
ccagctttcg tcaccccaat gggtaagggt tccattgacg aacaacaccc aagatacggt 780
ggtgtttacg tcggtacctt gtccaagcca gaagttaagg aagccgttga atctgctgac 840
ttgattttgt ctgtcggtgc tttgttgtct gatttcaaca ccggttcttt ctcttactct 900

-continued

```
tacaagacca agaacattgt cgaattccac tccgaccaca tgaagatcag aaacgccact    960

ttcccaggtg tccaaatgaa attcgttttg caaaagttgt tgaccactat tgctgacgcc   1020

gctaagggtt acaagccagt tgctgtccca gctagaactc cagctaacgc tgctgtccca   1080

gcttctaccc cattgaagca agaatggatg tggaaccaat tgggtaactt cttgcaagaa   1140

ggtgatgttg tcattgctga aaccggtacc tccgctttcg gtatcaacca aaccactttc   1200

ccaaacaaca cctacggtat ctctcaagtc ttatggggtt ccattggttt caccactggt   1260

gctaccttgg gtgctgcttt cgctgctgaa gaaattgatc caaagaagag agttatctta   1320

ttcattggtg acggttcttt gcaattgact gttcaagaaa tctccaccat gatcagatgg   1380

ggcttgaagc catacttgtt cgtcttgaac aacgatggtt acaccattga aaagttgatt   1440

cacggtccaa aggctcaata caacgaaatt caaggttggg accacctatc cttgttgcca   1500

actttcggtg ctaaggacta tgaaacccac agagtcgcta ccaccggtga atgggacaag   1560

ttgacccaag acaagtcttt caacgacaac tctaagatca gaatgattga aatcatgttg   1620

ccagtcttcg atgctccaca aaacttggtt gaacaagcta agttgactgc tgctaccaac   1680

gctaagcaat aa                                                       1692
```

<210> SEQ ID NO 12
<211> LENGTH: 591
<212> TYPE: PRT
<213> ORGANISM: Saccharomyces cerevisiae

<400> SEQUENCE: 12

```
Met Leu Lys Tyr Lys Pro Leu Leu Lys Ile Ser Lys Asn Cys Glu Ala
  1               5                  10                  15

Ala Ile Leu Arg Ala Ser Lys Thr Arg Leu Asn Thr Ile Arg Ala Tyr
             20                  25                  30

Gly Ser Thr Val Pro Lys Ser Lys Ser Phe Glu Gln Asp Ser Arg Lys
         35                  40                  45

Arg Thr Gln Ser Trp Thr Ala Leu Arg Val Gly Ala Ile Leu Ala Ala
     50                  55                  60

Thr Ser Ser Val Ala Tyr Leu Asn Trp His Asn Gly Gln Ile Asp Asn
 65                  70                  75                  80

Glu Pro Lys Leu Asp Met Asn Lys Gln Lys Ile Ser Pro Ala Glu Val
                 85                  90                  95

Ala Lys His Asn Lys Pro Asp Asp Cys Trp Val Val Ile Asn Gly Tyr
            100                 105                 110

Val Tyr Asp Leu Thr Arg Phe Leu Pro Asn His Pro Gly Gly Gln Asp
        115                 120                 125

Val Ile Lys Phe Asn Ala Gly Lys Asp Val Thr Ala Ile Phe Glu Pro
    130                 135                 140

Leu His Ala Pro Asn Val Ile Asp Lys Tyr Ile Ala Pro Glu Lys Lys
145                 150                 155                 160

Leu Gly Pro Leu Gln Gly Ser Met Pro Pro Glu Leu Val Cys Pro Pro
                165                 170                 175

Tyr Ala Pro Gly Glu Thr Lys Glu Asp Ile Ala Arg Lys Glu Gln Leu
            180                 185                 190

Lys Ser Leu Leu Pro Pro Leu Asp Asn Ile Ile Asn Leu Tyr Asp Phe
        195                 200                 205

Glu Tyr Leu Ala Ser Gln Thr Leu Thr Lys Gln Ala Trp Ala Tyr Tyr
    210                 215                 220
```

-continued

```
Ser Ser Gly Ala Asn Asp Glu Val Thr His Arg Glu Asn His Asn Ala
225                 230                 235                 240

Tyr His Arg Ile Phe Phe Lys Pro Lys Ile Leu Val Asp Val Arg Lys
                245                 250                 255

Val Asp Ile Ser Thr Asp Met Leu Gly Ser His Val Asp Val Pro Phe
            260                 265                 270

Tyr Val Ser Ala Thr Ala Leu Cys Lys Leu Gly Asn Pro Leu Glu Gly
        275                 280                 285

Glu Lys Asp Val Ala Arg Gly Cys Gly Gln Gly Val Thr Lys Val Pro
    290                 295                 300

Gln Met Ile Ser Thr Leu Ala Ser Cys Ser Pro Glu Glu Ile Ile Glu
305                 310                 315                 320

Ala Ala Pro Ser Asp Lys Gln Ile Gln Trp Tyr Gln Leu Tyr Val Asn
                325                 330                 335

Ser Asp Arg Lys Ile Thr Asp Asp Leu Val Lys Asn Val Glu Lys Leu
            340                 345                 350

Gly Val Lys Ala Leu Phe Val Thr Val Asp Ala Pro Ser Leu Gly Gln
        355                 360                 365

Arg Glu Lys Asp Met Lys Leu Lys Phe Ser Asn Thr Lys Ala Gly Pro
    370                 375                 380

Lys Ala Met Lys Lys Thr Asn Val Glu Glu Ser Gln Gly Ala Ser Arg
385                 390                 395                 400

Ala Leu Ser Lys Phe Ile Asp Pro Ser Leu Thr Trp Lys Asp Ile Glu
                405                 410                 415

Glu Leu Lys Lys Lys Thr Lys Leu Pro Ile Val Ile Lys Gly Val Gln
            420                 425                 430

Arg Thr Glu Asp Val Ile Lys Ala Ala Glu Ile Gly Val Ser Gly Val
        435                 440                 445

Val Leu Ser Asn His Gly Gly Arg Gln Leu Asp Phe Ser Arg Ala Pro
    450                 455                 460

Ile Glu Val Leu Ala Glu Thr Met Pro Ile Leu Glu Gln Arg Asn Leu
465                 470                 475                 480

Lys Asp Lys Leu Glu Val Phe Val Asp Gly Gly Val Arg Arg Gly Thr
                485                 490                 495

Asp Val Leu Lys Ala Leu Cys Leu Gly Ala Lys Gly Val Gly Leu Gly
            500                 505                 510

Arg Pro Phe Leu Tyr Ala Asn Ser Cys Tyr Gly Arg Asn Gly Val Glu
        515                 520                 525

Lys Ala Ile Glu Ile Leu Arg Asp Glu Ile Glu Met Ser Met Arg Leu
    530                 535                 540

Leu Gly Val Thr Ser Ile Ala Glu Leu Lys Pro Asp Leu Leu Asp Leu
545                 550                 555                 560

Ser Thr Leu Lys Ala Arg Thr Val Gly Val Pro Asn Asp Val Leu Tyr
                565                 570                 575

Asn Glu Val Tyr Glu Gly Pro Thr Leu Thr Glu Phe Glu Asp Ala
            580                 585                 590


<210> SEQ ID NO 13
<211> LENGTH: 1776
<212> TYPE: DNA
<213> ORGANISM: Saccharomyces cerevisiae

<400> SEQUENCE: 13

atgctaaaat acaaaccttt actaaaaatc tcgaagaact gtgaggctgc tatcctcaga     60
```

```
gcgtctaaga ctagattgaa cacaatccgc gcgtacggtt ctaccgttcc aaaatccaag    120

tcgttcgaac aagactcaag aaaacgcaca cagtcatgga ctgccttgag agtcggtgca    180

attctagccg ctactagttc cgtggcgtat ctaaactggc ataatggcca aatagacaac    240

gagccgaaac tggatatgaa taaacaaaag atttcgcccg ctgaagttgc caagcataac    300

aagcccgatg attgttgggt tgtgatcaat ggttacgtat acgacttaac gcgattccta    360

ccaaatcatc caggtgggca ggatgttatc aagtttaacg ccgggaaaga tgtcactgct    420

atttttgaac cactacatgc tcctaatgtc atcgataagt atatagctcc cgagaaaaaa    480

ttgggtcccc ttcaaggatc catgcctcct gaacttgtct gtcctcctta tgctcctggt    540

gaaactaagg aagatatcgc tagaaaagaa caactaaaat cgctgctacc tcctctagat    600

aatattatta acctttacga ctttgaatac ttggcctctc aaactttgac taaacaagcg    660

tgggcctact attcctccgg tgctaacgac gaagttactc acagagaaaa ccataatgct    720

tatcatagga tttttttcaa accaaagatc cttgtagatg tacgcaaagt agacatttca    780

actgacatgt tgggttctca tgtggatgtt cccttctacg tgtctgctac agctttgtgt    840

aaactgggaa acccccttaga aggtgaaaaa gatgtcgcca gaggttgtgg ccaaggtgtg    900

acaaaagtcc cacaaatgat atctactttg gcttcatgtt cccctgagga aattattgaa    960

gcagcaccct ctgataaaca aattcaatgg taccaactat atgttaactc tgatagaaag   1020

atcactgatg atttggttaa aaatgtagaa aagctgggtg taaaggcatt atttgtcact   1080

gtggatgctc caagtttagg tcaaagagaa aaagatatga agctgaaatt ttccaataca   1140

aaggctggtc caaaagcgat gaagaaaact aatgtagaag aatctcaagg tgcttcgaga   1200

gcgttatcaa agtttattga cccctctttg acttggaaag atatagaaga gttgaagaaa   1260

aagacaaaac tacctattgt tatcaaaggt gttcaacgta ccgaagatgt tatcaaagca   1320

gcagaaatcg gtgtaagtgg ggtggttcta tccaatcatg gtggtagaca attagatttt   1380

tcaagggctc ccattgaagt cctggctgaa accatgccaa tcctggaaca acgtaacttg   1440

aaggataagt tggaagtttt cgtggacggt ggtgttcgtc gtggtacaga tgtcttgaaa   1500

gcgttatgtc taggtgctaa aggtgttggt ttgggtagac cattcttgta tgcgaactca   1560

tgctatggtc gtaatggtgt tgaaaaagcc attgaaattt taagagatga aattgaaatg   1620

tctatgagac tattaggtgt tactagcatt gcggaattga agcctgatct tttagatcta   1680

tcaacactaa aggcaagaac agttggagta ccaaacgacg tgctgtataa tgaagtttat   1740

gagggaccta ctttaacaga atttgaggat gcatga                             1776
```

<210> SEQ ID NO 14
<211> LENGTH: 391
<212> TYPE: PRT
<213> ORGANISM: Saccharomyces cerevisiae

<400> SEQUENCE: 14

```
Met Ser Ala Ala Ala Asp Arg Leu Asn Leu Thr Ser Gly His Leu Asn
  1               5                  10                  15

Ala Gly Arg Lys Arg Ser Ser Ser Ser Val Ser Leu Lys Ala Ala Glu
             20                  25                  30

Lys Pro Phe Lys Val Thr Val Ile Gly Ser Gly Asn Trp Gly Thr Thr
         35                  40                  45

Ile Ala Lys Val Val Ala Glu Asn Cys Lys Gly Tyr Pro Glu Val Phe
     50                  55                  60

Ala Pro Ile Val Gln Met Trp Val Phe Glu Glu Glu Ile Asn Gly Glu
```

```
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390
```

<210> SEQ ID NO 15
<211> LENGTH: 1176
<212> TYPE: DNA
<213> ORGANISM: Saccharomyces cerevisiae

<400> SEQUENCE: 15

```
atgtctgctg ctgctgatag attaaactta acttccggcc acttgaatgc tggtagaaag      60

agaagttcct cttctgtttc tttgaaggct gccgaaaagc ctttcaaggt tactgtgatt     120

ggatctggta actggggtac tactattgcc aaggtggttg ccgaaaattg taagggatac     180

ccagaagttt tcgctccaat agtacaaatg tgggtgttcg aagaagagat caatggtgaa     240

aaattgactg aaatcataaa tactagacat caaaacgtga aatacttgcc tggcatcact     300
```

-continued

```
ctacccgaca atttggttgc taatccagac ttgattgatt cagtcaagga tgtcgacatc    360

atcgttttca acattccaca tcaatttttg ccccgtatct gtagccaatt gaaaggtcat    420

gttgattcac acgtcagagc tatctcctgt ctaaagggtt ttgaagttgg tgctaaaggt    480

gtccaattgc tatcctctta catcactgag gaactaggta ttcaatgtgg tgctctatct    540

ggtgctaaca ttgccaccga agtcgctcaa gaacactggt ctgaaacaac agttgcttac    600

cacattccaa aggatttcag aggcgagggc aaggacgtcg accataaggt tctaaaggcc    660

ttgttccaca gaccttactt ccacgttagt gtcatcgaag atgttgctgg tatctccatc    720

tgtggtgctt tgaagaacgt tgttgcctta ggttgtggtt tcgtcgaagg tctaggctgg    780

ggtaacaacg cttctgctgc catccaaaga gtcggtttgg gtgagatcat cagattcggt    840

caaatgtttt tcccagaatc tagagaagaa acatactacc aagagtctgc tggtgttgct    900

gatttgatca ccacctgcgc tggtggtaga aacgtcaagg ttgctaggct aatggctact    960

tctggtaagg acgcctggga atgtgaaaag gagttgttga atggccaatc cgctcaaggt   1020

ttaattacct gcaaagaagt tcacgaatgg ttggaaacat gtggctctgt cgaagacttc   1080

ccattatttg aagccgtata ccaaatcgtt tacaacaact acccaatgaa gaacctgccg   1140

gacatgattg aagaattaga tctacatgaa gattag                             1176
```

<210> SEQ ID NO 16
<211> LENGTH: 348
<212> TYPE: PRT
<213> ORGANISM: Saccharomyces cerevisiae

<400> SEQUENCE: 16

```
Met Ser Ile Pro Glu Thr Gln Lys Gly Val Ile Phe Tyr Glu Ser His
  1               5                  10                  15

Gly Lys Leu Glu Tyr Lys Asp Ile Pro Val Pro Lys Pro Lys Ala Asn
             20                  25                  30

Glu Leu Leu Ile Asn Val Lys Tyr Ser Gly Val Cys His Thr Asp Leu
         35                  40                  45

His Ala Trp His Gly Asp Trp Pro Leu Pro Val Lys Leu Pro Leu Val
     50                  55                  60

Gly Gly His Glu Gly Ala Gly Val Val Val Gly Met Gly Glu Asn Val
 65                  70                  75                  80

Lys Gly Trp Lys Ile Gly Asp Tyr Ala Gly Ile Lys Trp Leu Asn Gly
                 85                  90                  95

Ser Cys Met Ala Cys Glu Tyr Cys Glu Leu Gly Asn Glu Ser Asn Cys
            100                 105                 110

Pro His Ala Asp Leu Ser Gly Tyr Thr His Asp Gly Ser Phe Gln Gln
        115                 120                 125

Tyr Ala Thr Ala Asp Ala Val Gln Ala Ala His Ile Pro Gln Gly Thr
    130                 135                 140

Asp Leu Ala Gln Val Ala Pro Ile Leu Cys Ala Gly Ile Thr Val Tyr
145                 150                 155                 160

Lys Ala Leu Lys Ser Ala Asn Leu Met Ala Gly His Trp Val Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Gly Ile Asp Gly Gly Glu Gly Lys Glu
        195                 200                 205

Glu Leu Phe Arg Ser Ile Gly Gly Glu Val Phe Ile Asp Phe Thr Lys
```

210 215 220

Glu Lys Asp Ile Val Gly Ala Val Leu Lys Ala Thr Asp Gly Gly Ala
225 230 235 240

His Gly Val Ile Asn Val Ser Val Ser Glu Ala Ala Ile Glu Ala Ser
245 250 255

Thr Arg Tyr Val Arg Ala Asn Gly Thr Thr Val Leu Val Gly Met Pro
260 265 270

Ala Gly Ala Lys Cys Cys Ser Asp Val Phe Asn Gln Val Val Lys Ser
275 280 285

Ile Ser Ile Val Gly Ser Tyr Val Gly Asn Arg Ala Asp Thr Arg Glu
290 295 300

Ala Leu Asp Phe Phe Ala Arg Gly Leu Val Lys Ser Pro Ile Lys Val
305 310 315 320

Val Gly Leu Ser Thr Leu Pro Glu Ile Tyr Glu Lys Met Glu Lys Gly
325 330 335

Gln Ile Val Gly Arg Tyr Val Val Asp Thr Ser Lys
340 345

<210> SEQ ID NO 17
<211> LENGTH: 1047
<212> TYPE: DNA
<213> ORGANISM: Saccharomyces cerevisiae

<400> SEQUENCE: 17
atgtctatcc cagaaactca aaaaggtgtt atcttctacg aatcccacgg taagttggaa 60
tacaaagata ttccagttcc aaagccaaag gccaacgaat tgttgatcaa cgttaaatac 120
tctggtgtct gtcacactga cttgcacgct tggcacggtg actggccatt gccagttaag 180
ctaccattag tcggtggtca cgaaggtgcc ggtgtcgttg tcggcatggg tgaaaacgtt 240
aagggctgga agatcggtga ctacgccggt atcaaatggt tgaacggttc ttgtatggcc 300
tgtgaatact gtgaattggg taacgaatcc aactgtcctc acgctgactt gtctggttac 360
acccacgacg gttctttcca acaatacgct accgctgacg ctgttcaagc cgctcacatt 420
cctcaaggta ccgacttggc ccaagtcgcc cccatcttgt gtgctggtat caccgtctac 480
aaggctttga agtctgctaa cttgatggcc ggtcactggg ttgctatctc cggtgctgct 540
ggtggtctag gttctttggc tgttcaatac gccaaggcta tgggttacag agtcttgggt 600
attgacggtg gtgaaggtaa ggaagaatta ttcagatcca tcggtggtga agtcttcatt 660
gacttcacta aggaaaagga cattgtcggt gctgttctaa aggccactga cggtggtgct 720
cacggtgtca tcaacgtttc cgtttccgaa gccgctattg aagcttctac cagatacgtt 780
agagctaacg gtaccaccgt tttggtcggt atgccagctg gtgccaagtg ttgttctgat 840
gtcttcaacc aagtcgtcaa gtccatctct attgttggtt cttacgtcgg taacagagct 900
gacaccagag aagctttgga cttcttcgcc agaggtttgg tcaagtctcc aatcaaggtt 960
gtcggcttgt ctaccttgcc agaaatttac gaaaagatgg aaaagggtca aatcgttggt 1020
agatacgttg ttgacacttc taaataa 1047

<210> SEQ ID NO 18
<211> LENGTH: 500
<212> TYPE: PRT
<213> ORGANISM: Saccharomyces cerevisiae

<400> SEQUENCE: 18

Met Thr Lys Leu His Phe Asp Thr Ala Glu Pro Val Lys Ile Thr Leu

-continued

```
1               5                   10                  15

Pro Asn Gly Leu Thr Tyr Glu Gln Pro Thr Gly Leu Phe Ile Asn Asn
            20                  25                  30

Lys Phe Met Lys Ala Gln Asp Gly Lys Thr Tyr Pro Val Glu Asp Pro
        35                  40                  45

Ser Thr Glu Asn Thr Val Cys Glu Val Ser Ser Ala Thr Thr Glu Asp
    50                  55                  60

Val Glu Tyr Ala Ile Glu Cys Ala Asp Arg Ala Phe His Asp Thr Glu
65                  70                  75                  80

Trp Ala Thr Gln Asp Pro Arg Glu Arg Gly Arg Leu Leu Ser Lys Leu
                85                  90                  95

Ala Asp Glu Leu Glu Ser Gln Ile Asp Leu Val Ser Ser Ile Glu Ala
            100                 105                 110

Leu Asp Asn Gly Lys Thr Leu Ala Leu Ala Arg Gly Asp Val Thr Ile
        115                 120                 125

Ala Ile Asn Cys Leu Arg Asp Ala Ala Ala Tyr Ala Asp Lys Val Asn
    130                 135                 140

Gly Arg Thr Ile Asn Thr Gly Asp Gly Tyr Met Asn Phe Thr Thr Leu
145                 150                 155                 160

Glu Pro Ile Gly Val Cys Gly Gln Ile Ile Pro Trp Asn Phe Pro Ile
                165                 170                 175

Met Met Leu Ala Trp Lys Ile Ala Pro Ala Leu Ala Met Gly Asn Val
            180                 185                 190

Cys Ile Leu Lys Pro Ala Ala Val Thr Pro Leu Asn Ala Leu Tyr Phe
        195                 200                 205

Ala Ser Leu Cys Lys Lys Val Gly Ile Pro Ala Gly Val Val Asn Ile
    210                 215                 220

Val Pro Gly Pro Gly Arg Thr Val Gly Ala Ala Leu Thr Asn Asp Pro
225                 230                 235                 240

Arg Ile Arg Lys Leu Ala Phe Thr Gly Ser Thr Glu Val Gly Lys Ser
                245                 250                 255

Val Ala Val Asp Ser Ser Glu Ser Asn Leu Lys Lys Ile Thr Leu Glu
            260                 265                 270

Leu Gly Gly Lys Ser Ala His Leu Val Phe Asp Asp Ala Asn Ile Lys
        275                 280                 285

Lys Thr Leu Pro Asn Leu Val Asn Gly Ile Phe Lys Asn Ala Gly Gln
    290                 295                 300

Ile Cys Ser Ser Gly Ser Arg Ile Tyr Val Gln Glu Gly Ile Tyr Asp
305                 310                 315                 320

Glu Leu Leu Ala Ala Phe Lys Ala Tyr Leu Glu Thr Glu Ile Lys Val
                325                 330                 335

Gly Asn Pro Phe Asp Lys Ala Asn Phe Gln Gly Ala Ile Thr Asn Arg
            340                 345                 350

Gln Gln Phe Asp Thr Ile Met Asn Tyr Ile Asp Ile Gly Lys Lys Glu
        355                 360                 365

Gly Ala Lys Ile Leu Thr Gly Gly Glu Lys Val Gly Asp Lys Gly Tyr
    370                 375                 380

Phe Ile Arg Pro Thr Val Phe Tyr Asp Val Asn Glu Asp Met Arg Ile
385                 390                 395                 400

Val Lys Glu Glu Ile Phe Gly Pro Val Val Thr Val Ala Lys Phe Lys
                405                 410                 415

Thr Leu Glu Glu Gly Val Glu Met Ala Asn Ser Ser Glu Phe Gly Leu
            420                 425                 430
```

-continued

```
Gly Ser Gly Ile Glu Thr Glu Ser Leu Ser Thr Gly Leu Lys Val Ala
        435                 440                 445

Lys Met Leu Lys Ala Gly Thr Val Trp Ile Asn Thr Tyr Asn Asp Phe
    450                 455                 460

Asp Ser Arg Val Pro Phe Gly Gly Val Lys Gln Ser Gly Tyr Gly Arg
465                 470                 475                 480

Glu Met Gly Glu Glu Val Tyr His Ala Tyr Thr Glu Val Lys Ala Val
                485                 490                 495

Arg Ile Lys Leu
            500


<210> SEQ ID NO 19
<211> LENGTH: 1503
<212> TYPE: DNA
<213> ORGANISM: Saccharomyces cerevisiae

<400> SEQUENCE: 19

atgactaagc tacactttga cactgctgaa ccagtcaaga tcacacttcc aaatggtttg      60

acatacgagc aaccaaccgg tctattcatt aacaacaagt ttatgaaagc tcaagacggt     120

aagacctatc ccgtcgaaga tccttccact gaaaacaccg tttgtgaggt ctcttctgcc     180

accactgaag atgttgaata tgctatcgaa tgtgccgacc gtgctttcca cgacactgaa     240

tgggctaccc aagacccaag agaaagaggc cgtctactaa gtaagttggc tgacgaattg     300

gaaagccaaa ttgacttggt ttcttccatt gaagctttgg acaatggtaa aactttggcc     360

ttagcccgtg gggatgttac cattgcaatc aactgtctaa gagatgctgc tgcctatgcc     420

gacaaagtca acggtagaac aatcaacacc ggtgacggct acatgaactt caccacctta     480

gagccaatcg gtgtctgtgg tcaaattatt ccatggaact ttccaataat gatgttggct     540

tggaagatcg ccccagcatt ggccatgggt aacgtctgta tcttgaaacc cgctgctgtc     600

acacctttaa atgccctata ctttgcttct ttatgtaaga aggttggtat tccagctggt     660

gtcgtcaaca tcgttccagg tcctggtaga actgttggtg ctgctttgac caacgaccca     720

agaatcagaa agctggcttt taccggttct acagaagtcg gtaagagtgt tgctgtcgac     780

tcttctgaat ctaacttgaa gaaaatcact ttggaactag gtggtaagtc cgcccatttg     840

gtctttgacg atgctaacat taagaagact ttaccaaatc tagtaaacgg tattttcaag     900

aacgctggtc aaatttgttc ctctggttct agaatttacg ttcaagaagg tatttacgac     960

gaactattgg ctgctttcaa ggcttacttg gaaaccgaaa tcaaagttgg taatccattt    1020

gacaaggcta acttccaagg tgctatcact aaccgtcaac aattcgacac aattatgaac    1080

tacatcgata tcggtaagaa agaaggcgcc aagatcttaa ctggtggcga aaaagttggt    1140

gacaagggtt acttcatcag accaaccgtt ttctacgatg ttaatgaaga catgagaatt    1200

gttaaggaag aaatttttgg accagttgtc actgtcgcaa agttcaagac tttagaagaa    1260

ggtgtcgaaa tggctaacag ctctgaattc ggtctaggtt ctggtatcga aacagaatct    1320

ttgagcacag gtttgaaggt ggccaagatg ttgaaggccg gtaccgtctg gatcaacaca    1380

tacaacgatt ttgactccag agttccattc ggtggtgtta agcaatctgg ttacggtaga    1440

gaaatgggtg aagaagtcta ccatgcatac actgaagtaa aagctgtcag aattaagttg    1500

taa                                                                   1503


<210> SEQ ID NO 20
<211> LENGTH: 316
```

-continued

<212> TYPE: PRT
<213> ORGANISM: Escherichia coli

<400> SEQUENCE: 20

Met Ser Lys Arg Lys Val Ala Ile Ile Gly Ser Gly Asn Ile Gly Thr
1 5 10 15

Asp Leu Met Ile Lys Ile Leu Arg His Gly Gln His Leu Glu Met Ala
20 25 30

Val Met Val Gly Ile Asp Pro Gln Ser Asp Gly Leu Ala Arg Ala Arg
35 40 45

Arg Met Gly Val Ala Thr Thr His Glu Gly Val Ile Gly Leu Met Asn
50 55 60

Met Pro Glu Phe Ala Asp Ile Asp Ile Val Phe Asp Ala Thr Ser Ala
65 70 75 80

Gly Ala His Val Lys Asn Asp Ala Ala Leu Arg Glu Ala Lys Pro Asp
85 90 95

Ile Arg Leu Ile Asp Leu Thr Pro Ala Ala Ile Gly Pro Tyr Cys Val
100 105 110

Pro Val Val Asn Leu Glu Ala Asn Val Asp Gln Leu Asn Val Asn Met
115 120 125

Val Thr Cys Gly Gly Gln Ala Thr Ile Pro Met Val Ala Ala Val Ser
130 135 140

Arg Val Ala Arg Val His Tyr Ala Glu Ile Ile Ala Ser Ile Ala Ser
145 150 155 160

Lys Ser Ala Gly Pro Gly Thr Arg Ala Asn Ile Asp Glu Phe Thr Glu
165 170 175

Thr Thr Ser Arg Ala Ile Glu Val Val Gly Gly Ala Ala Lys Gly Lys
180 185 190

Ala Ile Ile Val Leu Asn Pro Ala Glu Pro Pro Leu Met Met Arg Asp
195 200 205

Thr Val Tyr Val Leu Ser Asp Glu Ala Ser Gln Asp Asp Ile Glu Ala
210 215 220

Ser Ile Asn Glu Met Ala Glu Ala Val Gln Ala Tyr Val Pro Gly Tyr
225 230 235 240

Arg Leu Lys Gln Arg Val Gln Phe Glu Val Ile Pro Gln Asp Lys Pro
245 250 255

Val Asn Leu Pro Gly Val Gly Gln Phe Ser Gly Leu Lys Thr Ala Val
260 265 270

Trp Leu Glu Val Glu Gly Ala Ala His Tyr Leu Pro Ala Tyr Ala Gly
275 280 285

Asn Leu Asp Ile Met Thr Ser Ser Ala Leu Ala Thr Ala Glu Lys Met
290 295 300

Ala Gln Ser Leu Ala Arg Lys Ala Gly Glu Ala Ala
305 310 315

<210> SEQ ID NO 21
<211> LENGTH: 951
<212> TYPE: DNA
<213> ORGANISM: Escherichia coli

<400> SEQUENCE: 21
atgagtaagc gtaaagtcgc cattatcggt tctggcaaca ttggtaccga tctgatgatt 60
aaaattttgc gtcacggtca gcatctggag atggcggtga tggttggcat tgatcctcag 120
tccgacggtc tggcgcgcgc cagacgtatg ggcgtcgcca ccacccatga aggggtgatc 180

-continued

```
ggactgatga acatgcctga atttgctgat atcgacattg tatttgatgc gaccagcgcc    240

ggtgctcatg tgaaaaacga tgccgcttta cgcgaagcga aaccggatat tcgcttaatt    300

gacctgacgc ctgctgccat cggcccttac tgcgtgccgg tggttaacct cgaggcgaac    360

gtcgatcaac tgaacgtcaa catggtcacc tgcggcggcc aggccaccat tccaatggtg    420

gcggcagttt cacgcgtggc gcgtgttcat tacgccgaaa ttatcgcttc tatcgccagt    480

aaatctgccg gacctggcac gcgtgccaat atcgatgaat ttacggaaac cacttcccga    540

gccattgaag tggtgggcgg cgcggcaaaa gggaaggcga ttattgtgct taacccagca    600

gagccaccgt tgatgatgcg tgacacggtg tatgtattga gcgacgaagc ttcacaagat    660

gatatcgaag cctcaatcaa tgaaatggct gaggcggtgc aggcttacgt accgggttat    720

cgcctgaaac agcgcgtgca gtttgaagtt atcccgcagg ataaaccggt caatttaccg    780

ggcgtggggc aattctccgg actgaaaaca gcggtctggc tggaagtcga aggcgcagcg    840

cattatctgc ctgcctatgc gggcaacctc gacattatga cttccagtgc gctggcgaca    900

gcggaaaaaa tggcccagtc actggcgcgc aaggcaggag aagcggcatg a             951
```

<210> SEQ ID NO 22
<211> LENGTH: 954
<212> TYPE: DNA
<213> ORGANISM: Artificial Sequence
<220> FEATURE:
<223> OTHER INFORMATION: Synthetic Saccharomyces cerevisiae optimized MhpF

<400> SEQUENCE: 22

```
atgtcaaagc gaaaagtagc tatcataggt tcaggtaata ttggtactga tttgatgatc     60

aaaatcctga gacatggcca gcacttggag atggccgtca tggttggtat cgacccacaa    120

tccgatggct tagctagagc taggagaatg ggtgttgcca caactcacga aggggttatt    180

ggcttaatga acatgccaga atttgcagac atcgatatag tttttgatgc tactagtgca    240

ggggcacatg tgaaaaacga cgcggcttta agagaagcca agccagatat tagattaatt    300

gatcttaccc ctgctgctat aggtccttac tgcgttcctg tagttaacct tgaagctaat    360

gtggaccagt tgaacgtgaa tatggttaca tgtggtggcc aagctaccat accaatggtt    420

gctgctgtct ctagagtggc cagagtacat tatgccgaga tcattgcgtc tatcgcatct    480

aagtctgccg gtcctggaac aagggctaac atcgatgagt tcactgagac aacctctaga    540

gctatcgaag tagtaggagg cgcagcaaaa ggtaaagcga tcattgtttt gaatcctgcc    600

gaaccacctt tgatgatgag agatacggtc tacgtgctat cagatgaagc ttcccaggat    660

gacattgaag ctagcattaa tgagatggca gaagccgttc aagcatacgt gccaggatat    720

agactcaaac aaagagtcca atttgaggtc attccacaag acaagccagt taatctccca    780

ggggtcggtc aattctcagg actaaaaact gctgtttggt tagaagtaga aggagctgct    840

cattacctac cagcctacgc cggtaatttg gatataatga catcttccgc tcttgcaaca    900

gcagaaaaga tggcacaaag tctggcccgt aaggcaggag aagcggcata ataa          954
```

<210> SEQ ID NO 23
<211> LENGTH: 512
<212> TYPE: PRT
<213> ORGANISM: Saccharomyces cerevisiae

<400> SEQUENCE: 23

```
Met Ser Val Asn Pro Glu Phe Ile Ala Asp Gly Ile Asp Phe Tyr Pro
  1               5                  10                  15
```

-continued

```
Thr Thr Pro Asp Ala Ala Tyr Phe Asn Ala Ala Asp Gly Lys Asn Lys
            20                  25                  30

Val Asn Arg Ile Asn Gly Asn Ser Glu Asn Leu His His Ser Phe Ala
        35                  40                  45

Ser Gly Cys Arg Arg Ser Ser Leu Ser Val Asp Phe Asn Val Thr Ser
    50                  55                  60

Ser Asp Ser Glu Lys Ser Glu Gln Ser Cys Leu Glu Asn Asn Ser Gln
65                  70                  75                  80

Glu Asp Glu Tyr Phe Cys Asp Ile Phe Ser Thr Glu Leu Lys Leu Asp
                85                  90                  95

Glu Thr Ser Asn Lys Ser Thr Asp Tyr Ser Ser Ser Asn His Gln Tyr
            100                 105                 110

Pro Glu Gln Leu Glu Leu His Asn Tyr Lys Leu Leu Asn Lys Ile Gly
        115                 120                 125

Glu Gly Ala Phe Ser Arg Val Phe Lys Ala Val Gly Ile Asn Thr Asp
    130                 135                 140

Asp Gln Ala Pro Val Ala Ile Lys Ala Ile Ile Lys Lys Gly Ile Ser
145                 150                 155                 160

Ser Asp Ala Ile Leu Lys Gly Asn Asp Arg Ile Gln Gly Ser Ser Arg
                165                 170                 175

Lys Lys Val Leu Asn Glu Val Ala Ile His Lys Leu Val Ser Lys Asn
            180                 185                 190

Asn Pro His Cys Thr Lys Phe Ile Ala Phe Gln Glu Ser Ala Asn Tyr
        195                 200                 205

Tyr Tyr Leu Val Thr Glu Leu Val Thr Gly Gly Glu Ile Phe Asp Arg
    210                 215                 220

Ile Val Gln Leu Thr Cys Phe Ser Glu Asp Leu Ala Arg His Val Ile
225                 230                 235                 240

Thr Gln Val Ala Ile Ala Ile Lys His Met His Tyr Met Gly Ile Val
                245                 250                 255

His Arg Asp Val Lys Pro Glu Asn Leu Leu Phe Glu Pro Ile Pro Phe
            260                 265                 270

Tyr Gly Leu Asp Gly Asp Met Gln Lys Glu Asp Glu Phe Thr Leu Gly
        275                 280                 285

Val Gly Gly Gly Gly Ile Gly Leu Val Lys Leu Met Asp Phe Gly Leu
    290                 295                 300

Ala Lys Lys Leu Arg Asn Asn Thr Ala Lys Thr Pro Cys Gly Thr Ile
305                 310                 315                 320

Glu Tyr Val Ala Ser Glu Val Phe Thr Ser Lys Arg Tyr Ser Met Lys
                325                 330                 335

Val Asp Met Trp Ser Ile Gly Cys Val Leu Phe Thr Leu Leu Cys Gly
            340                 345                 350

Tyr Pro Pro Phe Tyr Glu Lys Asn Glu Lys Thr Leu Leu Lys Lys Ile
        355                 360                 365

Ser Arg Gly Asp Tyr Glu Phe Leu Ala Pro Trp Trp Asp Asn Ile Ser
    370                 375                 380

Ser Gly Ala Lys Asn Ala Val Thr His Leu Leu Glu Val Asp Pro Asn
385                 390                 395                 400

Lys Arg Tyr Asp Ile Asp Asp Phe Leu Asn Asp Pro Trp Leu Asn Ser
                405                 410                 415

Tyr Asp Cys Leu Lys Asp Ser Asn Ser Asn Ser Tyr Ala Ser Val Gln
            420                 425                 430
```

-continued

```
Ser Ile Leu Asn Asp Ser Phe Asp Glu Arg Ala Glu Thr Leu His Cys
        435                 440                 445

Ala Leu Ser Cys Gln Ser Glu Lys Gln Asp Asp Thr Glu Phe Ser Arg
    450                 455                 460

Ser Glu Ser Ser Glu Tyr Ile Phe Met Thr Glu Glu Asp Arg Asn Leu
465                 470                 475                 480

Arg Gly Ser Trp Ile Gly Glu Pro Lys Glu Cys Phe Thr Leu Asp Leu
                485                 490                 495

Ala Thr Ser Ser Ile Tyr Arg Arg Arg Lys Asn Lys Ile Phe Phe Trp
            500                 505                 510


<210> SEQ ID NO 24
<211> LENGTH: 610
<212> TYPE: PRT
<213> ORGANISM: Saccharomyces cerevisiae

<400> SEQUENCE: 24

Met Leu Lys Ile Lys Ala Leu Phe Ser Lys Lys Lys Pro Asp Gln Ala
  1               5                  10                  15

Asp Leu Ser Gln Glu Ser Lys Lys Pro Phe Lys Gly Lys Thr Arg Ser
             20                  25                  30

Ser Gly Thr Asn Asn Lys Asp Val Ser Gln Ile Thr Ser Ser Pro Lys
         35                  40                  45

Lys Ser Phe Gln Asp Lys Asn Ile Val Gln Tyr Pro Ser Val Val Ala
     50                  55                  60

Asp Asp His His Met Lys Ser Leu Thr Asp Glu Leu Val Thr Thr Ile
 65                  70                  75                  80

Asp Ser Asp Ser Ser Pro Ser Asp Asn Ile Thr Thr Glu Asn Val Glu
                 85                  90                  95

Thr Val Thr Ser Val Pro Ala Ile Asp Val His Glu Ser Ser Glu Gly
            100                 105                 110

Gln Leu Ser Ser Asp Pro Leu Ile Ser Asp Glu Ser Leu Ser Glu Gln
        115                 120                 125

Ser Glu Ile Ile Ser Asp Ile Gln Asp Asp Ser Thr Asp Asp Asp Asn
    130                 135                 140

Met Glu Asp Glu Ile Pro Glu Lys Ser Phe Leu Glu Gln Lys Glu Leu
145                 150                 155                 160

Ile Gly Tyr Lys Leu Ile Asn Lys Ile Gly Glu Gly Ala Phe Ser Lys
                165                 170                 175

Val Phe Arg Ala Ile Pro Ala Lys Asn Ser Ser Asn Glu Phe Leu Thr
            180                 185                 190

Lys Asn Tyr Lys Ala Val Ala Ile Lys Val Ile Lys Lys Ala Asp Leu
        195                 200                 205

Ser Ser Ile Asn Gly Asp His Arg Lys Lys Asp Lys Gly Lys Asp Ser
    210                 215                 220

Thr Lys Thr Ser Ser Arg Asp Gln Val Leu Lys Glu Val Ala Leu His
225                 230                 235                 240

Lys Thr Val Ser Ala Gly Cys Ser Gln Ile Val Ala Phe Ile Asp Phe
                245                 250                 255

Gln Glu Thr Asp Ser Tyr Tyr Tyr Ile Ile Gln Glu Leu Leu Thr Gly
            260                 265                 270

Gly Glu Ile Phe Gly Glu Ile Val Arg Leu Thr Tyr Phe Ser Glu Asp
        275                 280                 285

Leu Ser Arg His Val Ile Lys Gln Leu Ala Leu Ala Val Lys His Met
    290                 295                 300
```

-continued

His Ser Leu Gly Val Val His Arg Asp Ile Lys Pro Glu Asn Leu Leu
305 310 315 320

Phe Glu Pro Ile Glu Phe Thr Arg Ser Ile Lys Pro Lys Leu Arg Lys
325 330 335

Ser Asp Asp Pro Gln Thr Lys Ala Asp Glu Gly Ile Phe Thr Pro Gly
340 345 350

Val Gly Gly Gly Gly Ile Gly Ile Val Lys Leu Ala Asp Phe Gly Leu
355 360 365

Ser Lys Gln Ile Phe Ser Lys Asn Thr Lys Thr Pro Cys Gly Thr Val
370 375 380

Gly Tyr Thr Ala Pro Glu Val Val Lys Asp Glu His Tyr Ser Met Lys
385 390 395 400

Val Asp Met Trp Gly Ile Gly Cys Val Leu Tyr Thr Met Leu Cys Gly
405 410 415

Phe Pro Pro Phe Tyr Asp Glu Lys Ile Asp Thr Leu Thr Glu Lys Ile
420 425 430

Ser Arg Gly Glu Tyr Thr Phe Leu Lys Pro Trp Trp Asp Glu Ile Ser
435 440 445

Ala Gly Ala Lys Asn Ala Val Ala Lys Leu Leu Glu Leu Glu Pro Ser
450 455 460

Lys Arg Tyr Asp Ile Asp Gln Phe Leu Asp Asp Pro Trp Leu Asn Thr
465 470 475 480

Phe Asp Cys Leu Pro Lys Glu Gly Glu Ser Ser Gln Lys Lys Ala Gly
485 490 495

Thr Ser Glu Arg Arg His Pro His Lys Lys Gln Phe Gln Leu Phe Gln
500 505 510

Arg Asp Ser Ser Leu Leu Phe Ser Pro Ala Ala Val Ala Met Arg Asp
515 520 525

Ala Phe Asp Ile Gly Asn Ala Val Lys Arg Thr Glu Glu Asp Arg Met
530 535 540

Gly Thr Arg Gly Gly Leu Gly Ser Leu Ala Glu Asp Glu Glu Leu Glu
545 550 555 560

Asp Ser Tyr Ser Gly Ala Gln Gly Asp Glu Gln Leu Glu Gln Asn Met
565 570 575

Phe Gln Leu Thr Leu Asp Thr Ser Thr Ile Leu Gln Arg Arg Lys Lys
580 585 590

Val Gln Glu Asn Asp Val Gly Pro Thr Ile Pro Ile Ser Ala Thr Ile
595 600 605

Arg Glu
610

<210> SEQ ID NO 25
<211> LENGTH: 1539
<212> TYPE: DNA
<213> ORGANISM: Saccharomyces cerevisiae

<400> SEQUENCE: 25
atgtcagtaa acccagaatt tatagccgat ggcatcgatt tttatccaac aacgcccgat 60
gccgcgtatt tcaatgccgc tgatggtaaa aataaagtta acaggataaa tggtaactca 120
gaaaatttac accactcctt tgcatcgggt tgccgtagat catctctttc agtcgacttt 180
aatgttacct cgtccgattc agaaaaaagt gaacagagct gcttggaaaa caactctcaa 240
gaagacgaat atttttgtga cattttttcc actgaattaa aattagatga aacttctaac 300

-continued aagtcaaccg attattccag ttcaaatcac cagtatcctg aacaactgga gttgcacaat 360
tataaactgc tcaataaaat tggtgaaggg gcattttcca gagtatttaa agcagtaggc 420
atcaacacgg atgaccaagc tcctgttgcc atcaaagcaa tcataaagaa aggcatttcg 480
agcgatgcca tcttaaaagg gaatgataga atccaaggtt ccagcagaaa gaaagtctta 540
aacgaagttg ccatccacaa actggtttcg aaaaataatc cgcattgtac aaaatttatc 600
gcattccagg aatcggcgaa ctactattac ttagtgacgg agttagtcac aggtggggaa 660
atatttgata ggatcgtcca actaacatgc tttagtgaag acttagctcg tcatgtcatt 720
actcaggtag caattgcaat taaacatatg cactacatgg gtattgtgca tcgtgatgtc 780
aaaccagaaa acctactatt tgaacctatc ccattttatg gccttgatgg ggacatgcaa 840
aaagaagacg agtttacatt aggtgtcggc ggaggcggta ttggtttagt gaagctaatg 900
gacttcggac tagccaagaa acttcggaac aataccgcaa aaactccctg cggaacgata 960
gaatacgtcg catcagaagt attcacctcc aaacgatatt ccatgaaagt tgatatgtgg 1020
agtattggct gcgtactatt cacgttattg tgtggatatc ctccgtttta cgaaaagaac 1080
gaaaaaacat tattgaagaa aatatcgaga ggagattacg aattcttggc gccatggtgg 1140
gacaacataa gttctggcgc taagaacgca gttacccatc ttttggaggt tgacccaaac 1200
aagagatacg atatcgatga cttcctaaat gatccttggt taaattcgta cgattgtttg 1260
aaggattcaa actcaaattc ttatgccagc gtgcaaagca tactaaatga ttcattcgat 1320
gagagagcag agaccctaca ttgtgcatta agctgccaat ctgaaaaaca agatgacacc 1380
gagttttcca gaagtgaaag ctcggaatac atatttatga cggaagaaga cagaaaccta 1440
cggggcagtt ggatcggtga gccaaaagag tgttttacct tagaccttgc aacatcttct 1500
atataccgaa gaaggaagaa caagatattc ttctggtaa 1539

<210> SEQ ID NO 26
<211> LENGTH: 1833
<212> TYPE: DNA
<213> ORGANISM: Saccharomyces cerevisiae

<400> SEQUENCE: 26
atgcttaaaa taaaggccct tttctcgaaa aagaaaccgg atcaggcaga tttgtctcag 60
gaatctaaaa aaccattcaa gggtaagacc aggtcaagcg gtacaaataa caaagatgtt 120
tcccagatta cttcttcccc taagaaaagc tttcaggaca aaaatatagt tcagtacccg 180
agtgttgtcg cagatgacca tcatatgaag tctttaaccg atgaattagt aaccacgata 240
gactcggact cttcaccgag tgataatatt accacggaaa atgtggaaac agttacttcc 300
gtgccagcta tcgatgtcca tgaaagtagt gaaggtcaat taagttccga ccccttaata 360
tctgacgaat ctctttcgga acaaagcgag attatcagtg atatccagga tgacagtact 420
gatgatgaca atatggaaga tgaaattccg gaaaaatcct tcctcgaaca aaaggaattg 480
ataggttaca agctgatcaa taaaatcggt gaaggtgctt tttcaaaagt ctttagagcc 540
atacctgcta aaaatagttc taatgaattt ttaactaaaa actataaagc tgttgccatt 600
aaagttatca aaaaggcaga tttatcctcg attaatggtg atcatcgtaa gaaggacaaa 660
gggaaggaca gcactaaaac ttcttccaga gatcaagtct tgaaggaagt tgcactacat 720
aagacggttt ccgctggttg ttcacaaatt gtcgcgttca tagacttcca agaaacagat 780
agctattatt atattattca agagttacta accggtgggg aaatcttcgg cgaaattgtt 840
aggttgacct atttcagtga agatttatca aggcatgtaa tcaaacaatt agcactggct 900

```
gttaaacata tgcattcact aggtgtagtg catcgtgata taaaacctga gaatcttctt    960

tttgaaccga ttgaattcac acgctctata aaaccaaaat tgaggaaatc ggatgatccg   1020

caaacaaagg cagacgaggg aattttcaca ccaggagttg gtggtggtgg aattggtata   1080

gtaaaactag ctgattttgg tttgtctaaa caaatatttt ccaagaacac caagactcct   1140

tgtggtacag tcggttacac tgcccctgaa gttgtcaaag atgagcatta ttctatgaaa   1200

gtggatatgt gggggattgg ttgcgttttg tacacaatgt tatgtgggtt cccgccattc   1260

tatgatgaga aaattgacac tttaactgaa aaaatatcaa ggggtgagta tacctttctg   1320

aaaccttggt gggatgaaat cagcgccggt gccaagaatg ccgtggctaa gctattagaa   1380

ctagagccgt ctaaaagata cgacattgac cagtttttgg acgacccatg gttaaataca   1440

ttcgattgtt taccaaagga gggcgaatct tcacaaaaga aagcaggtac ttccgaaaga   1500

cgccatccgc ataagaaaca attccaacta tttcaaagag actcctcgct actgttttca   1560

ccagctgctg ttgctatgcg tgacgccttt gatattggta atgctgtgaa acgtaccgaa   1620

gaagaccgta tgggaacacg tggaggatta ggctcgcttg ctgaggacga agaattggaa   1680

gatagttaca gtggcgccca aggcgatgaa cagctggaac aaaatatgtt ccaattaacg   1740

ctggatacgt ccacgattct gcaaagaaga aaaaaagttc aagaaaatga cgtagggcct   1800

acaattccaa taagcgccac tatcagggaa tag                                1833
```

<210> SEQ ID NO 27
<211> LENGTH: 289
<212> TYPE: DNA
<213> ORGANISM: Artificial Sequence
<220> FEATURE:
<223> OTHER INFORMATION: Synthetic CYC promoter

<400> SEQUENCE: 27

```
atttggcgag cgttggttgg tggatcaagc ccacgcgtag gcaatcctcg agcagatccg     60

ccaggcgtgt atatatagcg tggatggcca ggcaacttta gtgctgacac atacaggcat    120

atatatatgt gtgcgacgac acatgatcat atggcatgca tgtgctctgt atgtatataa    180

aactcttgtt ttcttctttt ctctaaatat tctttcctta tacattagga cctttgcagc    240

ataaattact atacttctat agacacgcaa acacaaatac acacactaa                289
```

<210> SEQ ID NO 28
<211> LENGTH: 401
<212> TYPE: DNA
<213> ORGANISM: Artificial Sequence
<220> FEATURE:
<223> OTHER INFORMATION: Synthetic TEF promoter

<400> SEQUENCE: 28

```
atagcttcaa aatgtttcta ctcctttttt actcttccag attttctcgg actccgcgca     60

tcgccgtacc acttcaaaac acccaagcac agcatactaa atttcccctc tttcttcctc    120

tagggtgtcg ttaattaccc gtactaaagg tttggaaaag aaaaaagaga ccgcctcgtt    180

tctttttctt cgtcgaaaaa ggcaataaaa atttttatca cgtttctttt tcttgaaaat    240

tttttttttg attttttttct ctttcgatga cctcccattg atatttaagt taataaacgg    300

tcttcaattt ctcaagtttc agtttcattt ttcttgttct attacaactt tttttacttc    360

ttgctcatta gaaagaaagc atagcaatct aatctaagtt t                        401
```

<210> SEQ ID NO 29

<211> LENGTH: 655
<212> TYPE: DNA
<213> ORGANISM: Artificial Sequence
<220> FEATURE:
<223> OTHER INFORMATION: Synthetic GPD promoter

<400> SEQUENCE: 29
agtttatcat tatcaatact cgccatttca aagaatacgt aaataattaa tagtagtgat 60
tttcctaact ttatttagtc aaaaaattag ccttttaatt ctgctgtaac ccgtacatgc 120
ccaaaatagg gggcgggtta cacagaatat ataacatcgt aggtgtctgg gtgaacagtt 180
tattcctggc atccactaaa tataatggag cccgcttttt aagctggcat ccagaaaaaa 240
aaagaatccc agcaccaaaa tattgttttc ttcaccaacc atcagttcat aggtccattc 300
tcttagcgca actacagaga acaggggcac aaacaggcaa aaaacgggca caacctcaat 360
ggagtgatgc aacctgcctg gagtaaatga tgacacaagg caattgaccc acgcatgtat 420
ctatctcatt ttcttacacc ttctattacc ttctgctctc tctgatttgg aaaaagctga 480
aaaaaaaggt tgaaaccagt tccctgaaat tattccccta cttgactaat aagtatataa 540
agacggtagg tattgattgt aattctgtaa atctatttct taaacttctt aaattctact 600
tttatagtta gtcttttttt tagttttaaa acaccagaac ttagtttcga cggat 655

<210> SEQ ID NO 30
<211> LENGTH: 1468
<212> TYPE: DNA
<213> ORGANISM: Artificial Sequence
<220> FEATURE:
<223> OTHER INFORMATION: Synthetic ADH promoter

<400> SEQUENCE: 30
gccgggatcg aagaaatgat ggtaaatgaa ataggaaatc aaggagcatg aaggcaaaag 60
acaaatataa gggtcgaacg aaaaataaag tgaaaagtgt tgatatgatg tatttggctt 120
tgcggcgccg aaaaaacgag tttacgcaat tgcacaatca tgctgactct gtggcggacc 180
cgcgctcttg ccggcccggc gataacgctg ggcgtgaggc tgtgcccggc ggagtttttt 240
gcgcctgcat tttccaaggt ttaccctgcg ctaaggggcg agattggaga agcaataaga 300
atgccggttg gggttgcgat gatgacgacc acgacaactg gtgtcattat ttaagttgcc 360
gaaagaacct gagtgcattt gcaacatgag tatactagaa gaatgagcca agacttgcga 420
gacgcgagtt tgccggtggt gcgaacaata gagcgaccat gaccttgaag gtgagacgcg 480
cataaccgct agagtacttt gaagaggaaa cagcaatagg gttgctacca gtataaatag 540
acaggtacat acaacactgg aaatggttgt ctgtttgagt acgctttcaa ttcatttggg 600
tgtgcacttt attatgttac aatatggaag ggaactttac acttctccta tgcacatata 660
ttaattaaag tccaatgcta gtagagaagg ggggtaacac ccctccgcgc tcttttccga 720
tttttttcta aaccgtggaa tatttcggat atccttttgt tgtttccggg tgtacaatat 780
ggacttcctc ttttctggca accaaaccca tacatcggga ttcctataat accttcgttg 840
gtctccctaa catgtaggtg gcggagggga gatatacaat agaacagata ccagacaaga 900
cataatgggc taaacaagac tacaccaatt acactgcctc attgatggtg gtacataacg 960
aactaatact gtagccctag acttgatagc catcatcata tcgaagtttc actacccttt 1020
ttccatttgc catctattga agtaataata ggcgcatgca acttcttttc ttttttttc 1080 ttttctctct cccccgttgt tgtctcacca tatccgcaat gacaaaaaaa tgatggaaga 1140
cactaaagga aaaaattaac gacaaagaca gcaccaacag atgtcgttgt tccagagctg 1200

-continued atgaggggta tctcgaagca cacgaaactt tttccttcct tcattcacgc acactactct 1260
ctaatgagca acggtatacg gccttccttc cagttacttg aatttgaaat aaaaaaaagt 1320
ttgctgtctt gctatcaagt ataaatagac ctgcaattat taatcttttg tttcctcgtc 1380
attgttctcg ttccctttct tccttgtttc tttttctgca caatatttca agctatacca 1440
agcatacaat caactccaag ctggccgc 1468

<210> SEQ ID NO 31
<211> LENGTH: 292
<212> TYPE: DNA
<213> ORGANISM: Artificial Sequence
<220> FEATURE:
<223> OTHER INFORMATION: Synthetic CCW12 promoter

<400> SEQUENCE: 31
ttcgcggcca cctacgccgc tatctttgca acaactatct gcgataactc agcaaatttt 60
gcatattcgt gttgcagtat tgcgataatg ggagtcttac ttccaacata acggcagaaa 120
gaaatgtgag aaaattttgc atcctttgcc tccgttcaag tatataaagt cggcatgctt 180
gataatcttt ctttccatcc tacattgttc taattattct tattctcctt tattctttcc 240
taacatacca agaaattaat cttctgtcat tcgcttaaac actatatcaa ta 292

<210> SEQ ID NO 32
<211> LENGTH: 252
<212> TYPE: DNA
<213> ORGANISM: Artificial Sequence
<220> FEATURE:
<223> OTHER INFORMATION: Synthetic CYC1 terminator

<400> SEQUENCE: 32
tcatgtaatt agttatgtca cgcttacatt cacgccctcc ccccacatcc gctctaaccg 60
aaaaggaagg agttagacaa cctgaagtct aggtccctat ttattttttt atagttatgt 120
tagtattaag aacgttattt atatttcaaa tttttctttt ttttctgtac agacgcgtgt 180
acgcatgtaa cattatactg aaaaccttgc ttgagaaggt tttgggacgc tcgaaggctt 240
taatttgcgg cc 252

<210> SEQ ID NO 33
<211> LENGTH: 31
<212> TYPE: DNA
<213> ORGANISM: Artificial Sequence
<220> FEATURE:
<223> OTHER INFORMATION: primer

<400> SEQUENCE: 33
cgagctcttc gcggccacct acgccgctat c 31

<210> SEQ ID NO 34
<211> LENGTH: 32
<212> TYPE: DNA
<213> ORGANISM: Artificial Sequence
<220> FEATURE:
<223> OTHER INFORMATION: primer

<400> SEQUENCE: 34
gctctagata ttgatatagt gtttaagcga at 32

<210> SEQ ID NO 35
<211> LENGTH: 27
<212> TYPE: DNA

<213> ORGANISM: Artificial Sequence
<220> FEATURE:
<223> OTHER INFORMATION: primer

<400> SEQUENCE: 35
cggccatggc gggagctcgc atgcaag 27

<210> SEQ ID NO 36
<211> LENGTH: 28
<212> TYPE: DNA
<213> ORGANISM: Artificial Sequence
<220> FEATURE:
<223> OTHER INFORMATION: primer

<400> SEQUENCE: 36
cgggatatca ctagtgagct cgctccgc 28

<210> SEQ ID NO 37
<211> LENGTH: 2321
<212> TYPE: DNA
<213> ORGANISM: Artificial Sequence
<220> FEATURE:
<223> OTHER INFORMATION: Synthetic HPH cassette

<400> SEQUENCE: 37
gccgggagag ctcgcatgca agtaacctat tcaaagtaat atctcataca tgtttcatga 60
gggtaacaac atgcgactgg gtgagcatat gttccgctga tgtgatgtgc aagataaaca 120
agcaaggcag aaactaactt cttcttcatg taataaacac accccgcgtt tatttaccta 180
tctctaaact tcaacacctt atatcataac taatatttct tgagataagc acactgcacc 240
cataccttcc ttaaaaacgt agcttccagt ttttggtggt tccggcttcc ttcccgattc 300
cgcccgctaa acgcatattt ttgttgcctg gtggcatttg caaaatgcat aacctatgca 360
tttaaaagat tatgtatgct cttctgactt ttcgtgtgat gaggctcgtg gaaaaaatga 420
ataatttatg aatttgagaa caattttgtg ttgttacggt attttactat ggaataatca 480
atcaattgag gattttatgc aaatatcgtt tgaatatttt tccgaccctt tgagtacttt 540
tcttcataat tgcataatat tgtccgctgc cccttttttct gttagacggt gtcttgatct 600
acttgctatc gttcaacacc accttatttt ctaactattt tttttttagc tcatttgaat 660
cagcttatgg tgatggcaca tttttgcata aacctagctg tcctcgttga acataggaaa 720
aaaaaatata taaacaaggc tctttcactc tccttgcaat cagatttggg tttgttccct 780
ttattttcat atttcttgtc atattccttt ctcaattatt attttctact cataacctca 840
cgcaaaataa cacagtcaaa tcctcgagat gaaaaagcct gaactcaccg cgacgtctgt 900
cgagaagttt ctgatcgaaa agttcgacag cgtctccgac ctgatgcagc tctcggaggg 960
cgaagaatct cgtgctttca gcttcgatgt aggagggcgt ggatatgtcc tgcgggtaaa 1020
tagctgcgcc gatggtttct acaaagatcg ttatgtttat cggcactttg catcggccgc 1080
gctcccgatt ccggaagtgc ttgacattgg ggaattcagc gagagcctga cctattgcat 1140
ctcccgccgt gcacagggtg tcacgttgca agacctgcct gaaaccgaac tgcccgctgt 1200
tctgcagccg gtcgcggagg ccatggatgc gatcgctgcg gccgatctta gccagacgag 1260
cgggttcggc ccattcggac cgcaaggaat cggtcaatac actacatggc gtgatttcat 1320
atgcgcgatt gctgatcccc atgtgtatca ctggcaaact gtgatggacg acaccgtcag 1380
tgcgtccgtc gcgcaggctc tcgatgagct gatgctttgg gccgaggact gccccgaagt 1440
ccggcacctc gtgcacgcgg atttcggctc caacaatgtc ctgacggaca atggccgcat 1500
aacagcggtc attgactgga gcgaggcgat gttcggggat tcccaatacg aggtcgccaa 1560
catcttcttc tggaggccgt ggttggcttg tatggagcag cagacgcgct acttcgagcg 1620
gaggcatccg gagcttgcag gatcgccgcg gctccgggcg tatatgctcc gcattggtct 1680
tgaccaactc tatcagagct tggttgacgg caatttcgat gatgcagctt gggcgcaggg 1740
tcgatgcgac gcaatcgtcc gatccggagc cgggactgtc gggcgtacac aaatcgcccg 1800
cagaagcgcg gccgtctgga ccgatggctg tgtagaagta ctcgccgata gtggaaaccg 1860
acgccccagc actcgtccgg atcgggagat gggggaggct aactgaggat ccgtagatac 1920
attgatgcta tcaatcaaga gaactggaaa gattgtgtaa ccttgaaaaa cggtgaaact 1980
tacgggtcca agattgtcta cagattttcc tgatttgcca gcttactatc cttcttgaaa 2040
atatgcactc tatatctttt agttcttaat tgcaacacat agatttgctg tataacgaat 2100
tttatgctat tttttaaatt tggagttcag tgataaaagt gtcacagcga atttcctcac 2160
atgtagggac cgaattgttt acaagttctc tgtaccacca tggagacatc aaaaattgaa 2220
aatctatgga aagatatgga cggtagcaac aagaatatag cacgagccgc ggagcgagct 2280
cggccgcact agtgatatcc cgcggccatg gcggccggga g 2321

<210> SEQ ID NO 38
<211> LENGTH: 18
<212> TYPE: DNA
<213> ORGANISM: Artificial Sequence
<220> FEATURE:
<223> OTHER INFORMATION: primer

<400> SEQUENCE: 38
gaaacagcta tgaccatg 18

<210> SEQ ID NO 39
<211> LENGTH: 32
<212> TYPE: DNA
<213> ORGANISM: Artificial Sequence
<220> FEATURE:
<223> OTHER INFORMATION: primer

<400> SEQUENCE: 39
gacatgacga gctcgaattg ggtaccggcc gc 32

<210> SEQ ID NO 40
<211> LENGTH: 4173
<212> TYPE: DNA
<213> ORGANISM: Artificial Sequence
<220> FEATURE:
<223> OTHER INFORMATION: Synthetic pUC57-Ura3HA vector

<400> SEQUENCE: 40
gatgacggtg aaaacctctg acacatgcag ctcccggaga cggtcacagc ttgtctgtaa 60
gcggatgccg ggagcagaca agcccgtcag ggcgcgtcag cgggtgttgg cgggtgtcgg 120
ggctggctta actatgcggc atcagagcag attgtactga gagtgcacca tatgcggtgt 180
gaaataccgc acagatgcgt aaggagaaaa taccgcatca ggcgccattc gccattcagg 240
ctgcgcaact gttgggaagg gcgatcggtg cgggcctctt cgctattacg ccagctggcg 300
aaagggggat gtgctgcaag gcgattaagt tgggtaacgc cagggttttc ccagtcacga 360
cgttgtaaaa cgacggccag tgaattcgag ctcggtacct cgcgaatgca tctagatatc 420
ggatcccgac gagctgcacc gcggtggcgg ccgtatcttt tacccatacg atgttcctga 480

-continued

```
ctatgcgggc tatccctatg acgtcccgga ctatgcagga tcctatccat atgacgttcc    540
agattacgct gctcagtgcg gccgcctgag agtgcaccat accacagctt ttcaattcaa    600
ttcatcattt ttttttttatt cttttttttg atttcggttt ctttgaaatt tttttgattc    660
ggtaatctcc gaacagaagg aagaacgaag gaaggagcac agacttagat tggtatatat    720
acgcatatgt agtgttgaag aaacatgaaa ttgcccagta ttcttaaccc aactgcacag    780
aacaaaaacc tgcaggaaac gaagataaat catgtcgaaa gctacatata aggaacgtgc    840
tgctactcat cctagtcctg ttgctgccaa gctatttaat atcatgcacg aaaagcaaac    900
aaacttgtgt gcttcattgg atgttcgtac caccaaggaa ttactggagt tagttgaagc    960
attaggtccc aaaatttgtt tactaaaaac acatgtggat atcttgactg atttttccat   1020
ggagggcaca gttaagccgc taaaggcatt atccgccaag tacaattttt tactcttcga   1080
agacagaaaa tttgctgaca ttggtaatac agtcaaattg cagtactctg cgggtgtata   1140
cagaatagca gaatgggcag acattacgaa tgcacacggt gtggtgggcc caggtattgt   1200
tagcggtttg aagcaggcgg cagaagaagt aacaaaggaa cctagaggcc ttttgatgtt   1260
agcagaattg tcatgcaagg gctccctatc tactggagaa tatactaagg gtactgttga   1320
cattgcgaag agcgacaaag attttgttat cggctttatt gctcaaagag acatgggtgg   1380
aagagatgaa ggttacgatt ggttgattat gacacccggt gtgggtttag atgacaaggg   1440
agacgcattg ggtcaacagt atagaaccgt ggatgatgtg gtctctacag gatctgacat   1500
tattattgtt ggaagaggac tatttgcaaa gggaagggat gctaaggtag agggtgaacg   1560
ttacagaaaa gcaggctggg aagcatattt gagaagatgc ggccagcaaa actaaaaaac   1620
tgtattataa gtaaatgcat gtatactaaa ctcacaaatt agagcttcaa tttaattata   1680
tcagttatta ccctatgcgg tgtgaaatac cgcacagatg cgtaaggaga aaataccgca   1740
tcaggaaatt gtagcggccg cgaatttgag cttatctttt acccatacga tgttcctgac   1800
tatgcgggct atccctatga cgtcccggac tatgcaggat cctatccata tgacgttcca   1860
gattacgcta ctagcggggg gcccggtgac gggcccgtcg actgcagagg cctgcatgca   1920
agcttggcgt aatcatggtc atagctgttt cctgtgtgaa attgttatcc gctcacaatt   1980
ccacacaaca tacgagccgg aagcataaag tgtaaagcct ggggtgccta atgagtgagc   2040
taactcacat taattgcgtt gcgctcactg cccgctttcc agtcgggaaa cctgtcgtgc   2100
cagctgcatt aatgaatcgg ccaacgcgcg gggagaggcg gtttgcgtat tgggcgctct   2160
tccgcttcct cgctcactga ctcgctgcgc tcggtcgttc ggctgcggcg agcggtatca   2220
gctcactcaa aggcggtaat acggttatcc acagaatcag gggataacgc aggaaagaac   2280
atgtgagcaa aaggccagca aaaggccagg aaccgtaaaa aggccgcgtt gctggcgttt   2340
ttccataggc tccgcccccc tgacgagcat cacaaaaatc gacgctcaag tcagaggtgg   2400
cgaaacccga caggactata aagataccag gcgtttcccc ctggaagctc cctcgtgcgc   2460
tctcctgttc cgaccctgcc gcttaccgga tacctgtccg cctttctccc ttcgggaagc   2520
gtggcgcttt ctcatagctc acgctgtagg tatctcagtt cggtgtaggt cgttcgctcc   2580
aagctgggct gtgtgcacga accccccgtt cagcccgacc gctgcgcctt atccggtaac   2640
tatcgtcttg agtccaaccc ggtaagacac gacttatcgc cactggcagc agccactggt   2700
aacaggatta gcagagcgag gtatgtaggc ggtgctacag agttcttgaa gtggtggcct   2760
aactacggct acactagaag aacagtattt ggtatctgcg ctctgctgaa gccagttacc   2820
ttcggaaaaa gagttggtag ctcttgatcc ggcaaacaaa ccaccgctgg tagcggtggt   2880
```

```
tttttgttt gcaagcagca gattacgcgc agaaaaaaag gatctcaaga agatcctttg   2940

atcttttcta cggggtctga cgctcagtgg aacgaaaact cacgttaagg gattttggtc   3000

atgagattat caaaaaggat cttcacctag atccttttaa attaaaaatg aagttttaaa   3060

tcaatctaaa gtatatatga gtaaacttgg tctgacagtt accaatgctt aatcagtgag   3120

gcacctatct cagcgatctg tctatttcgt tcatccatag ttgcctgact ccccgtcgtg   3180

tagataacta cgatacggga gggcttacca tctggcccca gtgctgcaat gataccgcga   3240

gacccacgct caccggctcc agatttatca gcaataaacc agccagccgg aagggccgag   3300

cgcagaagtg gtcctgcaac tttatccgcc tccatccagt ctattaattg ttgccgggaa   3360

gctagagtaa gtagttcgcc agttaatagt ttgcgcaacg ttgttgccat tgctacaggc   3420

atcgtggtgt cacgctcgtc gtttggtatg gcttcattca gctccggttc ccaacgatca   3480

aggcgagtta catgatcccc catgttgtgc aaaaaagcgg ttagctcctt cggtcctccg   3540

atcgttgtca gaagtaagtt ggccgcagtg ttatcactca tggttatggc agcactgcat   3600

aattctctta ctgtcatgcc atccgtaaga tgcttttctg tgactggtga gtactcaacc   3660

aagtcattct gagaatagtg tatgcggcga ccgagttgct cttgcccggc gtcaatacgg   3720

gataataccg cgccacatag cagaacttta aaagtgctca tcattggaaa acgttcttcg   3780

gggcgaaaac tctcaaggat cttaccgctg ttgagatcca gttcgatgta acccactcgt   3840

gcacccaact gatcttcagc atcttttact ttcaccagcg tttctgggtg agcaaaaaca   3900

ggaaggcaaa atgccgcaaa aaagggaata agggcgacac ggaaatgttg aatactcata   3960

ctcttccttt ttcaatatta ttgaagcatt tatcagggtt attgtctcat gagcggatac   4020

atatttgaat gtatttagaa aaataaacaa ataggggttc cgcgcacatt tccccgaaaa   4080

gtgccacctg acgtctaaga aaccattatt atcatgacat taacctataa aaataggcgt   4140

atcacgaggc cctttcgtct cgcgcgtttc ggt                                 4173
```

<210> SEQ ID NO 41
<211> LENGTH: 62
<212> TYPE: DNA
<213> ORGANISM: Artificial Sequence
<220> FEATURE:
<223> OTHER INFORMATION: primer

<400> SEQUENCE: 41

```
gcttataaaa ctttaactaa taattagaga ttaaatcgct taaggtttcc cgactggaaa     60

gc                                                                    62
```

<210> SEQ ID NO 42
<211> LENGTH: 64
<212> TYPE: DNA
<213> ORGANISM: Artificial Sequence
<220> FEATURE:
<223> OTHER INFORMATION: primer

<400> SEQUENCE: 42

```
ctactcataa cctcacgcaa aataacacag tcaaatcaat caaaccagtc acgacgttgt     60

aaaa                                                                  64
```

<210> SEQ ID NO 43
<211> LENGTH: 20
<212> TYPE: DNA
<213> ORGANISM: Artificial Sequence
<220> FEATURE:

-continued

<223> OTHER INFORMATION: primer

<400> SEQUENCE: 43
ggacgtaaag ggtagcctcc 20

<210> SEQ ID NO 44
<211> LENGTH: 22
<212> TYPE: DNA
<213> ORGANISM: Artificial Sequence
<220> FEATURE:
<223> OTHER INFORMATION: primer

<400> SEQUENCE: 44
gaagcggacc cagacttaag cc 22

<210> SEQ ID NO 45
<211> LENGTH: 65
<212> TYPE: DNA
<213> ORGANISM: Artificial Sequence
<220> FEATURE:
<223> OTHER INFORMATION: primer

<400> SEQUENCE: 45
ccgaaatgat tccctttcct gcacaacacg agatctttca cgcatccagt cacgacgttg 60
taaaa 65

<210> SEQ ID NO 46
<211> LENGTH: 64
<212> TYPE: DNA
<213> ORGANISM: Artificial Sequence
<220> FEATURE:
<223> OTHER INFORMATION: primer

<400> SEQUENCE: 46
aaagtagcct taaagctagg ctataatcat gcatcctcaa attctaggtt tcccgacgga 60
aagc 64

<210> SEQ ID NO 47
<211> LENGTH: 25
<212> TYPE: DNA
<213> ORGANISM: Artificial Sequence
<220> FEATURE:
<223> OTHER INFORMATION: primer

<400> SEQUENCE: 47
cgcaagaacg tagtatccac atgcc 25

<210> SEQ ID NO 48
<211> LENGTH: 21
<212> TYPE: DNA
<213> ORGANISM: Artificial Sequence
<220> FEATURE:
<223> OTHER INFORMATION: primer

<400> SEQUENCE: 48
ggatatttac agaacgatgc g 21

<210> SEQ ID NO 49
<211> LENGTH: 70
<212> TYPE: DNA
<213> ORGANISM: Artificial Sequence
<220> FEATURE:
<223> OTHER INFORMATION: primer

<400> SEQUENCE: 49
ccctatgtct ctggccgatc acgcgccatt gtccctcaga aacaaatcaa ccagtcacga 60
cgttgtaaaa 70

<210> SEQ ID NO 50
<211> LENGTH: 70
<212> TYPE: DNA
<213> ORGANISM: Artificial Sequence
<220> FEATURE:
<223> OTHER INFORMATION: primer

<400> SEQUENCE: 50
tagaagcaac tgtgccgaca gcctctgaat gagtggtgtt gtaaccaccc aggtttcccg 60
actggaaagc 70

<210> SEQ ID NO 51
<211> LENGTH: 25
<212> TYPE: DNA
<213> ORGANISM: Artificial Sequence
<220> FEATURE:
<223> OTHER INFORMATION: primer

<400> SEQUENCE: 51
tcaatgagac tgttgtcctc ctact 25

<210> SEQ ID NO 52
<211> LENGTH: 24
<212> TYPE: DNA
<213> ORGANISM: Artificial Sequence
<220> FEATURE:
<223> OTHER INFORMATION: primer

<400> SEQUENCE: 52
tacatccttg tcgagccttg ggca 24

<210> SEQ ID NO 53
<211> LENGTH: 75
<212> TYPE: DNA
<213> ORGANISM: Artificial Sequence
<220> FEATURE:
<223> OTHER INFORMATION: primer

<400> SEQUENCE: 53
acaatatttc aagctatacc aagcatacaa tcaactatct catatacaat gggccgcaaa 60
ttaaagcctt cgagc 75

<210> SEQ ID NO 54
<211> LENGTH: 75
<212> TYPE: DNA
<213> ORGANISM: Artificial Sequence
<220> FEATURE:
<223> OTHER INFORMATION: primer

<400> SEQUENCE: 54
aatcataaga aattcgctta tttagaagtg tcaacaacgt atctaccaac gactaaaggg 60
aacaaaagct ggagc 75

<210> SEQ ID NO 55
<211> LENGTH: 18
<212> TYPE: DNA
<213> ORGANISM: Artificial Sequence
<220> FEATURE:
<223> OTHER INFORMATION: primer -continued

<400> SEQUENCE: 55
tgctgtcttg ctatcaag 18

<210> SEQ ID NO 56
<211> LENGTH: 19
<212> TYPE: DNA
<213> ORGANISM: Artificial Sequence
<220> FEATURE:
<223> OTHER INFORMATION: primer

<400> SEQUENCE: 56
caggaaagag ttactcaag 19

<210> SEQ ID NO 57
<211> LENGTH: 5779
<212> TYPE: DNA
<213> ORGANISM: Artificial Sequence
<220> FEATURE:
<223> OTHER INFORMATION: Synthetic pUC19-His-MhpF

<400> SEQUENCE: 57
tcgacctgca ggcatgcaag cttggcgtaa tcatggtcat agctgtttcc tgtgtgaaat 60
tgttatccgc tcacaattcc acacaacata cgagccggaa gcataaagtg taaagcctgg 120
ggtgcctaat gagtgagcta actcacatta attgcgttgc gctcactgcc cgctttccag 180
tcgggaaacc tgtcgtgcca gctgcattaa tgaatcggcc aacgcgcggg gagaggcggt 240
ttgcgtattg ggcgctcttc cgcttcctcg ctcactgact cgctgcgctc ggtcgttcgg 300
ctgcggcgag cggtatcagc tcactcaaag gcggtaatac ggttatccac agaatcaggg 360
gataacgcag gaaagaacat gtgagcaaaa ggccagcaaa aggccaggaa ccgtaaaaag 420
gccgcgttgc tggcgttttt ccataggctc cgcccccctg acgagcatca caaaaatcga 480
cgctcaagtc agaggtggcg aaacccgaca ggactataaa gataccaggc gtttccccct 540
ggaagctccc tcgtgcgctc tcctgttccg accctgccgc ttaccggata cctgtccgcc 600
tttctccctt cgggaagcgt ggcgctttct catagctcac gctgtaggta tctcagttcg 660
gtgtaggtcg ttcgctccaa gctgggctgt gtgcacgaac cccccgttca gcccgaccgc 720
tgcgccttat ccggtaacta tcgtcttgag tccaacccgg taagacacga cttatcgcca 780
ctggcagcag ccactggtaa caggattagc agagcgaggt atgtaggcgg tgctacagag 840
ttcttgaagt ggtggcctaa ctacggctac actagaagaa cagtatttgg tatctgcgct 900
ctgctgaagc cagttacctt cggaaaaaga gttggtagct cttgatccgg caaacaaacc 960
accgctggta gcggtggttt ttttgtttgc aagcagcaga ttacgcgcag aaaaaaagga 1020
tctcaagaag atcctttgat cttttctacg gggtctgacg ctcagtggaa cgaaaactca 1080
cgttaaggga ttttggtcat gagattatca aaaaggatct tcacctagat ccttttaaat 1140
taaaaatgaa gttttaaatc aatctaaagt atatatgagt aaacttggtc tgacagttac 1200
caatgcttaa tcagtgaggc acctatctca gcgatctgtc tatttcgttc atccatagtt 1260
gcctgactcc ccgtcgtgta gataactacg atacgggagg gcttaccatc tggccccagt 1320
gctgcaatga taccgcgaga cccacgctca ccggctccag atttatcagc aataaaccag 1380
ccagccggaa gggccgagcg cagaagtggt cctgcaactt tatccgcctc catccagtct 1440
attaattgtt gccgggaagc tagagtaagt agttcgccag ttaatagttt gcgcaacgtt 1500
gttgccattg ctacaggcat cgtggtgtca cgctcgtcgt ttggtatggc ttcattcagc 1560
tccggttccc aacgatcaag gcgagttaca tgatccccca tgttgtgcaa aaaagcggtt 1620

-continued

```
agctccttcg gtcctccgat cgttgtcaga agtaagttgg ccgcagtgtt atcactcatg   1680
gttatggcag cactgcataa ttctcttact gtcatgccat ccgtaagatg cttttctgtg   1740
actggtgagt actcaaccaa gtcattctga gaatagtgta tgcggcgacc gagttgctct   1800
tgcccggcgt caatacggga taataccgcg ccacatagca gaactttaaa agtgctcatc   1860
attggaaaac gttcttcggg gcgaaaactc tcaaggatct taccgctgtt gagatccagt   1920
tcgatgtaac ccactcgtgc acccaactga tcttcagcat cttttacttt caccagcgtt   1980
tctgggtgag caaaaacagg aaggcaaaat gccgcaaaaa agggaataag ggcgacacgg   2040
aaatgttgaa tactcatact cttccttttt caatattatt gaagcattta tcagggttat   2100
tgtctcatga gcggatacat atttgaatgt atttagaaaa ataaacaaat aggggttccg   2160
cgcacatttc cccgaaaagt gccacctgac gtctaagaaa ccattattat catgacatta   2220
acctataaaa ataggcgtat cacgaggccc tttcgtctcg cgcgtttcgg tgatgacggt   2280
gaaaacctct gacacatgca gctcccggag acggtcacag cttgtctgta agcggatgcc   2340
gggagcagac aagcccgtca gggcgcgtca gcgggtgttg gcgggtgtcg gggctggctt   2400
aactatgcgg catcagagca gattgtactg agagtgcacc atatgcggtg tgaaataccg   2460
cacagatgcg taaggagaaa ataccgcatc aggcgccatt cgccattcag gctgcgcaac   2520
tgttgggaag ggcgatcggt gcgggcctct tcgctattac gccagctggc gaaaggggga   2580
tgtgctgcaa ggcgattaag ttgggtaacg ccagggtttt cccagtcacg acgttgtaaa   2640
acgacggcca gtgaattcga gctcagttta tcattatcaa tactcgccat ttcaaagaat   2700
acgtaaataa ttaatagtag tgattttcct aactttattt agtcaaaaaa ttagcctttt   2760
aattctgctg taacccgtac atgcccaaaa tagggggcgg gttacacaga atatataaca   2820
tcgtaggtgt ctgggtgaac agtttattcc tggcatccac taaatataat ggagcccgct   2880
ttttaagctg gcatccagaa aaaaaaagaa tcccagcacc aaaatattgt tttcttcacc   2940
aaccatcagt tcataggtcc attctcttag cgcaactaca gagaacaggg gcacaaacag   3000
gcaaaaaacg ggcacaacct caatggagtg atgcaacctg cctggagtaa atgatgacac   3060
aaggcaattg acccacgcat gtatctatct cattttctta caccttctat taccttctgc   3120
tctctctgat ttggaaaaag ctgaaaaaaa aggttgaaac cagttccctg aaattattcc   3180
cctacttgac taataagtat ataaagacgg taggtattga ttgtaattct gtaaatctat   3240
ttcttaaact tcttaaattc tacttttata gttagtcttt tttttagttt taaaacacca   3300
gaacttagtt tcgacggatt ctagaactag tggatccatg tcaaagcgaa aagtagctat   3360
cataggttca ggtaatattg gtactgattt gatgatcaaa atcctgagac atggccagca   3420
cttggagatg gccgtcatgg ttggtatcga cccacaatcc gatggcttag ctagagctag   3480
gagaatgggt gttgccacaa ctcacgaagg ggttattggc ttaatgaaca tgccagaatt   3540
tgcagacatc gatatagttt ttgatgctac tagtgcaggg gcacatgtga aaaacgacgc   3600
ggctttaaga gaagccaagc cagatattag attaattgat cttacccctg ctgctatagg   3660
tccttactgc gttcctgtag ttaaccttga agctaatgtg gaccagttga acgtgaatat   3720
ggttacatgt ggtggccaag ctaccatacc aatggttgct gctgtctcta gagtggccag   3780
agtacattat gccgagatca ttgcgtctat cgcatctaag tctgccggtc ctggaacaag   3840
ggctaacatc gatgagttca ctgagacaac ctctagagct atcgaagtag taggaggcgc   3900
agcaaaaggt aaagcgatca ttgttttgaa tcctgccgaa ccacctttga tgatgagaga   3960
```

tacggtctac gtgctatcag atgaagcttc ccaggatgac attgaagcta gcattaatga 4020
gatggcagaa gccgttcaag catacgtgcc aggatataga ctcaaacaaa gagtccaatt 4080
tgaggtcatt ccacaagaca agccagttaa tctcccaggg gtcggtcaat tctcaggact 4140
aaaaactgct gtttggttag aagtagaagg agctgctcat tacctaccag cctacgccgg 4200
taatttggat ataatgacat cttccgctct tgcaacagca gaaaagatgg cacaaagtct 4260
ggcccgtaag gcaggagaag cggcataata aatcctcgag tcatgtaatt agttatgtca 4320
cgcttacatt cacgccctcc ccccacatcc gctctaaccg aaaaggaagg agttagacaa 4380
cctgaagtct aggtccctat ttattttttt atagttatgt tagtattaag aacgttattt 4440
atatttcaaa tttttctttt ttttctgtac agacgcgtgt acgcatgtaa cattatactg 4500
aaaaccttgc ttgagaaggt tttgggacgc tcgaaggctt taatttgcgg ccggtaccca 4560
attcgagctc ggtacccggg gatcctctag agtcgacaat tcccgtttta agagcttggt 4620
gagcgctagg agtcactgcc aggtatcgtt tgaacacggc attagtcagg gaagtcataa 4680
cacagtcctt tcccgcaatt ttcttttttct attactcttg gcctcctcta gtacactcta 4740 tatttttttta tgcctcggta atgattttca tttttttttt tcccctagcg gatgactctt 4800 ttttttttctt agcgattggc attatcacat aatgaattat acattatata aagtaatgtg 4860
atttcttcga agaatatact aaaaaatgag caggcaagat aaacgaaggc aaagatgaca 4920
gagcagaaag ccctagtaaa gcgtattaca aatgaaacca agattcagat tgcgatctct 4980
ttaaagggtg gtcccctagc gatagagcac tcgatcttcc cagaaaaaga ggcagaagca 5040
gtagcagaac aggccacaca atcgcaagtg attaacgtcc acacaggtat agggtttctg 5100
gaccatatga tacatgctct ggccaagcat tccggctggt cgctaatcgt tgagtgcatt 5160
ggtgacttac acatagacga ccatcacacc actgaagact gcgggattgc tctcggtcaa 5220
gcttttaaag aggccctact ggcgcgtgga gtaaaaaggt ttggatcagg atttgcgcct 5280
ttggatgagg cactttccag agcggtggta gatctttcga acaggccgta cgcagttgtc 5340
gaacttggtt tgcaaaggga gaaagtagga gatctctctt gcgagatgat cccgcatttt 5400
cttgaaagct ttgcagaggc tagcagaatt accctccacg ttgattgtct gcgaggcaag 5460
aatgatcatc accgtagtga gagtgcgttc aaggctcttg cggttgccat aagagaagcc 5520
acctcgccca atggtaccaa cgatgttccc tccaccaaag gtgttcttat gtagtgacac 5580
cgattattta aagctgcagc atacgatata tatacatgtg tatatatgta tacctatgaa 5640
tgtcagtaag tatgtatacg aacagtatga tactgaagat gacaaggtaa tgcatcattc 5700
tatacgtgtc attctgaacg aggcgcgctt tcctttttttc tttttgcttt ttctttttttt 5760 ttctcttgaa ctcgacggg 5779

<210> SEQ ID NO 58
<211> LENGTH: 64
<212> TYPE: DNA
<213> ORGANISM: Artificial Sequence
<220> FEATURE:
<223> OTHER INFORMATION: primer

<400> SEQUENCE: 58
caagaaacat ctttaacata cacaaacaca tactatcaga atacccagtc acgacgttgt 60
aaaa 64

<210> SEQ ID NO 59
<211> LENGTH: 65

<212> TYPE: DNA
<213> ORGANISM: Artificial Sequence
<220> FEATURE:
<223> OTHER INFORMATION: primer

<400> SEQUENCE: 59
gtattttgtg tatatgacgg aaagaaatgc aggttggtac attacaggtt tcccgactgg 60
aaagc 65

<210> SEQ ID NO 60
<211> LENGTH: 31
<212> TYPE: DNA
<213> ORGANISM: Artificial Sequence
<220> FEATURE:
<223> OTHER INFORMATION: primer

<400> SEQUENCE: 60
cctcctgagt cgacaattcc cgttttaaga g 31

<210> SEQ ID NO 61
<211> LENGTH: 30
<212> TYPE: DNA
<213> ORGANISM: Artificial Sequence
<220> FEATURE:
<223> OTHER INFORMATION: primer

<400> SEQUENCE: 61
cgaccgtggt cgacccgtcg agttcaagag 30

<210> SEQ ID NO 62
<211> LENGTH: 26
<212> TYPE: DNA
<213> ORGANISM: Artificial Sequence
<220> FEATURE:
<223> OTHER INFORMATION: primer

<400> SEQUENCE: 62
gacagtctag caaacagtag tagtcc 26

<210> SEQ ID NO 63
<211> LENGTH: 19
<212> TYPE: DNA
<213> ORGANISM: Artificial Sequence
<220> FEATURE:
<223> OTHER INFORMATION: primer

<400> SEQUENCE: 63
tgacgtaaga ccaagtaag 19

<210> SEQ ID NO 64
<211> LENGTH: 627
<212> TYPE: DNA
<213> ORGANISM: Artificial Sequence
<220> FEATURE:
<223> OTHER INFORMATION: Synthetic TPI1 promoter

<400> SEQUENCE: 64
gctacccaaa tggactgatt gtgagggaga cctaactaca tagtgtttaa agattacgga 60
tatttaactt acttagaata atgccatttt tttgagttat aataatccta cgttagtgtg 120
agcgggattt aaactgtgag gaccttaata cattcagaca cttctgcggt atcaccctac 180
ttattccctt cgagattata tctaggaacc catcaggttg gtggaagatt acccgttcta 240
agacttttca gcttcctcta ttgatgttac acctggacac cccttttctg gcatccagtt 300

```
tttaatcttc agtggcatgt gagattctcc gaaattaatt aaagcaatca cacaattctc    360

tcggatacca cctcggttga aactgacagg tggtttgtta cgcatgctaa tgcaaaggag    420

cctatatacc tttggctcgg ctgctgtaac agggaatata aagggcagca taatttagga    480

gtttagtgaa cttgcaacat ttactatttt cccttcttac gtaaatattt ttctttttaa    540

ttctaaatca atctttttca attttttgtt tgtattcttt tcttgcttaa atctataact    600

acaaaaaaca catacataaa ctaaaaa                                        627


<210> SEQ ID NO 65
<211> LENGTH: 18
<212> TYPE: DNA
<213> ORGANISM: Artificial Sequence
<220> FEATURE:
<223> OTHER INFORMATION: primer

<400> SEQUENCE: 65

gtttaaagat tacggata                                                   18


<210> SEQ ID NO 66
<211> LENGTH: 27
<212> TYPE: DNA
<213> ORGANISM: Artificial Sequence
<220> FEATURE:
<223> OTHER INFORMATION: primer

<400> SEQUENCE: 66

tttttagttt atgtatgtgt tttttgt                                          27


<210> SEQ ID NO 67
<211> LENGTH: 2710
<212> TYPE: DNA
<213> ORGANISM: Artificial Sequence
<220> FEATURE:
<223> OTHER INFORMATION: Synthetic P57 vector

<400> SEQUENCE: 67

tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt ggagatcggt acttcgcgaa    420

tgcgtcgaga tatcggatgc cgggaccgac gagtgcagag gcgtgcaagc gagcttggcg    480

taatcatggt catagctgtt tcctgtgtga aattgttatc cgctcacaat tccacacaac    540

atacgagccg gaagcataaa gtgtaaagcc tggggtgcct aatgagtgag ctaactcaca    600

ttaattgcgt tgcgctcact gcccgctttc cagtcgggaa acctgtcgtg ccagctgcat    660

taatgaatcg gccaacgcgc ggggagaggc ggtttgcgta ttgggcgctc ttccgcttcc    720

tcgctcactg actcgctgcg ctcggtcgtt cggctgcggc gagcggtatc agctcactca    780

aaggcggtaa tacggttatc cacagaatca ggggataacg caggaaagaa catgtgagca    840

aaaggccagc aaaaggccag gaaccgtaaa aaggccgcgt tgctggcgtt tttccatagg    900

ctccgccccc ctgacgagca tcacaaaaat cgacgctcaa gtcagaggtg gcgaaacccg    960

acaggactat aaagatacca ggcgtttccc cctggaagct ccctcgtgcg ctctcctgtt   1020
```

ccgaccctgc cgcttaccgg atacctgtcc gcctttctcc cttcgggaag cgtggcgctt 1080
tctcatagct cacgctgtag gtatctcagt tcggtgtagg tcgttcgctc caagctgggc 1140
tgtgtgcacg aaccccccgt tcagcccgac cgctgcgcct tatccggtaa ctatcgtctt 1200
gagtccaacc cggtaagaca cgacttatcg ccactggcag cagccactgg taacaggatt 1260
agcagagcga ggtatgtagg cggtgctaca gagttcttga agtggtggcc taactacggc 1320
tacactagaa gaacagtatt tggtatctgc gctctgctga agccagttac cttcggaaaa 1380
agagttggta gctcttgatc cggcaaacaa accaccgctg gtagcggtgg tttttttgtt 1440
tgcaagcagc agattacgcg cagaaaaaaa ggatctcaag aagatccttt gatcttttct 1500
acggggtctg acgctcagtg gaacgaaaac tcacgttaag ggattttggt catgagatta 1560
tcaaaaagga tcttcaccta gatcctttta aattaaaaat gaagttttaa atcaatctaa 1620
agtatatatg agtaaacttg gtctgacagt taccaatgct taatcagtga ggcacctatc 1680
tcagcgatct gtctatttcg ttcatccata gttgcctgac tccccgtcgt gtagataact 1740
acgatacggg agggcttacc atctggcccc agtgctgcaa tgataccgcg agacccacgc 1800
tcaccggctc cagatttatc agcaataaac cagccagccg gaagggccga gcgcagaagt 1860
ggtcctgcaa ctttatccgc ctccatccag tctattaatt gttgccggga agctagagta 1920
agtagttcgc cagttaatag tttgcgcaac gttgttgcca ttgctacagg catcgtggtg 1980
tcacgctcgt cgtttggtat ggcttcattc agctccggtt cccaacgatc aaggcgagtt 2040
acatgatccc ccatgttgtg caaaaaagcg gttagctcct tcggtcctcc gatcgttgtc 2100
agaagtaagt tggccgcagt gttatcactc atggttatgg cagcactgca taattctctt 2160
actgtcatgc catccgtaag atgcttttct gtgactggtg agtactcaac caagtcattc 2220
tgagaatagt gtatgcggcg accgagttgc tcttgcccgg cgtcaatacg ggataatacc 2280
gcgccacata gcagaacttt aaaagtgctc atcattggaa aacgttcttc ggggcgaaaa 2340
ctctcaagga tcttaccgct gttgagatcc agttcgatgt aacccactcg tgcacccaac 2400
tgatcttcag catcttttac tttcaccagc gtttctgggt gagcaaaaac aggaaggcaa 2460
aatgccgcaa aaaagggaat aagggcgaca cggaaatgtt gaatactcat actcttcctt 2520
tttcaatatt attgaagcat ttatcagggt tattgtctca tgagcggata catatttgaa 2580
tgtatttaga aaaataaaca aataggggtt ccgcgcacat ttccccgaaa agtgccacct 2640
gacgtctaag aaaccattat tatcatgaca ttaacctata aaaataggcg tatcacgagg 2700
ccctttcgtc 2710

<210> SEQ ID NO 68
<211> LENGTH: 4777
<212> TYPE: DNA
<213> ORGANISM: Artificial Sequence
<220> FEATURE:
<223> OTHER INFORMATION: Synthetic P57-Ptpi1 vector

<400> SEQUENCE: 68
gatgacggtg aaaacctctg acacatgcag ctcccggaga cggtcacagc ttgtctgtaa 60
gcggatgccg ggagcagaca agcccgtcag ggcgcgtcag cgggtgttgg cgggtgtcgg 120
ggctggctta actatgcggc atcagagcag attgtactga gagtgcacca tatgcggtgt 180
gaaataccgc acagatgcgt aaggagaaaa taccgcatca ggcgccattc gccattcagg 240
ctgcgcaact gttgggaagg gcgatcggtg cgggcctctt cgctattacg ccagctggcg 300

-continued

```
aaagggggat gtgctgcaag gcgattaagt tgggtaacgc cagggttttc ccagtcacga    360
cgttgtaaaa cgacggccag tgaattcttt ttagtttatg tatgtgtttt ttgtagttat    420
agatttaagc aagaaaagaa tacaaacaaa aaattgaaaa agattgattt agaattaaaa    480
agaaaaatat ttacgtaaga agggaaaata gtaaatgttg caagttcact aaactcctaa    540
attatgctgc cctttatatt ccctgttaca gcagccgagc caaaggtata taggctcctt    600
tgcattagca tgcgtaacaa accacctgtc agtttcaacc gaggtggtat ccgagagaat    660
tgtgtgattg ctttaattaa tttcggagaa tctcacatgc cactgaagat taaaaactgg    720
atgccagaaa aggggtgtcc aggtgtaaca tcaatagagg aagctgaaaa gtcttagaac    780
gggtaatctt ccaccaacct gatgggttcc tagatataat ctcgaaggga ataagtaggg    840
tgataccgca gaagtgtctg aatgtattaa ggtcctcaca gtttaaatcc cgctcacact    900
aacgtaggat tattataact caaaaaaatg gcattattct aagtaagtta aatatccgta    960
atctttaaac actatgtagt taggtctccc tcacaatcag tccatttggg tagctctaga   1020
tatcggatcc cgacgagctg caccgcggtg gcggccgtat cttttaccca tacgatgttc   1080
ctgactatgc gggctatccc tatgacgtcc cggactatgc aggatcctat ccatatgacg   1140
ttccagatta cgctgctcag tgcggccgcc tgagagtgca ccataccaca gcttttcaat   1200
tcaattcatc attttttttt tattcttttt tttgatttcg gtttctttga aatttttttg   1260
attcggtaat ctccgaacag aaggaagaac gaaggaagga gcacagactt agattggtat   1320
atatacgcat atgtagtgtt gaagaaacat gaaattgccc agtattctta acccaactgc   1380
acagaacaaa aacctgcagg aaacgaagat aaatcatgtc gaaagctaca tataaggaac   1440
gtgctgctac tcatcctagt cctgttgctg ccaagctatt taatatcatg cacgaaaagc   1500
aaacaaactt gtgtgcttca ttggatgttc gtaccaccaa ggaattactg gagttagttg   1560
aagcattagg tcccaaaatt tgtttactaa aaacacatgt ggatatcttg actgattttt   1620
ccatggaggg cacagttaag ccgctaaagg cattatccgc caagtacaat tttttactct   1680
tcgaagacag aaaatttgct gacattggta atacagtcaa attgcagtac tctgcgggtg   1740
tatacagaat agcagaatgg gcagacatta cgaatgcaca cggtgtggtg ggcccaggta   1800
ttgttagcgg tttgaagcag gcggcagaag aagtaacaaa ggaacctaga ggccttttga   1860
tgttagcaga attgtcatgc aagggctccc tatctactgg agaatatact aagggtactg   1920
ttgacattgc gaagagcgac aaagattttg ttatcggctt tattgctcaa agagacatgg   1980
gtggaagaga tgaaggttac gattggttga ttatgacacc cggtgtgggt ttagatgaca   2040
agggagacgc attgggtcaa cagtatagaa ccgtggatga tgtggtctct acaggatctg   2100
acattattat tgttggaaga ggactatttg caaagggaag ggatgctaag gtagagggtg   2160
aacgttacag aaaagcaggc tgggaagcat atttgagaag atgcggccag caaaactaaa   2220
aaactgtatt ataagtaaat gcatgtatac taaactcaca aattagagct tcaatttaat   2280
tatatcagtt attaccctat gcggtgtgaa ataccgcaca gatgcgtaag gagaaaatac   2340
cgcatcagga aattgtagcg gccgcgaatt tgagcttatc ttttacccat acgatgttcc   2400
tgactatgcg ggctatccct atgacgtccc ggactatgca ggatcctatc catatgacgt   2460
tccagattac gctactagcg gggggcccgg tgacgggccc gtcgactgca gaggcctgca   2520
tgcaagcttg gcgtaatcat ggtcatagct gtttcctgtg tgaaattgtt atccgctcac   2580
aattccacac aacatacgag ccggaagcat aaagtgtaaa gcctggggtg cctaatgagt   2640
gagctaactc acattaattg cgttgcgctc actgcccgct ttccagtcgg gaaacctgtc   2700
```

-continued

```
gtgccagctg cattaatgaa tcggccaacg cgcggggaga ggcggtttgc gtattgggcg   2760
ctcttccgct tcctcgctca ctgactcgct gcgctcggtc gttcggctgc ggcgagcggt   2820
atcagctcac tcaaaggcgg taatacggtt atccacagaa tcaggggata acgcaggaaa   2880
gaacatgtga gcaaaaggcc agcaaaaggc caggaaccgt aaaaaggccg cgttgctggc   2940
gtttttccat aggctccgcc cccctgacga gcatcacaaa aatcgacgct caagtcagag   3000
gtggcgaaac ccgacaggac tataaagata ccaggcgttt ccccctggaa gctccctcgt   3060
gcgctctcct gttccgaccc tgccgcttac cggatacctg tccgcctttc tcccttcggg   3120
aagcgtggcg ctttctcata gctcacgctg taggtatctc agttcggtgt aggtcgttcg   3180
ctccaagctg ggctgtgtgc acgaaccccc cgttcagccc gaccgctgcg ccttatccgg   3240
taactatcgt cttgagtcca acccggtaag acacgactta tcgccactgg cagcagccac   3300
tggtaacagg attagcagag cgaggtatgt aggcggtgct acagagttct tgaagtggtg   3360
gcctaactac ggctacacta gaagaacagt atttggtatc tgcgctctgc tgaagccagt   3420
taccttcgga aaaagagttg gtagctcttg atccggcaaa caaaccaccg ctggtagcgg   3480
tggttttttt gtttgcaagc agcagattac gcgcagaaaa aaaggatctc aagaagatcc   3540
tttgatcttt tctacggggt ctgacgctca gtggaacgaa aactcacgtt aagggatttt   3600
ggtcatgaga ttatcaaaaa ggatcttcac ctagatcctt ttaaattaaa aatgaagttt   3660
taaatcaatc taaagtatat atgagtaaac ttggtctgac agttaccaat gcttaatcag   3720
tgaggcacct atctcagcga tctgtctatt tcgttcatcc atagttgcct gactccccgt   3780
cgtgtagata actacgatac gggagggctt accatctggc cccagtgctg caatgatacc   3840
gcgagaccca cgctcaccgg ctccagattt atcagcaata aaccagccag ccggaagggc   3900
cgagcgcaga agtggtcctg caactttatc cgcctccatc cagtctatta attgttgccg   3960
ggaagctaga gtaagtagtt cgccagttaa tagtttgcgc aacgttgttg ccattgctac   4020
aggcatcgtg gtgtcacgct cgtcgtttgg tatggcttca ttcagctccg gttcccaacg   4080
atcaaggcga gttacatgat cccccatgtt gtgcaaaaaa gcggttagct ccttcggtcc   4140
tccgatcgtt gtcagaagta agttggccgc agtgttatca ctcatggtta tggcagcact   4200
gcataattct cttactgtca tgccatccgt aagatgcttt tctgtgactg gtgagtactc   4260
aaccaagtca ttctgagaat agtgtatgcg gcgaccgagt tgctcttgcc cggcgtcaat   4320
acgggataat accgcgccac atagcagaac tttaaaagtg ctcatcattg gaaaacgttc   4380
ttcggggcga aaactctcaa ggatcttacc gctgttgaga tccagttcga tgtaacccac   4440
tcgtgcaccc aactgatctt cagcatcttt tactttcacc agcgtttctg ggtgagcaaa   4500
aacaggaagg caaaatgccg caaaaaaggg aataagggcg acacggaaat gttgaatact   4560
catactcttc ctttttcaat attattgaag catttatcag ggttattgtc tcatgagcgg   4620
atacatattt gaatgtattt agaaaaataa acaaataggg gttccgcgca catttccccg   4680
aaaagtgcca cctgacgtct aagaaaccat tattatcatg acattaacct ataaaaatag   4740
gcgtatcacg aggccctttc gtctcgcgcg tttcggt                            4777
```

<210> SEQ ID NO 69
<211> LENGTH: 70
<212> TYPE: DNA
<213> ORGANISM: Artificial Sequence
<220> FEATURE:
<223> OTHER INFORMATION: primer

<400> SEQUENCE: 69
attgcatctt ggcttctagt ttttttatat tcaaaagggt tcttaagtgt agctatgacc 60
atgattacgc 70

<210> SEQ ID NO 70
<211> LENGTH: 73
<212> TYPE: DNA
<213> ORGANISM: Artificial Sequence
<220> FEATURE:
<223> OTHER INFORMATION: primer

<400> SEQUENCE: 70
ttttttctct atgatgactt attttatatg atatgtagcc tctgtgcttg tttttagttt 60
atgtatgtgt ttt 73

<210> SEQ ID NO 71
<211> LENGTH: 20
<212> TYPE: DNA
<213> ORGANISM: Artificial Sequence
<220> FEATURE:
<223> OTHER INFORMATION: primer

<400> SEQUENCE: 71
tggtggaaga ttacccgttc 20

<210> SEQ ID NO 72
<211> LENGTH: 20
<212> TYPE: DNA
<213> ORGANISM: Artificial Sequence
<220> FEATURE:
<223> OTHER INFORMATION: primer

<400> SEQUENCE: 72
cgcagccaat actccacata 20

<210> SEQ ID NO 73
<211> LENGTH: 32
<212> TYPE: DNA
<213> ORGANISM: Artificial Sequence
<220> FEATURE:
<223> OTHER INFORMATION: primer

<400> SEQUENCE: 73
aagcttatga cggtcgacca tgatttcaat ag 32

<210> SEQ ID NO 74
<211> LENGTH: 34
<212> TYPE: DNA
<213> ORGANISM: Artificial Sequence
<220> FEATURE:
<223> OTHER INFORMATION: primer

<400> SEQUENCE: 74
aagcttttaa atgtctccat gttttttatg agtc 34

<210> SEQ ID NO 75
<211> LENGTH: 28
<212> TYPE: DNA
<213> ORGANISM: Artificial Sequence
<220> FEATURE:
<223> OTHER INFORMATION: primer

<400> SEQUENCE: 75
gcgtcgacaa ttaaccctca ctaaaggg 28

-continued

<210> SEQ ID NO 76
<211> LENGTH: 28
<212> TYPE: DNA
<213> ORGANISM: Artificial Sequence
<220> FEATURE:
<223> OTHER INFORMATION: primer

<400> SEQUENCE: 76
gcgtcgacca aattaaagcc ttcgagcg 28

<210> SEQ ID NO 77
<211> LENGTH: 78
<212> TYPE: DNA
<213> ORGANISM: Artificial Sequence
<220> FEATURE:
<223> OTHER INFORMATION: primer

<400> SEQUENCE: 77
cgactatctt cgatctactc atattcatat tatcaattta ttatcatata tggtatatca 60
cgacgttgta aaacgacg 78

<210> SEQ ID NO 78
<211> LENGTH: 80
<212> TYPE: DNA
<213> ORGANISM: Artificial Sequence
<220> FEATURE:
<223> OTHER INFORMATION: primer

<400> SEQUENCE: 78
catcattaat actatctttt aacttccatt tatcaagtta ttaatccttg catttcggaa 60
acagctatga ccatgattac 80

<210> SEQ ID NO 79
<211> LENGTH: 25
<212> TYPE: DNA
<213> ORGANISM: Artificial Sequence
<220> FEATURE:
<223> OTHER INFORMATION: primer

<400> SEQUENCE: 79
caaccatatt ccactactga ggttc 25

<210> SEQ ID NO 80
<211> LENGTH: 26
<212> TYPE: DNA
<213> ORGANISM: Artificial Sequence
<220> FEATURE:
<223> OTHER INFORMATION: primer

<400> SEQUENCE: 80
ctgtcattca aatcggtgag taagag 26

<210> SEQ ID NO 81
<211> LENGTH: 22
<212> TYPE: DNA
<213> ORGANISM: Artificial Sequence
<220> FEATURE:
<223> OTHER INFORMATION: primer

<400> SEQUENCE: 81
cagaggaagg tgaacaaaat gc 22

<210> SEQ ID NO 82

-continued

<211> LENGTH: 21
<212> TYPE: DNA
<213> ORGANISM: Artificial Sequence
<220> FEATURE:
<223> OTHER INFORMATION: primer

<400> SEQUENCE: 82
tgctgtggga aatggtgata g 21

<210> SEQ ID NO 83
<211> LENGTH: 22
<212> TYPE: DNA
<213> ORGANISM: Artificial Sequence
<220> FEATURE:
<223> OTHER INFORMATION: primer

<400> SEQUENCE: 83
gctagagatt cctgacgatg ag 22

<210> SEQ ID NO 84
<211> LENGTH: 21
<212> TYPE: DNA
<213> ORGANISM: Artificial Sequence
<220> FEATURE:
<223> OTHER INFORMATION: primer

<400> SEQUENCE: 84
cccgttgtag tgtaagtctg c 21

<210> SEQ ID NO 85
<211> LENGTH: 21
<212> TYPE: DNA
<213> ORGANISM: Artificial Sequence
<220> FEATURE:
<223> OTHER INFORMATION: primer

<400> SEQUENCE: 85
aagactatgc ttaaaccccg g 21

<210> SEQ ID NO 86
<211> LENGTH: 19
<212> TYPE: DNA
<213> ORGANISM: Artificial Sequence
<220> FEATURE:
<223> OTHER INFORMATION: primer

<400> SEQUENCE: 86
gctgttgctg ttggattgg 19

<210> SEQ ID NO 87
<211> LENGTH: 1404
<212> TYPE: DNA
<213> ORGANISM: Escherichia coli

<400> SEQUENCE: 87
atgaatcaac aggatattga acaggtggtg aaagcggtac tgctgaaaat gcaaagcagt 60
gacacgccgt ccgccgccgt tcatgagatg ggcgttttcg cgtccctgga tgacgccgtt 120
gcggcagcca aagtcgccca gcaagggtta aaaagcgtgg caatgcgcca gttagccatt 180
gctgccattc gtgaagcagg cgaaaaacac gccagagatt tagcggaact tgccgtcagt 240
gaaaccggca tggggcgcgt tgaagataaa tttgcaaaaa acgtcgctca ggcgcgcggc 300
acaccaggcg ttgagtgcct ctctccgcaa gtgctgactg gcgacaacgg cctgacccta 360
attgaaaacg caccctgggg cgtggtggct tcggtgacgc cttccactaa cccggcggca 420

```
accgtaatta acaacgccat cagcctgatt gccgcgggca acagcgtcat ttttgccccg    480

catccggcgg cgaaaaaagt ctcccagcgg gcgattacgc tgctcaacca ggcgattgtt    540

gccgcaggtg ggccggaaaa cttactggtt actgtggcaa atccggatat cgaaaccgcg    600

caacgcttgt tcaagtttcc gggtatcggc ctgctggtgg taaccggcgg cgaagcggta    660

gtagaagcgg cgcgtaaaca caccaataaa cgtctgattg ccgcaggcgc tggcaacccg    720

ccggtagtgg tggatgaaac cgccgacctc gcccgtgccg ctcagtccat cgtcaaaggc    780

gcttctttcg ataacaacat catttgtgcc gacgaaaagg tactgattgt tgttgatagc    840

gtagccgatg aactgatgcg tctgatggaa ggccagcacg cggtgaaact gaccgcagaa    900

caggcgcagc agctgcaacc ggtgttgctg aaaaatatcg acgagcgcgg aaaaggcacc    960

gtcagccgtg actgggttgg tcgcgacgca ggcaaaatcg cggcggcaat cggccttaaa   1020

gttccgcaag aaacgcgcct gctgtttgtg gaaaccaccg cagaacatcc gtttgccgtg   1080

actgaactga tgatgccggt gttgcccgtc gtgcgcgtcg ccaacgtggc ggatgccatt   1140

gcgctagcgg tgaaactgga aggcggttgc caccacacgg cggcaatgca ctcgcgcaac   1200

atcgaaaaca tgaaccagat ggcgaatgct attgatacca gcattttcgt taagaacgga   1260

ccgtgcattg ccgggctggg gctgggcggg gaaggctgga ccaccatgac catcaccacg   1320

ccaaccggtg aaggggtaac cagcgcgcgt acgtttgtcc gtctgcgtcg ctgtgtatta   1380

gtcgatgcgt ttcgcattgt ttaa                                           1404
```

```
<210> SEQ ID NO 88
<211> LENGTH: 467
<212> TYPE: PRT
<213> ORGANISM: Escherichia coli

<400> SEQUENCE: 88

Met Asn Gln Gln Asp Ile Glu Gln Val Val Lys Ala Val Leu Leu Lys
  1               5                  10                  15

Met Gln Ser Ser Asp Thr Pro Ser Ala Ala Val His Glu Met Gly Val
             20                  25                  30

Phe Ala Ser Leu Asp Asp Ala Val Ala Ala Ala Lys Val Ala Gln Gln
         35                  40                  45

Gly Leu Lys Ser Val Ala Met Arg Gln Leu Ala Ile Ala Ala Ile Arg
     50                  55                  60

Glu Ala Gly Glu Lys His Ala Arg Asp Leu Ala Glu Leu Ala Val Ser
 65                  70                  75                  80

Glu Thr Gly Met Gly Arg Val Glu Asp Lys Phe Ala Lys Asn Val Ala
                 85                  90                  95

Gln Ala Arg Gly Thr Pro Gly Val Glu Cys Leu Ser Pro Gln Val Leu
            100                 105                 110

Thr Gly Asp Asn Gly Leu Thr Leu Ile Glu Asn Ala Pro Trp Gly Val
        115                 120                 125

Val Ala Ser Val Thr Pro Ser Thr Asn Pro Ala Ala Thr Val Ile Asn
    130                 135                 140

Asn Ala Ile Ser Leu Ile Ala Ala Gly Asn Ser Val Ile Phe Ala Pro
145                 150                 155                 160

His Pro Ala Ala Lys Lys Val Ser Gln Arg Ala Ile Thr Leu Leu Asn
                165                 170                 175

Gln Ala Ile Val Ala Ala Gly Gly Pro Glu Asn Leu Leu Val Thr Val
            180                 185                 190
```

```
Ala Asn Pro Asp Ile Glu Thr Ala Gln Arg Leu Phe Lys Phe Pro Gly
        195                 200                 205

Ile Gly Leu Leu Val Val Thr Gly Gly Glu Ala Val Val Glu Ala Ala
    210                 215                 220

Arg Lys His Thr Asn Lys Arg Leu Ile Ala Ala Gly Ala Gly Asn Pro
225                 230                 235                 240

Pro Val Val Val Asp Glu Thr Ala Asp Leu Ala Arg Ala Ala Gln Ser
                245                 250                 255

Ile Val Lys Gly Ala Ser Phe Asp Asn Asn Ile Ile Cys Ala Asp Glu
            260                 265                 270

Lys Val Leu Ile Val Val Asp Ser Val Ala Asp Glu Leu Met Arg Leu
        275                 280                 285

Met Glu Gly Gln His Ala Val Lys Leu Thr Ala Glu Gln Ala Gln Gln
    290                 295                 300

Leu Gln Pro Val Leu Leu Lys Asn Ile Asp Glu Arg Gly Lys Gly Thr
305                 310                 315                 320

Val Ser Arg Asp Trp Val Gly Arg Asp Ala Gly Lys Ile Ala Ala Ala
                325                 330                 335

Ile Gly Leu Lys Val Pro Gln Glu Thr Arg Leu Leu Phe Val Glu Thr
            340                 345                 350

Thr Ala Glu His Pro Phe Ala Val Thr Glu Leu Met Met Pro Val Leu
        355                 360                 365

Pro Val Val Arg Val Ala Asn Val Ala Asp Ala Ile Ala Leu Ala Val
    370                 375                 380

Lys Leu Glu Gly Gly Cys His His Thr Ala Ala Met His Ser Arg Asn
385                 390                 395                 400

Ile Glu Asn Met Asn Gln Met Ala Asn Ala Ile Asp Thr Ser Ile Phe
                405                 410                 415

Val Lys Asn Gly Pro Cys Ile Ala Gly Leu Gly Leu Gly Gly Glu Gly
            420                 425                 430

Trp Thr Thr Met Thr Ile Thr Thr Pro Thr Gly Glu Gly Val Thr Ser
        435                 440                 445

Ala Arg Thr Phe Val Arg Leu Arg Arg Cys Val Leu Val Asp Ala Phe
    450                 455                 460

Arg Ile Val
465


<210> SEQ ID NO 89
<211> LENGTH: 55
<212> TYPE: DNA
<213> ORGANISM: Artificial Sequence
<220> FEATURE:
<223> OTHER INFORMATION: primer

<400> SEQUENCE: 89

ctatagggcg aattggctag cttatcatta tcaatactcg ccatttcaaa gaata          55


<210> SEQ ID NO 90
<211> LENGTH: 66
<212> TYPE: DNA
<213> ORGANISM: Artificial Sequence
<220> FEATURE:
<223> OTHER INFORMATION: primer

<400> SEQUENCE: 90

ctcgaggggg ggcccggtac ctcgaaacta agttctggtg ttttaaaact aaaaaaaaga     60

ctaact                                                                66
```

<210> SEQ ID NO 91
<211> LENGTH: 6110
<212> TYPE: DNA
<213> ORGANISM: Artificial Sequence
<220> FEATURE:
<223> OTHER INFORMATION: Synthetic pCS-Ex1 vector

<400> SEQUENCE: 91
ctaaattgta agcgttaata ttttgttaaa attcgcgtta aatttttgtt aaatcagctc 60 atttttaac caataggccg aaatcggcaa aatcccttat aaatcaaaag aatagaccga 120
gatagggttg agtacgcatt taagcataaa cacgcactat gccgttcttc tcatgtatat 180
atatatacag gcaacacgca gatataggtg cgacgtgaac agtgagctgt atgtgcgcag 240
ctcgcgttgc attttcggaa gcgctcgttt tcggaaacgc tttgaagttc ctattccgaa 300
gttcctattc tctagctaga aagtatagga acttcagagc gcttttgaaa accaaaagcg 360
ctctgaagac gcactttcaa aaaaccaaaa acgcaccgga ctgtaacgag ctactaaaat 420
attgcgaata ccgcttccac aaacattgct caaaagtatc tctttgctat atatctctgt 480
gctatatccc tatataacct acccatccac ctttcgctcc ttgaacttgc atctaaactc 540
gacctctaca tttttatgt ttatctctag tattactctt tagacaaaaa aattgtagta 600
agaactattc atagagtgaa tcgaaaacaa tacgaaaatg taaacatttc ctatacgtag 660
tatatagaga caaaatagaa gaaaccgttc ataattttct gaccaatgaa gaatcatcaa 720
cgctatcact ttctgttcac aaagtatgcg caatccacat cggtatagaa tataatcggg 780
gatgccttta tcttgaaaaa atgcacccgc agcttcgcta gtaatcagta aacgcgggaa 840
gtggagtcag gcttttttta tggaagagaa aatagacacc aaagtagcct tcttctaacc 900
ttaacggacc tacagtgcaa aaagttatca agagactgca ttatagagcg cacaaaggag 960
aaaaaaagta atctaagatg ctttgttaga aaaatagcgc tctcgggatg catttttgta 1020
gaacaaaaaa gaagtataga ttctttgttg gtaaaatagc gctctcgcgt tgcatttctg 1080
ttctgtaaaa atgcagctca gattctttgt ttgaaaaatt agcgctctcg cgttgcattt 1140
ttgttttaca aaaatgaagc acagattctt cgttggtaaa atagcgcttt cgcgttgcat 1200
ttctgttctg taaaaatgca gctcagattc tttgtttgaa aaattagcgc tctcgcgttg 1260
catttttgtt ctacaaaatg aagcacagat gcttcgttaa tgtgctgcaa ggcgattaag 1320
ttgggtaacg ccagggtttt cccagtcacg acgttgtaaa acgacggcca gtgaattgta 1380
atacgactca ctatagggcg aattggctag cttatcatta tcaatactcg ccatttcaaa 1440
gaatacgtaa ataattaata gtagtgattt tcctaacttt atttagtcaa aaaattagcc 1500
ttttaattct gctgtaaccc gtacatgccc aaaatagggg gcgggttaca cagaatatat 1560
aacatcgtag gtgtctgggt gaacagttta ttcctggcat ccactaaata taatggagcc 1620
cgctttttaa gctggcatcc agaaaaaaaa agaatcccag caccaaaata ttgttttctt 1680
caccaaccat cagttcatag gtccattctc ttagcgcaac tacagagaac aggggcacaa 1740
acaggcaaaa aacgggcaca acctcaatgg agtgatgcaa cctgcctgga gtaaatgatg 1800
acacaaggca attgacccac gcatgtatct atctcatttt cttacacctt ctattacctt 1860
ctgctctctc tgatttggaa aaagctgaaa aaaaaggttg aaaccagttc cctgaaatta 1920
ttcccctact tgactaataa gtatataaag acggtaggta ttgattgtaa ttctgtaaat 1980
ctatttctta aacttcttaa attctacttt tatagttagt cttttttta gttttaaaac 2040

-continued

```
accagaactt agtttcgagg taccgggccc cccctcgagg tcgacggtat cgataagctt   2100
gatatcgaat tcctgcagcc cgggggatcc actagttcta gagcggccgc caccgcggtg   2160
gagctcggtt ctgcttatcc ttacgacgtg cctgactacg cctgaacccg atgcaaatga   2220
gacgatcgtc tattcctggt ccggttttct ctgccctctc ttctattcac ttttttata    2280
ctttatataa aattatataa atgacataac tgaaacgcca cacgtcctct cctattcgtt   2340
aacgcctgtc tgtagcgctg ttactgaagc tgcgcaagta gtttttcac cgtataggcc    2400
ctctttttct ctctctttct ttctctcccg cgctgatctc ttcttcgaaa cacagagtgc   2460
accataccac cttttcaatt catcattttt tttttattct ttttttgat ttcggtttcc    2520
ttgaaatttt tttgattcgg taatctccga acagaaggaa gaacgaagga aggagcacag   2580
acttagattg gtatatatac gcatatgtag tgttgaagaa acatgaaatt gcccagtatt   2640
cttaacccaa ctgcacagaa caaaaacctc caggaaacga agataaatca tgtcgaaagc   2700
tacatataag gaacgtgctg ctactcatcc tagtcctgtt gctgccaagc tatttaatat   2760
catgcacgaa aagcaaacaa acttgtgtgc ttcattggat gttcgtacca ccaaggaatt   2820
actggagtta gttgaagcat taggtcccaa aatttgttta ctaaaaacac atgtggatat   2880
cttgactgat ttttccatgg agggcacagt taagccgcta aaggcattat ccgccaagta   2940
caatttttta ctcttcgaag acagaaaatt tgctgacatt ggtaatacag tcaaattgca   3000
gtactctgcg ggtgtataca gaatagcaga atgggcagac attacgaatg cacacggtgt   3060
ggtgggccca ggtattgtta gcggtttgaa gcaggcggca gaagaagtaa caaaggaacc   3120
tagaggcctt ttgatgttag cagaattgtc atgcaagggc tccctatcta ctggagaata   3180
tactaagggt actgttgaca ttgcgaagag cgacaaagat tttgttatcg gctttattgc   3240
tcaaagagac atgggtggaa gagatgaagg ttacgattgg ttgattatga cacccggtgt   3300
gggtttagat gacaagggag acgcattggg tcaacagtat agaaccgtgg atgatgtggt   3360
ctctacagga tctgacatta ttattgttgg aagaggacta tttgcaaagg gaagggatgc   3420
taaggtagag ggtgaacgtt acagaaaagc aggctgggaa gcatatttga gaagatgcgg   3480
ccagcaaaac taatcatgta attagttatg tcacgcttac attcacgccc tccccccaca   3540
tccgctctaa ccgaaaagga aggagttaga caacctgaag tctaggtccc tatttatttt   3600
tttatagtta tgttagtatt aagaacgtta tttatatttc aaatttttct ttttttctg    3660
tacagacgcg tgtacgcatg taacattata ctgaaaacct tgcttgagaa ggttttggga   3720
cgctcgaagg ctttaatttg cgtctgtagc gctgttactg aagctgcgca agtagttttt   3780
tcaccgtata ggccctcttt ttctctctct ttctttctct cccgcgctga tctcttcttc   3840
gaaacatcat gaataaaaag aaaaaggaaa tcaagaaaaa aaagccataa tttatcccac   3900
attttttttt attgtcgctg ttcacaccgc ataacgaaga tattggctag ctaaccagct   3960
tttgttccct ttagtgaggg ttaatttcga gcttggcgta atcatggtca tagctgtttc   4020
ctgtgtgaaa ttgttatccg ctcacaattc cacacaacat acgagccgga agcataaagt   4080
gtaaagcctg gggtgcctaa tgagtgagct aactcacatt aattgcgttg cgctcactgc   4140
ccgctttcca gtcgggaaac ctgtcgtgcc agctgcatta atgaatcggc caacgcgcgg   4200
ggagaggcgg tttgcgtatt gggcgctctt ccgcttcctc gctcactgac tcgctgcgct   4260
cggtcgttcg gctgcggcga gcggtatcag ctcactcaaa ggcggtaata cggttatcca   4320
cagaatcagg ggataacgca ggaaagaaca tgtgagcaaa aggccagcaa aaggccagga   4380
accgtaaaaa ggccgcgttg ctggcgtttt tccataggct ccgcccccct gacgagcatc   4440
```

acaaaaatcg acgctcaagt cagaggtggc gaaacccgac aggactataa agataccagg 4500
cgtttccccc tggaagctcc ctcgtgcgct ctcctgttcc gaccctgccg cttaccggat 4560
acctgtccgc ctttctccct tcgggaagcg tggcgctttc tcatagctca cgctgtaggt 4620
atctcagttc ggtgtaggtc gttcgctcca agctgggctg tgtgcacgaa ccccccgttc 4680
agcccgaccg ctgcgcctta tccggtaact atcgtcttga gtccaacccg gtaagacacg 4740
acttatcgcc actggcagca gccactggta acaggattag cagagcgagg tatgtaggcg 4800
gtgctacaga gttcttgaag tggtggccta actacggcta cactagaagg acagtatttg 4860
gtatctgcgc tctgctgaag ccagttacct tcggaaaaag agttggtagc tcttgatccg 4920
gcaaacaaac caccgctggt agcggtggtt tttttgtttg caagcagcag attacgcgca 4980
gaaaaaaagg atctcaagaa gatcctttga tcttttctac ggggtctgac gctcagtgga 5040
acgaaaactc acgttaaggg attttggtca tgagattatc aaaaaggatc ttcacctaga 5100
tccttttaaa ttaaaaatga agttttaaat caatctaaag tatatatgag taaacttggt 5160
ctgacatcag aagaactcgt caagaaggcg atagaaggcg atgcgctgcg aatcgggagc 5220
ggcgataccg taaagcacga ggaagcggtc agcccattcg ccgccaagct cttcagcaat 5280
atcacgggta gccaacgcta tgtcctgata gcggtccgcc acacccagcc ggccacagtc 5340
gatgaatcca gaaaagcggc cattttccac catgatattc ggcaagcagg catcgccatg 5400
ggtcacgacg agatcctcgc cgtcgggcat gctcgccttg agcctggcga acagttcggc 5460
tggcgcgagc ccctgatgct cttcgtccag atcatcctga tcgacaagac cggcttccat 5520
ccgagtacgt gctcgctcga tgcgatgttt cgcttggtgg tcgaatgggc aggtagccgg 5580
atcaagcgta tgcagccgcc gcattgcatc agccatgatg gatactttct cggcaggagc 5640
aaggtgagat gacaggagat cctgccccgg cacttcgccc aatagcagcc agtcccttcc 5700
cgcttcagtg acaacgtcga gcacagctgc gcaaggaacg cccgtcgtgg ccagccacga 5760
tagccgcgct gcctcgtctt gcagttcatt cagggcaccg gacaggtcgg tcttgacaaa 5820
aagaaccggg cgcccctgcg ctgacagccg gaacacggcg gcatcagagc agccgattgt 5880
ctgttgtgcc cagtcatagc cgaatagcct ctccacccaa gcggccggag aacctgcgtg 5940
caatccatct tgttcaattc gagtgcattc aacatcagcc atactcttcc tttttcaata 6000
ttattgaagc atttatcagg gttattgtct catgagcgga tacatatttg aatgtattta 6060
gaaaaataaa caaatagggg ttccgcgcac atttccccga aaagtgccac 6110

<210> SEQ ID NO 92
<211> LENGTH: 55
<212> TYPE: DNA
<213> ORGANISM: Artificial Sequence
<220> FEATURE:
<223> OTHER INFORMATION: primer

<400> SEQUENCE: 92
accagaactt agtttcgaga aacaatgaat caacaggata ttgaacaggt ggtga 55

<210> SEQ ID NO 93
<211> LENGTH: 50
<212> TYPE: DNA
<213> ORGANISM: Artificial Sequence
<220> FEATURE:
<223> OTHER INFORMATION: primer

<400> SEQUENCE: 93

-continued gtaaggataa gcagaaccgt taaacaatgc gaaacgcatc gactaataca 50

<210> SEQ ID NO 94
<211> LENGTH: 7413
<212> TYPE: DNA
<213> ORGANISM: Artificial Sequence
<220> FEATURE:
<223> OTHER INFORMATION: Synthetic MD1040 vector

<400> SEQUENCE: 94
ctaaattgta agcgttaata ttttgttaaa attcgcgtta aatttttgtt aaatcagctc 60 atttttttaac caataggccg aaatcggcaa aatcccttat aaatcaaaag aatagaccga 120
gatagggttg agtacgcatt taagcataaa cacgcactat gccgttcttc tcatgtatat 180
atatatacag gcaacacgca gatataggtg cgacgtgaac agtgagctgt atgtgcgcag 240
ctcgcgttgc attttcggaa gcgctcgttt tcggaaacgc tttgaagttc ctattccgaa 300
gttcctattc tctagctaga aagtatagga acttcagagc gcttttgaaa accaaaagcg 360
ctctgaagac gcactttcaa aaaaccaaaa acgcaccgga ctgtaacgag ctactaaaat 420
attgcgaata ccgcttccac aaacattgct caaaagtatc tctttgctat atatctctgt 480
gctatatccc tatataacct acccatccac ctttcgctcc ttgaacttgc atctaaactc 540
gacctctaca tttttttatgt ttatctctag tattactctt tagacaaaaa aattgtagta 600
agaactattc atagagtgaa tcgaaaacaa tacgaaaatg taaacatttc ctatacgtag 660
tatatagaga caaaatagaa gaaaccgttc ataattttct gaccaatgaa gaatcatcaa 720
cgctatcact ttctgttcac aaagtatgcg caatccacat cggtatagaa tataatcggg 780
gatgccttta tcttgaaaaa atgcacccgc agcttcgcta gtaatcagta aacgcgggaa 840
gtggagtcag gcttttttta tggaagagaa aatagacacc aaagtagcct tcttctaacc 900
ttaacggacc tacagtgcaa aaagttatca agagactgca ttatagagcg cacaaaggag 960
aaaaaaagta atctaagatg ctttgttaga aaaatagcgc tctcgggatg catttttgta 1020
gaacaaaaaa gaagtataga ttctttgttg gtaaaatagc gctctcgcgt tgcatttctg 1080
ttctgtaaaa atgcagctca gattctttgt ttgaaaaatt agcgctctcg cgttgcattt 1140
ttgttttaca aaaatgaagc acagattctt cgttggtaaa atagcgcttt cgcgttgcat 1200
ttctgttctg taaaaatgca gctcagattc tttgtttgaa aaattagcgc tctcgcgttg 1260
catttttgtt ctacaaaatg aagcacagat gcttcgttaa tgtgctgcaa ggcgattaag 1320
ttgggtaacg ccagggtttt cccagtcacg acgttgtaaa acgacggcca gtgaattgta 1380
atacgactca ctatagggcg aattggctag cttatcatta tcaatactcg ccatttcaaa 1440
gaatacgtaa ataattaata gtagtgattt tcctaacttt atttagtcaa aaaattagcc 1500
ttttaattct gctgtaaccc gtacatgccc aaaatagggg gcgggttaca cagaatatat 1560
aacatcgtag gtgtctgggt gaacagttta ttcctggcat ccactaaata taatggagcc 1620
cgctttttaa gctggcatcc agaaaaaaaa agaatcccag caccaaaata ttgttttctt 1680
caccaaccat cagttcatag gtccattctc ttagcgcaac tacagagaac aggggcacaa 1740
acaggcaaaa aacgggcaca acctcaatgg agtgatgcaa cctgcctgga gtaaatgatg 1800
acacaaggca attgacccac gcatgtatct atctcatttt cttacacctt ctattacctt 1860
ctgctctctc tgatttggaa aaagctgaaa aaaaaggttg aaaccagttc cctgaaatta 1920
ttcccctact tgactaataa gtatataaag acggtaggta ttgattgtaa ttctgtaaat 1980
ctatttctta aacttcttaa attctacttt tatagttagt cttttttttta gttttaaaac 2040

-continued

```
accagaactt agtttcgaga aacaatgaat caacaggata ttgaacaggt ggtgaaagcg   2100
gtactgctga aaatgcaaag cagtgacacg ccgtccgccg ccgttcatga gatgggcgtt   2160
ttcgcgtccc tggatgacgc cgttgcggca gccaaagtcg cccagcaagg gttaaaaagc   2220
gtggcaatgc gccagttagc cattgctgcc attcgtgaag caggcgaaaa acacgccaga   2280
gatttagcgg aacttgccgt cagtgaaacc ggcatggggc gcgttgaaga taaatttgca   2340
aaaaacgtcg ctcaggcgcg cggcacacca ggcgttgagt gcctctctcc gcaagtgctg   2400
actggcgaca acggcctgac cctaattgaa aacgcaccct ggggcgtggt ggcttcggtg   2460
acgccttcca ctaacccggc ggcaaccgta attaacaacg ccatcagcct gattgccgcg   2520
ggcaacagcg tcatttttgc ccgcatccg gcggcgaaaa aagtctccca gcgggcgatt   2580
acgctgctca accaggcgat tgttgccgca ggtgggccgg aaaacttact ggttactgtg   2640
gcaaatccgg atatcgaaac cgcgcaacgc ttgttcaagt ttccgggtat cggcctgctg   2700
gtggtaaccg gcggcgaagc ggtagtagaa gcggcgcgta aacacaccaa taaacgtctg   2760
attgccgcag gcgctggcaa cccgccggta gtggtggatg aaaccgccga cctcgcccgt   2820
gccgctcagt ccatcgtcaa aggcgcttct ttcgataaca acatcatttg tgccgacgaa   2880
aaggtactga ttgttgttga tagcgtagcc gatgaactga tgcgtctgat ggaaggccag   2940
cacgcggtga aactgaccgc agaacaggcg cagcagctgc aaccggtgtt gctgaaaaat   3000
atcgacgagc gcggaaaagg caccgtcagc cgtgactggg ttggtcgcga cgcaggcaaa   3060
atcgcggcgg caatcggcct taaagttccg caagaaacgc gcctgctgtt tgtggaaacc   3120
accgcagaac atccgtttgc cgtgactgaa ctgatgatgc cggtgttgcc cgtcgtgcgc   3180
gtcgccaacg tggcggatgc cattgcgcta gcggtgaaac tggaaggcgg ttgccaccac   3240
acggcggcaa tgcactcgcg caacatcgaa aacatgaacc agatggcgaa tgctattgat   3300
accagcattt tcgttaagaa cggaccgtgc attgccgggc tggggctggg cggggaaggc   3360
tggaccacca tgaccatcac cacgccaacc ggtgaagggg taaccagcgc gcgtacgttt   3420
gtccgtctgc gtcgctgtgt attagtcgat gcgtttcgca ttgtttaacg gttctgctta   3480
tccttacgac gtgcctgact acgcctgaac ccgatgcaaa tgagacgatc gtctattcct   3540
ggtccggttt tctctgccct ctcttctatt cacttttttt atactttata taaaattata   3600
taaatgacat aactgaaacg ccacacgtcc tctcctattc gttaacgcct gtctgtagcg   3660
ctgttactga agctgcgcaa gtagtttttt caccgtatag gccctctttt tctctctctt   3720
tctttctctc ccgcgctgat ctcttcttcg aaacacagag tgcaccatac cacctttca    3780
attcatcatt tttttttat tcttttttt gatttcggtt tccttgaaat ttttttgatt     3840
cggtaatctc cgaacagaag gaagaacgaa ggaaggagca cagacttaga ttggtatata   3900
tacgcatatg tagtgttgaa gaaacatgaa attgcccagt attcttaacc caactgcaca   3960
gaacaaaaac ctccaggaaa cgaagataaa tcatgtcgaa agctacatat aaggaacgtg   4020
ctgctactca tcctagtcct gttgctgcca agctatttaa tatcatgcac gaaaagcaaa   4080
caaacttgtg tgcttcattg gatgttcgta ccaccaagga attactggag ttagttgaag   4140
cattaggtcc caaaatttgt ttactaaaaa cacatgtgga tatcttgact gatttttcca   4200
tggagggcac agttaagccg ctaaaggcat tatccgccaa gtacaatttt ttactcttcg   4260
aagacagaaa atttgctgac attggtaata cagtcaaatt gcagtactct gcgggtgtat   4320
acagaatagc agaatgggca gacattacga atgcacacgg tgtggtgggc ccaggtattg   4380
```

-continued

```
ttagcggttt gaagcaggcg gcagaagaag taacaaagga acctagaggc cttttgatgt   4440
tagcagaatt gtcatgcaag ggctccctat ctactggaga atatactaag ggtactgttg   4500
acattgcgaa gagcgacaaa gattttgtta tcggctttat tgctcaaaga gacatgggtg   4560
gaagagatga aggttacgat tggttgatta tgacacccgg tgtgggttta gatgacaagg   4620
gagacgcatt gggtcaacag tatagaaccg tggatgatgt ggtctctaca ggatctgaca   4680
ttattattgt tggaagagga ctatttgcaa agggaaggga tgctaaggta gagggtgaac   4740
gttacagaaa agcaggctgg gaagcatatt tgagaagatg cggccagcaa aactaatcat   4800
gtaattagtt atgtcacgct tacattcacg ccctcccccc acatccgctc taaccgaaaa   4860
ggaaggagtt agacaacctg aagtctaggt ccctatttat ttttttatag ttatgttagt   4920
attaagaacg ttatttatat ttcaaatttt tctttttttt ctgtacagac gcgtgtacgc   4980
atgtaacatt atactgaaaa ccttgcttga gaaggttttg ggacgctcga aggctttaat   5040
ttgcgtctgt agcgctgtta ctgaagctgc gcaagtagtt ttttcaccgt ataggccctc   5100
tttttctctc tctttctttc tctcccgcgc tgatctcttc ttcgaaacat catgaataaa   5160
aagaaaaagg aaatcaagaa aaaaaagcca taatttatcc cacatttttt tttattgtcg   5220
ctgttcacac cgcataacga agatattggc tagctaacca gcttttgttc cctttagtga   5280
gggttaattt cgagcttggc gtaatcatgg tcatagctgt ttcctgtgtg aaattgttat   5340
ccgctcacaa ttccacacaa catacgagcc ggaagcataa agtgtaaagc ctggggtgcc   5400
taatgagtga gctaactcac attaattgcg ttgcgctcac tgcccgcttt ccagtcggga   5460
aacctgtcgt gccagctgca ttaatgaatc ggccaacgcg cggggagagg cggtttgcgt   5520
attgggcgct cttccgcttc ctcgctcact gactcgctgc gctcggtcgt tcggctgcgg   5580
cgagcggtat cagctcactc aaaggcggta atacggttat ccacagaatc aggggataac   5640
gcaggaaaga acatgtgagc aaaaggccag caaaaggcca ggaaccgtaa aaaggccgcg   5700
ttgctggcgt ttttccatag gctccgcccc cctgacgagc atcacaaaaa tcgacgctca   5760
agtcagaggt ggcgaaaccc gacaggacta taaagatacc aggcgtttcc ccctggaagc   5820
tccctcgtgc gctctcctgt tccgaccctg ccgcttaccg gatacctgtc cgcctttctc   5880
ccttcgggaa gcgtggcgct ttctcatagc tcacgctgta ggtatctcag ttcggtgtag   5940
gtcgttcgct ccaagctggg ctgtgtgcac gaaccccccg ttcagcccga ccgctgcgcc   6000
ttatccggta actatcgtct tgagtccaac ccggtaagac acgacttatc gccactggca   6060
gcagccactg gtaacaggat tagcagagcg aggtatgtag gcggtgctac agagttcttg   6120
aagtggtggc ctaactacgg ctacactaga aggacagtat ttggtatctg cgctctgctg   6180
aagccagtta ccttcggaaa aagagttggt agctcttgat ccggcaaaca aaccaccgct   6240
ggtagcggtg gtttttttgt ttgcaagcag cagattacgc gcagaaaaaa aggatctcaa   6300
gaagatcctt tgatcttttc tacggggtct gacgctcagt ggaacgaaaa ctcacgttaa   6360
gggattttgg tcatgagatt atcaaaaagg atcttcacct agatcctttt aaattaaaaa   6420
tgaagtttta aatcaatcta aagtatatat gagtaaactt ggtctgacat cagaagaact   6480
cgtcaagaag gcgatagaag gcgatgcgct gcgaatcggg agcggcgata ccgtaaagca   6540
cgaggaagcg gtcagcccat tcgccgccaa gctcttcagc aatatcacgg gtagccaacg   6600
ctatgtcctg atagcggtcc gccacaccca gccggccaca gtcgatgaat ccagaaaagc   6660
ggccattttc caccatgata ttcggcaagc aggcatcgcc atgggtcacg acgagatcct   6720
cgccgtcggg catgctcgcc ttgagcctgg cgaacagttc ggctggcgcg agcccctgat   6780
```

-continued gctcttcgtc cagatcatcc tgatcgacaa gaccggcttc catccgagta cgtgctcgct 6840
cgatgcgatg tttcgcttgg tggtcgaatg ggcaggtagc cggatcaagc gtatgcagcc 6900
gccgcattgc atcagccatg atggatactt tctcggcagg agcaaggtga gatgacagga 6960
gatcctgccc cggcacttcg cccaatagca gccagtccct tcccgcttca gtgacaacgt 7020
cgagcacagc tgcgcaagga acgcccgtcg tggccagcca cgatagccgc gctgcctcgt 7080
cttgcagttc attcagggca ccggacaggt cggtcttgac aaaaagaacc gggcgcccct 7140
gcgctgacag ccggaacacg gcggcatcag agcagccgat tgtctgttgt gcccagtcat 7200
agccgaatag cctctccacc caagcggccg gagaacctgc gtgcaatcca tcttgttcaa 7260
ttcgagtgca ttcaacatca gccatactct tcctttttca atattattga agcatttatc 7320
agggttattg tctcatgagc ggatacatat ttgaatgtat ttagaaaaat aaacaaatag 7380
gggttccgcg cacatttccc cgaaaagtgc cac 7413

<210> SEQ ID NO 95
<211> LENGTH: 59
<212> TYPE: DNA
<213> ORGANISM: Artificial Sequence
<220> FEATURE:
<223> OTHER INFORMATION: primer

<400> SEQUENCE: 95
aatcttgtgc tattgcagtc ctcttttata tacagtataa tacgactcac tatagggcg 59

<210> SEQ ID NO 96
<211> LENGTH: 60
<212> TYPE: DNA
<213> ORGANISM: Artificial Sequence
<220> FEATURE:
<223> OTHER INFORMATION: primer

<400> SEQUENCE: 96
atgcgaattg cgtaattcac ggcgataacg tagtattaat taaccctcac taaagggaac 60

<210> SEQ ID NO 97
<211> LENGTH: 19
<212> TYPE: DNA
<213> ORGANISM: Artificial Sequence
<220> FEATURE:
<223> OTHER INFORMATION: primer

<400> SEQUENCE: 97
gcccacaact tatcaagtg 19

<210> SEQ ID NO 98
<211> LENGTH: 19
<212> TYPE: DNA
<213> ORGANISM: Artificial Sequence
<220> FEATURE:
<223> OTHER INFORMATION: primer

<400> SEQUENCE: 98
ttataagaca agcgcaggg 19